United States Patent
Hu et al.

(10) Patent No.: US 10,172,948 B2
(45) Date of Patent: *Jan. 8, 2019

(54) METHODS FOR OXIME CONJUGATION TO KETONE-MODIFIED POLYPEPTIDES

(71) Applicants: Qi-Ying Hu, Needham, MA (US); Hidetomo Imase, Somerville, MA (US)

(72) Inventors: Qi-Ying Hu, Needham, MA (US); Hidetomo Imase, Somerville, MA (US)

(73) Assignee: Novartis AG, Basel (CH)

( * ) Notice: Subject to any disclaimer, the term of this patent is extended or adjusted under 35 U.S.C. 154(b) by 682 days.

This patent is subject to a terminal disclaimer.

(21) Appl. No.: 14/551,187

(22) Filed: Nov. 24, 2014

(65) Prior Publication Data

US 2015/0150998 A1 Jun. 4, 2015

Related U.S. Application Data

(60) Provisional application No. 62/002,614, filed on May 23, 2014, provisional application No. 61/909,236, filed on Nov. 26, 2013.

(51) Int. Cl.
| | | |
|---|---|---|
| *A61K 38/00* | (2006.01) | |
| *A61K 47/48* | (2006.01) | |
| *C07K 1/113* | (2006.01) | |
| *C07K 7/64* | (2006.01) | |
| *A61K 47/54* | (2017.01) | |
| *A61K 47/62* | (2017.01) | |
| *A61K 47/64* | (2017.01) | |
| *A61K 47/68* | (2017.01) | |

(52) U.S. Cl.
CPC ...... *A61K 47/48038* (2013.01); *A61K 47/542* (2017.08); *A61K 47/62* (2017.08); *A61K 47/646* (2017.08); *A61K 47/68* (2017.08); *A61K 47/6803* (2017.08); *A61K 47/6849* (2017.08); *C07K 1/1133* (2013.01); *C07K 7/64* (2013.01); *C07K 2317/40* (2013.01)

(58) Field of Classification Search
CPC .......... A61K 47/48038; C07K 2317/40; C07K 7/64; C07K 1/1133
See application file for complete search history.

(56) References Cited

U.S. PATENT DOCUMENTS

| | | |
|---|---|---|
| 6,239,110 B1 | 5/2001 | Eyal et al. |
| 8,673,848 B2 | 3/2014 | Zecri et al. |
| 9,067,971 B2 | 6/2015 | Zecri et al. |
| 2006/0210526 A1 | 9/2006 | Brocchini et al. |
| 2013/0196899 A1 | 8/2013 | Zecri et al. |
| 2014/0142022 A1 | 5/2014 | Zecri et al. |
| 2015/0252076 A1 | 9/2015 | Zecri et al. |
| 2015/0290009 A1 | 10/2015 | Hu et al. |

FOREIGN PATENT DOCUMENTS

| | | |
|---|---|---|
| WO | 1999/13062 A1 | 3/1999 |
| WO | 1999/13063 A1 | 3/1999 |
| WO | 2005/007197 A2 | 1/2005 |
| WO | 2008/157380 A2 | 12/2008 |
| WO | 2010/025510 A1 | 3/2010 |
| WO | 2011/018613 A1 | 2/2011 |
| WO | 2013/111110 A2 | 8/2013 |
| WO | 2014/059028 A1 | 4/2014 |
| WO | 2014/078623 A2 | 5/2014 |
| WO | 2014/083505 A1 | 6/2014 |

OTHER PUBLICATIONS

Bendet et al., Biophysical Journal Volume, 1967, 7, 111-119.*
Chemical & Engineer News, Chemical & Engineering News: Latest News, Nov. 29, 2006.*
Del Borgo, Mark P. et al.: "Conformationally constrained single-chain peptide mimics of relaxin B-chain secondary structure", Journal of Peptide Science, (2005), vol. 11, pp. 564-571.
Roof, Rebecca A. et al.: "A covalent peptide inhibitor of RGS4 indentified in a focused one-bead, one compound library screen", BMC Pharmacology, (2009), vol. 9, No. 9, pp. 1-11.
CAS Registry No. 1093647-54-1, Chemical or Trade Name: L-Cysteinamide, N-acetyl-S-(3-mercapto-2-oxopropyl)-L-cysteinyl-L-histidyl-L-alanyl-L-valyl-, cyclic (1-5)-thioether, Entry Date: Jan. 14, 2009.
CAS Registry No. 1344196-27-5, Chemical or Trade Name: 2-Propanone, 1,3-bis(propylthio), Entry Date: Nov. 10, 2011.
CAS Registry No. 1448547-22-5, Chemical or Trade Name: Index Name Not Yet Assigned, Entry Date: Aug. 16, 2013.
CAS Registry No. 1613023-90-7, Chemical or Trade Name: Index Name Not Yet Assigned, Entry Date: Jun. 27, 2014.
Shandiz et al., Intramolecular cross-linking evaluated as a structural probe of the protein folding transition state. Biochemistry. Dec. 4, 2007;46(48):13711-9. Epub Nov. 7, 2007.

(Continued)

*Primary Examiner* — Kaipeen E Yang
(74) *Attorney, Agent, or Firm* — Lian Ouyang

(57) ABSTRACT

The invention provides improved methods to prepare protein conjugates from a ketone-modified protein. In one embodiment, the protein is prepared by linking two free cysteines by reaction with a 1,3-dihaloacetone or similar ketone-containing reactant, linking the sulfur atoms of the two cysteines together. The ketone inserted between the sulfur atoms is then used to form an oxime, thus conjugating the protein to a payload. In another embodiment, two cysteine residues are tied together by reaction with a 1,3-dihaloacetone or similar reactant, and the new ketone is used to form an oxime with a suitable payload molecule, thus conjugating the protein to a payload. The method provides improved reaction conditions for the oxime formation, whereby higher yields and improved product homogeneity are achieved.

13 Claims, 9 Drawing Sheets

Specification includes a Sequence Listing.

(56) References Cited

OTHER PUBLICATIONS

Carrico et al., N-Terminal labeling of filamentous phage to create cancer marker imaging agents. ACS Nano. Aug. 28, 2012;6(8):6675-80. Epub Aug. 6, 2012.

Xu et al., A novel approach to chemical microarray using ketone-modified macromolecular scaffolds: application in micro cell-adhesion assay. Mol Divers. 2004;8(3):301-10.

* cited by examiner

Figure 2. Coupling two conjugates having complementary coupling groups.
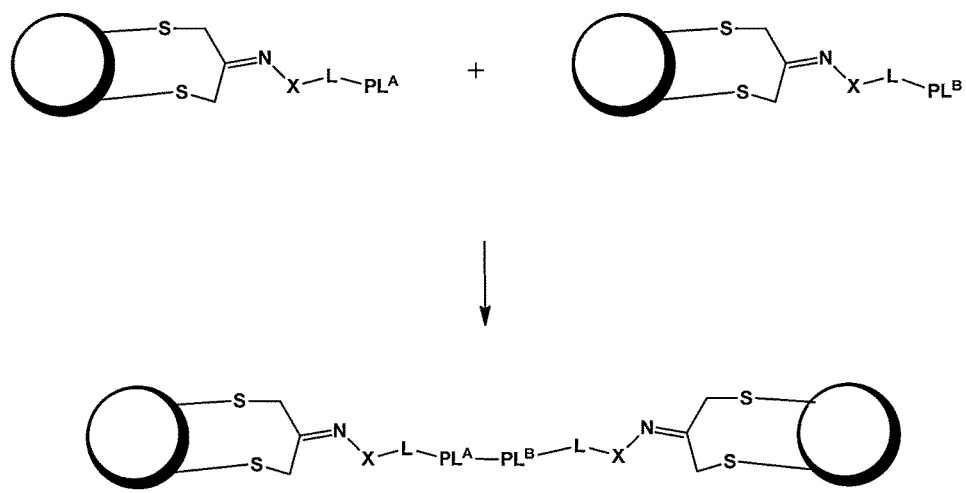
$PL^A$ and $PL^B$ are complementary coupling groups

SDS Page Gel Analysis of the site-defined azido compound bearing CRM197

1 – Ketone modified CRM-197
2 – Oxime modified CRM-197

Figure 6
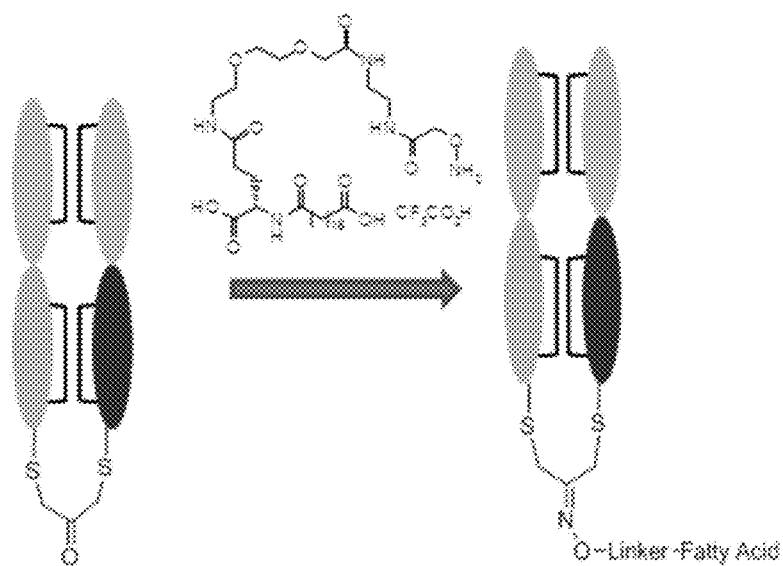
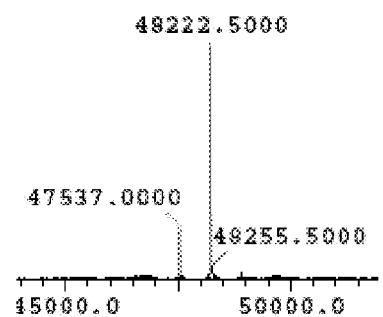

Figure 7.
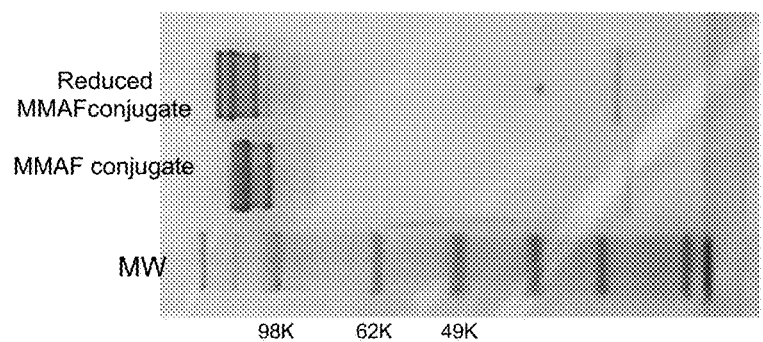
LC-MS of the product of Method B in Example 6.
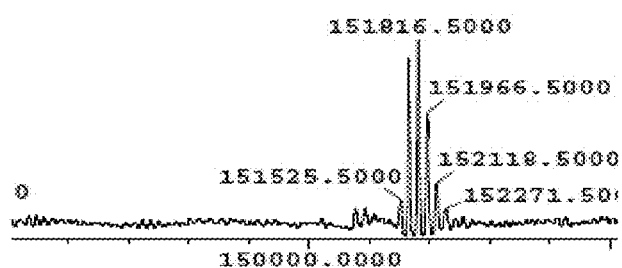

FIGURE 8.
Example 7, step 1:
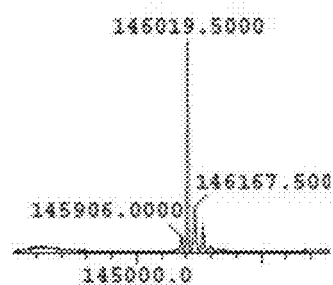
Example 7, step 2: PL1, Method A:
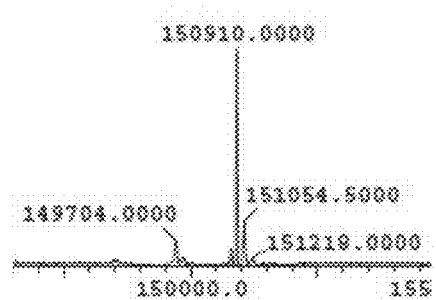
Example 7, step 2: PL2, Method B:
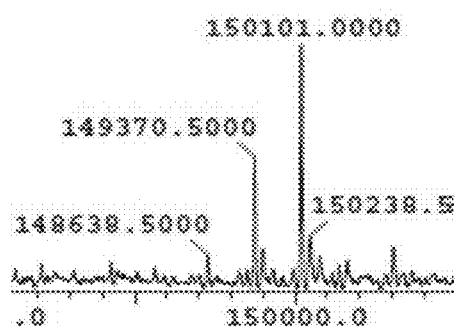

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Gly Phe Leu Gly
1

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle

<400> SEQUENCE: 2

Glu Arg Pro Arg Leu Cys His Lys Gly Pro Xaa Cys Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Cys(Trt)
<220> FEATURE:
<221> NAME/KEY: MOD_RES
<222> LOCATION: (7)..(7)
<223> OTHER INFORMATION: His(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Cys(Trt)

<400> SEQUENCE: 3

Glu Arg Pro Arg Leu Cys His Lys Gly Pro Xaa Cys Phe
1               5                   10

<210> SEQ ID NO 4
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: misc_feature
<222> LOCATION: (6)..(12)
<223> OTHER INFORMATION: Cyclic
<220> FEATURE:
<221> NAME/KEY: MOD_RES
<222> LOCATION: (11)..(11)
<223> OTHER INFORMATION: Nle
<220> FEATURE:
<223> OTHER INFORMATION: See specification as filed for detailed
      description of substitutions and preferred embodiments

<400> SEQUENCE: 4

Glu Arg Pro Arg Leu Cys His Lys Gly Pro Xaa Cys Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: misc_feature
<222> LOCATION: (6)..(12)
<223> OTHER INFORMATION: Cyclic
<220> FEATURE:
<221> NAME/KEY: MOD_RES
<222> LOCATION: (11)..(11)
<223> OTHER INFORMATION: Nle
<220> FEATURE:
<223> OTHER INFORMATION: See specification as filed for detailed
      description of substitutions and preferred embodiments

<400> SEQUENCE: 5

Glu Arg Pro Arg Leu Cys His Lys Gly Pro Xaa Cys Phe
1               5                   10
```

METHODS FOR OXIME CONJUGATION TO KETONE-MODIFIED POLYPEPTIDES

This application is a non-provisional of, and claims priority to U.S. Provisional Application No. 61/909,236, filed Nov. 26, 2013, and U.S. Provisional Application No. 62/002,614, filed May 23, 2014.

SEQUENCE LISTING

The instant application contains a Sequence Listing which has been submitted electronically in ASCII format and is hereby incorporated by reference in its entirety. Said ASCII copy, created on Nov. 9, 2015, is named PAT056023-US-NP_SL.txt and is 2,702 bytes in size.

BACKGROUND

A wide variety of chemical moieties ('payloads') have been covalently attached to enzymes, antibodies, and other large, polypeptides or proteins, to form conjugates. The payloads may be used to locate the protein to which they are attached (e.g., labels), to modify the physicochemical properties or stability of the protein (e.g., PEGylation), to enable the protein to be attached to another molecule or protein (coupling groups for connecting the conjugate to another compound or another conjugate), or to modify the function or activity of the payload or the protein (e.g., vaccine conjugates). The protein may also act as a carrier to deliver the attached payload to a particular tissue or cell type, such as in antibody-drug conjugates (ADCs). Classes of payloads that can be usefully linked to proteins include detectable moieties (labels), anchoring moieties to attach the protein to a surface or another compound, antigens that elicit an immune response when conjugated to a protein, coupling groups that react readily with a chemically complementary coupling partner (thus connecting the protein to another entity), and therapeutic moieties such as cytotoxins and other bioactive agents. Attaching these diverse structures to proteins in a controlled and reproducible fashion is often critical for the conjugates to function correctly. Thus there is a need for a variety of methods to attach many types of payloads to many different proteins or polypeptides.

A number of methods have been developed for attaching payloads to proteins to form protein conjugates. See, e.g., Sletten, E. M. and Bertozzi, C. R. *Angew. Chem. Int. Ed.* 2009, 48, 6974-6998; Baslé, E.; Joubert, N.; and Pucheault, M. *Chemistry & Biology* 2010, 17, 213-227. In some protein conjugates, the method by which the protein and payload are connected may have undetectable impact on the activity or relevant properties of the conjugate; in other instances, the nature of the linkage between protein and payload can significantly affect the activity or properties of the conjugate. Sometimes it is critical to control the number of payload moieties per protein, for example, or to control the precise location where payloads are attached so they do not interfere with functions of the protein. ADCs, for example, require the protein to recognize and bind to surface structures on targeted cells to impart selectivity, so a payload must not be positioned to interfere with binding of the antibody to the surface structures (antigen) that the antibody must recognize. See, e.g., *Expert Opin. Biol. Ther.* 2012, 12, 1191-1206; *Toxins* 2011, 3, 848-883; and Laurent Ducry *Drug Delivery in Oncology: From Basic Research to Cancer Therapy*, 1st Edition. Wiley-VCH Verlag GmbH & Co. KGaA. 2012, 12, 355-374.

Most methods for attaching payloads to proteins involve adding a linking chemical structure (linker) between the protein and the particular payload of interest. The linker provides a way to connect the payload of interest to the protein using available functional groups on each moiety. The linker often allows the distance between payload and protein to be modulated, and may also include a cleavable portion that can be lysed or degraded in vivo to release the payload from the protein where release is important for the payload to achieve its objectives. For example, in ADCs, it may be critical for the conjugate to break down and release the payload at a location where it can have a desired effect. Because of the diverse types of protein-payload conjugates that place different demands on the manner in which the payload and protein are connected, there is a continuing need for novel methods to link payloads to proteins consistently and efficiently.

The most common methods for forming protein conjugates rely upon the chemical reactivity of certain amino acids that occur naturally in many natural proteins: lysine and cysteine are often used because they provide a reactive site for connecting the payload to the protein. Lysine has a free amine group that can react with a suitable electrophilic functionality on a linking group or payload, and cysteine can react through its free sulfhydryl group. However, relying on these naturally occurring reactive sites can be complicated: when there are too many or too few of the particular type of amino acid in a protein of interest, for example, it becomes difficult to get just the right 'loading' of payload on the protein. The high abundance of lysine on protein surfaces makes site- and regio-selective conjugation difficult, and leads to heterogeneous products. In contrast, cysteines are comparatively rare, and exist mainly in disulfide-linked pairs in proteins. Conjugation at cysteine often requires reduction of a disulfide, followed by reaction with a conjugation reagent (e.g. maleimide) to label individual cysteines separately. Because this removes a disulfide linkage, the protein structure and stability might be undermined by this process.

Proteins also often have more lysines than the optimum number of payloads to be attached: adding enough payload moieties to occupy all of the availably lysines in order to ensure a consistent, homogenous product may add too many payload molecules for optimum efficacy. This can be avoided by using only some of the lysines for conjugation, but such partial or incomplete loading will generally provide a heterogeneous product, which can be problematic for a variety of reasons—in the case of Mylotarg™, the first commercialized ADC, for example, the heterogeneity of the ADC product seems likely to have contributed to the issues that led to a decision to withdraw the product from registration. Fuenmayor, et al., *Cancers, vol.* 3, 3370-93 (2011). Also, even when enough amino acid groups of a particular type (e.g., lysines) are present for optimal loading, some or all of them may be 'buried' inside the protein when the protein is in its solution conformation, rendering them effectively unavailable for conjugation, or making them 'partially' accessible which can also result in heterogeneity of the conjugate. Thus, while lysine can be a useful site for conjugation, in many situations it is not ideal.

The frequency of occurrence of cysteine in natural proteins is lower than that of lysine, and cysteine may be suitable for use as a site for conjugation where it is available in adequate numbers; where too few cysteines are present, one or more may be inserted by standard protein modification methods. However, it is often preferable to avoid modifying the sequence of the natural protein by inserting a cysteine; besides, surface-accessible cysteines in natural proteins are often positioned near other cysteines to form disulfides, which may be important for maintaining the protein's active conformation. While it is not difficult to convert a disulfide into two free cysteines by reducing the disulfide, doing so may disrupt the secondary or tertiary structure of the protein.

Some methods for attempting to insert a tether between cysteine residues formed by reducing a disulfide on a protein have been reported. One such method involves a sulfone-substituted methacrylate derivative. US2006/0210526. This method forms a reactive intermediate that requires an elimination step before cyclization, and the conditions for that multi-step process can result in incomplete formation of a linker (tether) between cysteines, and the reaction conditions can even cause protein denaturation. Another approach uses a maleimide derivative. WO2011/018613. However, the conjugate formed in this process suffers from stability problems because the Michael addition of the thiols on the maleimide is reversible. There is thus a need for improved methods to conjugate chemical moieties to proteins containing disulfide linkages to form protein conjugates. In particular, methods are needed that use the disulfide components (sulfhydryls) without giving up the conformation controlling effect of the disulfide, while also providing efficient conjugation, stability, and consistent payload/protein ratios. In addition, there is a need for stapling methods to hold proteins in a particular conformation (see, e.g., *Expert Opin. Drug Discov.* (2011) 6(9):937-963; *Tetrahedron* 55 (1999) 11711-11743) that also provide a means to conjugate the stapled protein with a payload. The present invention provides such methods, including improved methods for forming an oxime between a ketone-modified protein or polypeptide and an alkoxyamine compound.

SUMMARY

The invention provides improved methods for conjugation of a ketone-modified polypeptide or protein with an aminooxy compound (an alkoxyamine or aryloxyamine, for example) to form an oxime-modified polypeptide or protein as illustrated in the reaction below. The method involves selection of conditions that promote highly efficient oxime formation, providing higher yields of oxime and more complete oxime formation; the result is an improved yield of oxime formation and, for a polypeptide or protein having two or more ketone modifications, improved product homogeneity. The method comprises use of an amine or amine salt as a promoter, typically in a buffer at pH 3-8. Commonly, the promoter or the buffer or both will contain a carboxylic acid, e.g., an acetate or benzoate buffer can be used. Optionally, the amine can be used as a carboxylate salt, or it may be a carboxy-substituted amine compound that may be zwitterionic. Aniline, aminobenzoic acid, 3,5-diaminobenzoic acid, hydrazines, and 3,5-dicarboxyaniline are suitable amines for use in these methods.

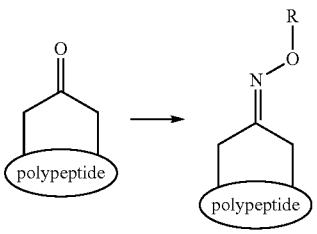

In a preferred embodiment, the ketone-modified polypeptide and the oxime are of the formulas shown below, wherein the sulfur atoms are from cysteine groups in the polypeptide:

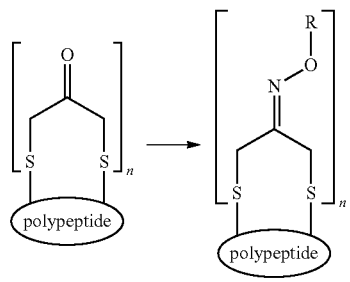

where n is 2-8, preferably 2 or 4, and n indicates the number of ketone modifications or oximes derived from ketone modifications that are present on the polypeptide. The polypeptide may be an antibody or antibody fragment, where the two sulfur atoms are derived from interchain disulfide bonds of the polypeptide. Because the improved methods increase efficiency of oxime formation, they are particularly useful in peptides where n is more than one, because they improve the homogeneity of the conjugation product. In antibodies, especially, where there are typically four disulfides available for ketone modification, the improved methods increase the yield of conjugation products such as an antibody-drug conjugate (ADC) having 4 payload groups per antibody molecule (DAR=4). The importance of homogeneity in ADCs is well established, as exemplified by the Mylotarg™ story, where inhomogeneity is believed to have contributed to withdrawal of the first US FDA approved ADC from the market.

In one aspect, the invention provides a method to use two cysteine residues that form a disulfide on a protein's surface to link a payload to the protein, forming a protein conjugate. The method involves reducing the disulfide to provide two free thiol groups, and tying the two thiol groups together with a tether that keeps them in about the same positions they occupied when they formed a disulfide. Keeping the cysteine groups in their same approximate positions minimizes any adverse effect on the protein's conformation that may occur upon reduction of the disulfide. The tether that is introduced to link the two thiol groups together contains a reactive functional group that can be used to attach a payload of interest. In some embodiments, the tether contains a carbonyl group that is reactive enough to form an imine or oxime or hydrazone linkage with an external amine group, and the payload is conjugated to the activated protein by forming such linkage. For example, the reduced protein can be reacted with a 1,3-dihalo acetone such as dichloroacetone or dibromoacetone, thereby inserting a 3-carbon tether connecting the two sulfur atoms together. This may suitably simulate the effect of the disulfide, i.e., to keep the protein in a conformation very similar to the one it had when the disulfide was present, while it also provides greater stability than the disulfide as well as a place to attach a payload. The tethers used in the methods and compositions of the invention provide a chemically reactive functional group, and a protein containing this type of tether between two cysteine sulfur atoms is referred to herein as an activated protein. A preferred tether is the ketone linker obtained by reacting the reduced disulfide group with 1,3-dichloroacetone, i.e., —CH$_2$—C(O)—CH$_2$—. A payload can be attached to the activated protein using the functional group on the tether.

The tether formed by reacting the thiols of a protein with a dihaloacetone provides a carbonyl as a site for conjugation, for example. A payload containing a suitable amine (aminated payload), preferably an aminooxy of formula R—O—NH$_2$ as further described herein, can easily be conjugated to such an activated protein by forming an oxime between the aminooxy functionality of the payload and the carbonyl group (ketone) of the tether. In a preferred embodiment, the activated polypeptide or protein having a ketone inserted between two cysteine residues is contacted with an alkoxyamine (RONH$_2$) in the presence of an amine promoter, where the alkoxy group (R) comprises a payload such as a therapeutic agent or a reactive group capable of use to attach a therapeutic agent. Suitable amine promoters include aniline or an anilinium salt (e.g., anilinium acetate, anilinium benzoate, and the like), acylhydrazines (e.g., acetyl hydrazine), or an aminobenzoic acid such as PABA, 3-aminobenzoic acid, 3,5-diaminobenzoic acid, 3,5-dicarboxyaniline, and the like. Suitable reaction conditions to promote efficient oxime formation are provided herein.

These methods can be applied to any protein having one or more accessible disulfide linkages, and are typically useful for natural proteins having a molecular weight above 500 Da and typically above 2,000 Da, where a disulfide is present in the native or active form of the protein. They can be used with proteins containing more than one disulfide, such as 2-10, or typically up to 6 disulfide groups, at least one of which is surface accessible sufficiently to be reduced by conventional disulfide reducing agents. These methods produce a conjugate containing at least one payload for each disulfide group that is utilized, and the tether substantially retains the native or active conformation of the protein.

In another embodiment, the invention provides a way to staple a protein by tying two cysteine residues together, providing a rigidified conformation, wherein the stapling method ties two cysteines together with a ketone-containing linkage that is then usable for conjugating the stapled protein to a payload. Stapling is accomplished by reacting a protein containing at least two cysteine residues with a dihaloketone such as 1,3-dichloroacetone or 1,3-dibromoacetone to form a cyclized protein containing an [cys1]-S—CH$_2$—C(VO)—CH$_2$—S-[cys2] linkage, then allowing the linkage to react with an aminooxy compound of the formula H$_2$N—O-L-PL to form a conjugate via oxime formation as further described herein. The invention provides improved methods of making these stapled conjugated peptides.

BRIEF DESCRIPTION OF THE DRAWINGS

FIG. 2 illustrates coupling of two protein-payload conjugates having complementary coupling groups, PL$^A$ and PL$^B$, as their payloads.

FIG. 6 shows a schematic depiction of a protein-payload conjugate described in Example 4 and LC-MS data for the product.

FIG. 7 shows a gel of the conjugate and reduced conjugate of Example 6, Method A, accompanied by a molecular weight ladder for comparison. It also shows the LC-MS of the product of Method B, showing formation of several different conjugates.

FIG. 8 shows LC-MS data for products of Step 1; Step 2, Method A (PL1); and Step 2, Method B (PL2) from Example 7.

DETAILED DESCRIPTION OF EMBODIMENTS OF THE INVENTION

Figure 1:
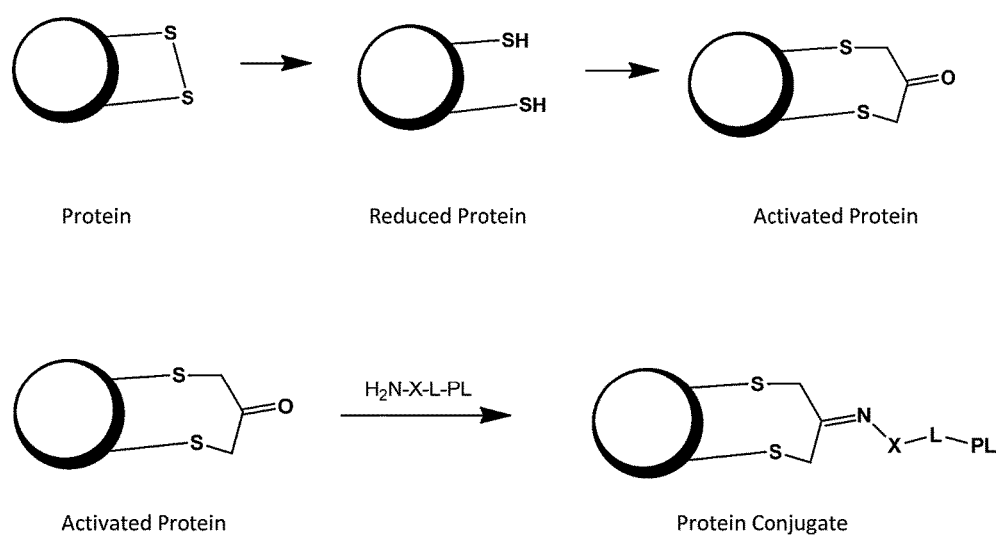
FIG. 1 is a scheme illustrating an application of the invention (when X is O) that begins with a disulfide-containing protein and is converted to a reduced protein, an activated protein and provides a protein-payload conjugate.

'Protein' and polypeptide as used herein refer to peptides containing five or more, typically ten or more amino acid residues connected by amide (peptide) bonds. Typically the proteins described herein comprise mainly or only naturally occurring amino acids, though the methods are equally useful with polypeptides that contain one or more non-natural amino acids. Commonly (but not necessarily) the amino acids are mostly or entirely of the L configuration and are selected from the common 'essential' amino acids.

Abbreviations
DAR Drug to Antibody Ratio
DCM Dichloromethane
DIC Diisopropyl Carbodiimide
DIPEA Diisopropyl Ethyl Amine
EDT Ethane dithiol
HBTU N,N,N',N'-Tetramethy-O-(1H-benzotriazol-1-yl) uronium hexafluorophosphate
MeCN acetonitrile
NMP N-methyl pyrrolidinone
PBS Phosphate-buffered saline
TCEP Tris(carboxyethyl)phosphine
TFA Trifluoroacetic acid
TIPS Triisopropyl silane The invention provides improved conditions for the oxime formation when conjugating a ketone-modified polypeptide with a substituted alkoxyamine. The improved conditions use an amine promoter to facilitate oxime formation: aniline can be used, but substituted anilines, particularly carboxy-substituted anilines such as those disclosed herein are more suitable. Acylhydrazides such as acetylhydrazine or benzoylhydrazide can also be used. The amine promoter can be added as a free amine, or as an amine salt having any suitable counterion; in some embodiments, a carboxylate counterion is preferred, such as acetate or citrate. Typically, an excess of the amine promoter is used.

The reaction is typically run in a buffer at pH 3-8, preferably pH 4-8. Various buffers can be used including PBS, Tris, sodium phosphate, acetate, formate, citrate, and the like to maintain a suitable pH. Suitable polypeptide concentrations for the reaction are higher than conventionally used concentrations: in some embodiments, the polypeptide concentration is at least 1 mg/mL, or at least 2 mg/mL, and is preferably about 5 mg/mL or higher, up to a concentration where solubility is compromised, e.g. up to about 25 mg/mL.

The reaction is typically performed at a temperature suitable for maintaining the structure and function of the polypeptide; the temperature is commonly between 4 and 70° C., preferably between 10 and 30° C. Reaction times of 0.5 to 48 hours may be used: an adequate reaction time can readily be determined by monitoring progress of the reaction by known methods. At a temperature between about 4° C.

and about 25° C., a reaction time of less than one hour to about 4 hours is generally sufficient.

In some embodiments, the method comprises reducing a disulfide of a polypeptide in the presence of 1,3-dichloroacetone. Data provided herein demonstrates that adding dichloroacetone to a buffered solution of the polypeptide before addition of the reducing agent that opens the disulfide bond unexpectedly provides substantial improvement in product yield. Having the dichloroacetone present when the disulfide reduction is initiated is particularly important when more than one disulfide bond is reduced on a polypeptide. For example, when the polypeptide is an antibody, reduction with TCEP reduces four inter-chain disulfide bonds, allowing the reaction with dichloroacetone to introduce four ketone-containing tethering groups. When the reaction was conducted by first adding TCEP to initiate the reduction step before dichloroacetone was added, yield of fully modified antibody was about 33-35% (pH 8.0, 50 mM TRIS as buffer, ambient temperature). About 50% of the polypeptide product contained a heavy chain fragment covalently linked to a light chain fragment. When 1,3-dichloroacetone was preincubated with polypeptide substrate prior to the addition of TCEP under the same conditions, the yield of fully modified antibody increased to 75-77%. The product composition for these reactions was assessed by microchip electrophoresis SDS method (ref: Electrophoresis 2012, 33, 765-772.) Detection of HC—HC, HC-LC, and HC—HC-LC fragments indicates partial modification to the covalently tethered product of interest (one or two of the inter-chain disulfides have been replaced by the dichloroacetone-derived tether), and 'Intact' antibody corresponding to $(HC)_2$ $(LC)_2$ corresponds to fully-modified tetrameric antibody having each of the inter-chain disulfides replaced by a dichloroacetone-derived tether.

An example of an application of the invention is shown in FIG. 1. The Figure depicts a protein, represented as a circle and having an exposed disulfide group. The disulfide is reduced, forming a reduced protein having two free thiols derived from the disulfide. The reduced protein is then allowed to react with a dihaloacetone or similar bis-electrophile (e.g., 1,3-dichloroacetone or 1,3-dibromoacetone) to form an activated protein wherein the two thiols are linked together through a functionalized tether: the tether in this example contains a ketone group that is relatively reactive toward Schiff base formation. A payload molecule is then linked to the tether of the activated protein via a Schiff base formation to provide a protein conjugate. The payload in the example is attached via a linking group to the tether. The compound of the formula $H_2N$—X-L-PL where PL is the payload compound contains an activated amine group ($H_2N$—) that is connected to PL by a linker L, and the amine is made especially reactive by using an aminooxy or similar activated amine, —X—$NH_2$ where X is O, which facilitates Schiff base formation between the ketone carbonyl and the amine attached to PL. An alternative embodiment begins with a protein having two free cysteine groups, such as the reduced protein in FIG. 1, and uses them to 'staple' the protein into a constrained conformation while also providing an attachment point for a payload to be conjugated onto the stapled protein.

The methods of the invention are suitable for use with any ketone-modified polypeptide, but are especially useful to form conjugates from proteins that contain at least one disulfide linkage between two cysteines, or that contain two free cysteine residues that can be connected together by reaction with a 1,3-dihaloacetone reactant. Typically, the protein is one where the two thiols react with dichloroacetone or dibromoacetone under conditions described herein to produce at least 50% cross-linking of the two thiols, and frequently the extent of cross-linking is at least about 70%, 80% or 90%.

The two cysteines to be linked together may be on a single polypeptide, or they may be on separate polypeptides that form a protein complex. In certain embodiments, the methods utilize a protein having 1-6 disulfide linkages, or 2-6 free cysteine residues, and involve reduction of at least one of these disulfides. The disulfide-containing protein can be any polypeptide having at least 5 amino acid residues, preferably at least 10 amino acids, that contains a disulfide linkage within a single polypeptide sequence, or a protein complex where a disulfide connects one polypeptide sequence to another amino acid or polypeptide, provided the complex does not dissociate rapidly when the disulfide is reduced for insertion of the tether between the sulfur atoms. Typical proteins for use in the methods of the invention include cyclic peptides and linear peptides containing about 5 to about 5000 amino acids, typically at least 10 amino acids and up to about 1000, including functional proteins such as enzymes or receptors; protein complexes having at least one disulfide linkage (often connecting two separate polypeptide strands); structural proteins; proteins used as vaccine scaffolds such as CRM197 or other proteins having adjuvant activity; and antibodies or antibody fragments. Particularly useful proteins for these methods include antibodies, especially monoclonal antibodies including engineered antibodies, modified antibodies and antibody fragments; vaccine carrier proteins such as CRM197; and single-stranded proteins having at least one disulfide linkage or at least two cysteine residues and having a molecular weight between 500 and 500,000, typically between 1,000 and 200,000. Methods for engineering an antibody or other protein to introduce one or more cysteine residues, for example, and for modifying antibodies are well known in the art.

The methods are especially useful with antibodies and antibody variants that have at least two interchain disulfides, including IgG and Fc. The methods are also useful with vaccine carrier proteins such as diphtheria toxoid, non-toxic cross-reactive material of diphtheria toxin (197) (CRM197), tetanus toxoid, keyhole limpet hemocyanin, *N. meningitidis* outer membrane protein, and non-typeable H. influenza-derived protein D. These vaccine carrier proteins can be functionalized with antigens by known methods and/or by the methods disclosed herein. The present methods can also be used to attach an adjuvant compound such as a TLR agonist (a ligand of TLR3, TLR4, TLR5, TLR7, TLR8, or TLR9) including imiquimod, imidazoquinolines, and gardiquimod, PRR ligands, RLR ligands, NOD2 ligands, cyclic di-AMP, cyclic di-GMP, flagellin, monophosphoryl lipid A, N-glycolated muramuldipeptide, CpG oligodeoxynucleotides (CpG ODN), triacylated lipoprotein, or poly (I:C), to provide an enhanced immune response.

The disulfide linkages of disulfide-containing proteins for use in the methods and compositions of the invention are reduced to form two free thiol groups: methods for such reduction are well known in the art. In some embodiments, the reduction is performed using a reducing agent that selectively reduces disulfide linkages that are readily accessible to solvent around the protein: one suitable reducing agent is tris(2-carboxyethyl)phosphine (TCEP) and its salts—see *Analytical Biochemistry* 273, 73-80 (1999). Other known disulfide-reducing agents such as dithiothreitol, 2-mercaptoethanol, cysteamine, and dithiobutylamine (J M Perkel, *Chem. Eng'g News*, Feb. 29, 2012; Lukesh, et al., *J. Am. Chem. Soc.*, 134, 4057-59 (2012)) and trialkyl phosphines such as tributyl phosphine (WO2008/157380) can also be used. Methods for reducing disulfides in proteins are well known in the art.

The linking group L can be any suitable organic linkage that connects the payload compound to —X—NH$_2$, where X represents O Some examples of suitable linkages include [X]—(CH$_2$)$_{1-6}$—[PL]; [X]—CH$_2$C(=O)—[PL]; [X]—CH$_2$C(=O)—NH—[PL]; [X]—CH$_2$C(=O)—O—[PL]; [X]—(CH$_2$CH$_2$O)n-[PL]; [X]-Phenyl-C(O)NH—[PL], [X]—(CH$_2$)$_{1-10}$—C(=O)—NH—(CH$_2$)$_{2-10}$—NH—C(=O)—(CH$_2$)$_{0-10}$—(OCH$_2$CH$_2$)$_{0-10}$-(AA)$_{0-10}$-[PL] (AA can be any of the essential amino acids, e.g. glu, gly, ala, asp, etc.), and the like, where n is typically 1-20, and [X] and [PL] respectively indicate which end of the linker is attached to X and which to PL. In some embodiments, the linker L can have two or three payloads attached to increase payload loading on the conjugate, and where more than one payload is attached to a given linker the payloads can be the same or different. Suitable linkers also include combinations of the components of these groups: the nature of the linker is not important to the practice of the invention and can be based on convenience and availability of methods for attachment to at least one payload PL, or on desired physicochemical properties for the conjugate. Selection of a suitable linker is within the level of ordinary skill and depends on the structure of the Payload and available methods for modifying it to attach linker L. Typically the linker is attached at one or both ends via an amide or ester group; frequently the linker L contains a peptide bond or ester to allow in vivo lysis by protease or esterase activities (for example val-cit, a dipeptide that is cleaved by cathepsin B, or Gly-phe-leu-gly (SEQ ID NO: 1), which is also cleavable by cathepsin B); optionally it contains one or more ethylene oxide units (—OCH$_2$CH$_2$—); and in many embodiments it contains at least one and up to six amino acid moieties. Suitable embodiments of L may also comprise one or more spacers, which may be selected from the following groups:

(a) a bond, —O—, —S—, —S—S—, —NH—, —N((C$_1$-C$_6$)alkyl)-, —NH—C(O)—NH—, —C(O)—NH—, —NH—C(O)—;

(b) (C$_1$-C$_{20}$)alkylene, (C$_2$-C$_{20}$)alkenyenne, (C$_2$-C$_{20}$)alkynylene, —Z—(C$_1$-C$_{20}$)alkylene-, —Z—(C$_2$-C$_{20}$)alkenylene, —Z—(C$_2$-C$_{20}$)alkynylene, (C$_1$-C$_{20}$)alkylene-Z—(C$_1$-C$_{20}$)alkylene, (C$_2$-C$_{20}$)alkenylene-Z—(C$_2$-C$_{20}$)alkenylene, (C$_2$-C$_{20}$)alkynylene-Z—(C$_2$-C$_{20}$)alkynylene, where Z is —NH—, —N(C$_1$-C$_6$)alkyl)-, —NH—C(O)—NH—, —C(O)—NH—, —NH—C(O)—, (C$_3$-C$_7$)cycloalkylene, phenylene, heteroarylene, or heterocyclene and where said (C$_1$-C$_{20}$) alkylene, said (C$_2$-C$_{20}$)alkenylene, and said (C$_2$-C$_{20}$) alkynylene moieties each independently optionally contain one or more oxygen atoms interdispersed within said moieties, such that the oxygen atoms are separated by at least one and preferably two carbon atoms;

(c) (C$_3$-C$_7$)cycloalkylene, (C$_3$-C$_7$)cycloalkylene-Y—(C$_3$-C$_7$)cycloalkylene, —Y—(C$_3$-C$_7$)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is (C$_1$-C$_{20}$) alkylene, (C$_2$-C$_{20}$)alkenylene, (C$_2$-C$_{20}$)alkynylene, —O—, —C(O)—, —S—, —NH—, —N((C$_1$-C$_6$) alkyl)-, —NH—C(O)—NH—, —C(O)—NH—, or —NH—C(O)— and where said (C$_3$-C$_7$)cycloalkylene, said phenylene, said heteroarylene, and said heterocyclene moieties are each individually optionally substituted with 1 to 3 substituents selected from halo, (C$_1$-C$_4$)alkyl or halo-substituted (C$_1$-C$_4$)alkyl;

(d) —[OCH$_2$CH$_2$]$_v$—, where v is 1-2,000, preferably 1-10; and (e) a peptide comprising 1 to 100 amino acids, preferably 1-30 or 1-6 amino acids;

(f) a multivalent linker capable of carrying 2, 3, 4, 5, or 6, or 2-10, payload moieties.

Furthermore, L can be or can comprise a cleavable linker such as Val-Cit (valine-citrulline, a dipeptide that is selectively cleaved by cathepsin B) or val-cit-PABC (valine-citrulline p-aminobenzylcarbamate, see *Bioconjugate Chem.* 19(10), 1960-63 (2008)), a disulfide, or a linker cleaved by glucuronidase, such as the linker present in this formula:

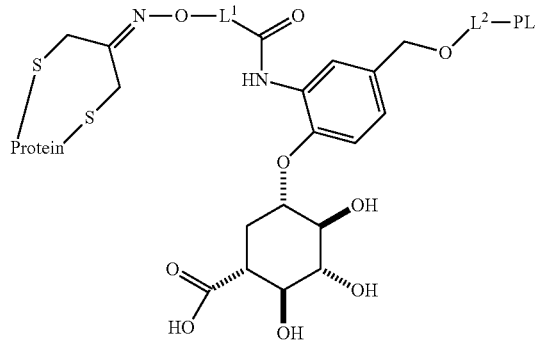

where Protein represents a protein for conjugation, PL represents a Payload as described herein, and L$^1$ and L$^2$ are independently optional linkers such as the groups L described above. (*ACS Med. Chem. Letters*, vol. 1, 277-280 (2010).

The Payload (PL) can be any moiety that is useful to attach to a protein. Many examples of compounds that can be usefully attached to proteins are known in the art. Examples include label moieties that enable a user to locate or identify the protein, including chelators that bind metal ions to provide detectability of the conjugate; binding moieties such as biotin or avidin, polynucleotides, antibodies or fragments thereof, poly-Arg or poly-lys containing 5-15 amino acid residues, etc., that make it easy to purify or isolate the protein or affix it to a surface; property-modifying groups such as fatty acid groups or polyethylene glycol (PEG); antigenic groups such as polysaccharides or cell surface proteins that are characteristic of a particular type of cell or bacterium; coupling groups that enable the modified protein or peptide to be attached to another molecule to make more complex conjugates, such as bispecific antibodies (see FIG. 2); and bioactive compounds including nucleic acids like RNA, DNA, mRNA, siRNA, and fragments of these; pharmaceutical compounds such as various therapeutic drugs; and radionuclides and cytotoxins, which can hitchhike on the protein to a desired tissue or cell where they can produce a desired effect. These hitchhiking compounds may act while they remain conjugated to the protein or a portion thereof, or they may first detach from the protein if the linking group is one that can readily cleave in vivo. Suitable pharmaceutical payloads for use with these methods include microtubule inhibitors, topoisomerase I inhibitors, intercalating agents, inhibitors of intracellular signaling pathways, kinase inhibitors, transcription inhibitors such as siRNAs, a RNAs, and miRNAs, and DNA minor groove binders; these payloads include compound classes such as maytansinoids, auristatins, amanitins, calicheamycins, psymberins, duocarmycins, anthracyclins, camptothecins, doxorubicins, taxols, pyrrolobenzodiazepines, and the like.

Specific examples of these pharmaceutical payloads having therapeutic or diagnostic uses include paclitaxel, docetaxel, etoposide, tenoposide, vincristine, vinblastine, colchicine, doxorubicin, daunorubicin, mithramycin, actinomycin, glucorticoids, puromycin, epirubicin, cyclophosphamide, methotrexate, cytarabine, f-fluorouracil, platins, streptozotocin, minomycin C, anthracyclines, dactinomycin or actinomycin, bleomycin, mithramycin, anthramycin, duocarmycins, ifosfamide, mitoxantrone, daunomycin, carminomycin, animoterin, melphalan, esperamicins, lexitropsins, auristatins (e.g., auristatin E, auristatin F, AEB, AEVB, AEFP, MMAE, MMAF), eleuthorobin, netropsin, podophyllotoxins, maytansiods including maytansine and DM1, and combretestatins.

Suitable coupling groups that can be used as payloads (groups that can be used to couple the conjugate to another moiety) include maleimide, thiols, alpha-halo ketones (e.g., —C(=O)—CH$_2$—X where X is chloro, bromo or iodo), carboxylic acids, amines, hydroxyls, alkenes, alkynes including cyclic octynes that can be used in copper-free 'click' chemistry, azide, and the like. Methods to use these coupling groups to connect the conjugates of the invention to other compounds having complementary coupling groups are well known in the art, and include Michael addition of a thiol to a maleimide, alkylation of a thiol with an alpha-haloketone, amide bond formation between amine and a carboxylic acid, 'click' chemistry (see, e.g., Meldal, et al., Chem Rev., vol 108, 2952-3015 (2008)) to link an azide to an alkyne by forming a 1,2,3-triazole ring, and 'copper-free click' chemistry. See e.g., Meeuwissen, et al. Polymer Chemistry, vol. 3, 1783-95 (2012). 'Complementary' coupling groups are two coupling groups that readily combine to form a covalent bond, such as the pairs mentioned above (carboxylate plus amine to form an amide; azide plus alkyne to form a 1,2,3-triazole; maleimide plus thiol, where the thiol adds to the double bond via a Michael addition; alpha-halo ketone plus thiol which form an alpha-thio ketone by alkylation of the thiol; etc.) A depiction of a conjugate containing a coupling group as payload being coupled with a second conjugate containing a complementary coupling group is provided in FIG. 2. In particular examples, a coupling group to serve as a Payload (PL) is selected from the group consisting of halogen, —C≡CH, —C=CH$_2$, —OH, —SH, —SO$_2$—CH=CH$_2$, —O—NH$_2$, —N$_3$, —O—P(O)(OH)$_2$, —C(O)—H, —C(O)—CH$_3$, —NH—C(O)—CH$_2$—I, maleimidyl, 3,5-dioxo-1,2,4-triazolidin-4-yl, 1H-pyrrole-2,5-dione-1-yl, pyridin-2-yl-disulfanyl, tetrahydro-1H-thieno[3,4-d]imidazol-2(3H)-one-4-yl, 1-carbonyloxy-2,5-dioxopyrrolidine, sodium 1-carbonyloxy-2,5-dioxopyrrolidine-3-sulfonate, —SSR$^1$, —C(O)—OR$^1$, —N(R$^1$)H, —NH—N(R$^1$)H, where R$^1$ is H or (C$_1$-C$_6$)alkyl, and —C(O)—R$^2$, where R$^2$ is H, (C$_1$-C$_4$) alkyl, halo-substituted (C$_1$-C$_4$)alkyl, —CH=CH$_2$, N(R$^1$)H, or —NH—N(R$^1$)H. When these Payloads are used as an initial payload (PC), the conjugate can be reacted with a compound comprising a second payload (PL$^b$), and may introduce an additional linker L' in forming a new conjugate:

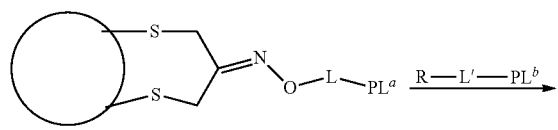

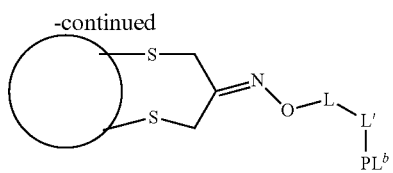

PL$^a$ is coupling group, e.g. maleimide, protected thiol, N$_3$, alkyne
R is the complementary reactive group for PL$^a$
PL$^b$ is a new payload, such as a label or biologic, including proteins, antibody, si-RNA, toxins etc.

Note that in these reactions, the person of skill in the art will understand that the L and L' may retain a portion of PC and/or R, depending upon the reaction being used to connect the new Payload, PL$^b$.

The following enumerated embodiments illustrate particular aspects of the invention.

1. A method to convert a ketone-modified polypeptide into an oxime-modified polypeptide, wherein the method comprises contacting the ketone modified polypeptide with a group of the formula R—O—NH$_2$ in the presence of an amine promoter.
2. The method of embodiment 1, wherein the amine promoter is aniline, a substituted aniline including 3,5-diaminobenzoic acid or 3,5-dicarboxyaniline, or an acyl hydrazide such as acetyl hydrazide.

In one embodiment of these methods, the ketone modified polypeptide is formed from a disulfide by reducing the disulfide to form two free thiols; and the free thiols are linked together by reaction with 1,3-dichloroacetone or 1,3-dibromoacetone. In a particular embodiment of this method, a polypeptide having a reducible disulfide bond is contacted with a reducing agent such as, but not limited to, TCEP and 1,3-dichloroacetone in a buffer, such as but not limited to TRIS or PBS. Preferably, the polypeptide and buffer are combined with 1,3-dichloroacetone before the reducing agent is added, so that 1,3-dichloroacetone is present as the reduction occurs.

3. The method of embodiment 1 or 2, wherein the group of Formula R—O—NH$_2$ is a compound of the formula H$_2$N—O-L-PL where L represents a Linker, and PL represents a Payload group.
4. The method of embodiment 1, wherein the ketone-modified polypeptide is of the formula

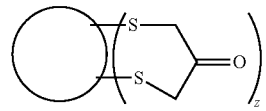

where the circle represents the polypeptide, and each sulfur atom is the sulfhydryl of a cysteine residue of the polypeptide, and z is an integer from 1 to 10.
5. The method of any of the preceding embodiments, wherein the Protein-Payload conjugate is of the formula:

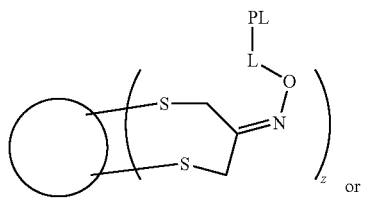

-continued

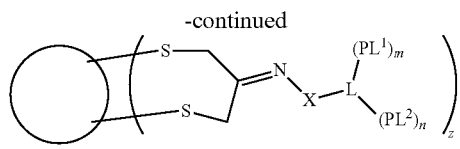

wherein X is O, L represents a Linker, and PL, $PL^1$ and $PL^2$ independently at each occurrence represent a Payload group, where m and n are each independently 1 to 10; z is 1-10, preferably 1-5, provided that m and n are not both 0.

6. The method of any of the preceding embodiments, wherein the polypeptide is an antibody (e.g. IgG, Fab or $F(ab)_2$, Fc).
7. The method of any of embodiments 1-5, wherein the polypeptide is a vaccine carrier.
8. The method of any of embodiments 1-8, wherein the Payload comprises a therapeutic agent.
9. The method of any of embodiments 1-7, wherein the Payload comprises a detectable label or a reactive group suitable for attaching a payload group that comprises a complementary reactive group.
10. The method of embodiment 8, wherein L comprises a cleavable linking moiety.
11. The method of any one of embodiments 1-10, wherein L comprises at least one spacer selected from:
(a) a bond, —O—, —S—, —NH—, —N(($C_1$-$C_6$)alkyl)H—, —NH—C(O)—NH—, —C(O)—NH—, —NH—C(O)—;
(b) ($C_1$-$C_{20}$)alkylene, ($C_2$-$C_{20}$)alkenylene, ($C_2$-$C_{20}$)alkynylene, —Z—($C_1$-$C_{20}$)alkylene-, —Z—($C_2$-$C_{20}$)alkenylene, —Z—($C_2$-$C_{20}$)alkynylene, ($C_1$-$C_{20}$)alkylene-Z—($C_1$-$C_{20}$)alkylene, ($C_2$-$C_{20}$)alkenylene-Z—($C_2$-$C_{20}$)alkenylene, ($C_2$-$C_{20}$)alkynylene-Z—($C_2$-$C_{20}$)alkynylene, where Z is —NH—, —N($C_1$-$C_6$)alkyl)-, —NH—C(O)—NH—, —C(O)—NH—, —NH—C(O)—, ($C_3$-$C_7$)cycloalkylene, phenylene, heteroarylene, or heterocyclene and where said ($C_1$-$C_{20}$) alkylene, said ($C_2$-$C_{20}$)alkenylene, and said ($C_2$-$C_{20}$) alkynylene moieties each independently optionally contain 1-10 oxygen atoms interdispersed within said moieties;
(c) ($C_3$-$C_7$)cycloalkylene, ($C_3$-$C_7$)cycloalkylene-Y—($C_3$-$C_7$)cycloalkylene, —Y—($C_3$-$C_7$)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is ($C_1$-$C_{20}$) alkylene, ($C_2$-$C_{20}$)alkenylene, ($C_2$-$C_{20}$)alkynylene, —O—, —C(O)—, —S—, —NH—, —N(($C_1$-$C_6$) alkyl)H—, —NH—C(O)—NH—, —C(O)—NH—, or —NH—C(O)— and where said ($C_3$-$C_7$)cycloalkylene, said phenylene, said heteroarylene, and said heterocyclene moieties are each individually optionally substituted with 1 to 3 substituents selected from halo, ($C_1$-$C_4$)alkyl or halo-substituted ($C_1$-$C_4$)alkyl;
(d) —[$OCH_2CH_2$]$_v$—, —X{$CH_2$[$OCH_2CH_2$]$_v$}$_w$— where v is 1-2,000, w is 1-4; X is C or N and
(e) a peptide comprising 1 to 100 amino acids; and
(f) Dendritic macromolecules, including dendrimers, dendrons, and hyperbranched polymers.
12. A method to convert a polypeptide comprising a reducible disulfide bond into a ketone-modified polypeptide that comprises a group of the formula [PP]—S—$CH_2$—C(=O)—$CH_2$—S—[PP], where each S is a sulfur from the disulfide bond, and [PP] indicates where the ends of the linking group are attached to the polypeptide,
wherein the method comprises forming a mixture of a polypeptide containing a reducible disulfide bond, an aqueous buffer, and 1,3-dihaloacetone, then adding a reducing agent capable of reducing the disulfide bond.
13. The method of embodiment 12, wherein the 1,3-dihaloacetone is 1,3-dichloroacetone.
14. The method of embodiment 12 or 13, wherein the reducing agent is a water-soluble phosphine or phosphine salt. TCEP is a suitable reducing agent.
15. The method of any of embodiments 12-14, wherein the polypeptide is an antibody or antibody fragment. Suitably, the polypeptide is an antibody, which may be monoclonal and may be humanized. Antibodies to antigens that are characteristic of cancer cells are suitable polypeptides.
16. A method to convert a ketone-modified polypeptide into an oxime-modified polypeptide, wherein the method comprises contacting the ketone modified polypeptide with a group of the formula R—O—$NH_2$ in the presence of an amine promoter and at a polypeptide concentration of at least about 1 mg/mL. Typically, R in these methods comprises a payload as described herein, and a linker. Suitable payloads include maytansinoids (e.g., DM1, DM4), auristatins (e.g., MMAE, MMAF), amanitins, calicheamycins, psymberins, duocarmycins, anthracyclins, camptothecins, doxorubicins, taxols, pyrrolobenzodiazepines, and the like.
17. The method of claim 5, wherein the ketone-modified polypeptide is made by the method of any of embodiments 12-16.
18. The method of embodiment 17, wherein the amine promoter is a carboxy-substituted aniline or an acyl hydrazine.
19. The method of any of embodiments 12-17, wherein the group of Formula R—O—$NH_2$ is a compound of the formula $H_2N$—O-L-PL where L represents a Linker, and PL represents a Payload group.
20. The method of embodiment 16, wherein the ketone-modified polypeptide is of the formula

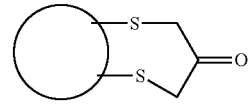

where the circle represents the polypeptide, and each sulfur atom is the sulfhydryl of a cysteine residue of the polypeptide.
21. The method of any of embodiments 16-20, wherein the Protein-Payload conjugate is of the formula:

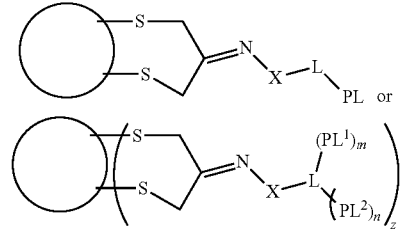

wherein X is O, L represents a Linker, z is an integer from 1 to 10, and PL, $PL^1$, and $PL^2$ independently at each occurrence represent a Payload group.

22. The method of any of embodiments 12-21, wherein the polypeptide is an antibody.

23. The method of any of embodiments 12-21, wherein the polypeptide is a vaccine carrier.

24. The method of any of embodiments 16-23, wherein the Payload comprises a therapeutic agent.

25. The method of any of embodiments 16-24, wherein the Payload comprises a detectable label or a binding group.

26. The method of embodiment 25, wherein L comprises a cleavable linking moiety.

27. The method of any one of embodiments 16-26, wherein L comprises at least one spacer selected from:
  (a) a bond, —O—, —S—, —NH—, —N(($C_1$-$C_6$)alkyl)-, —NH—C(O)—NH—, —C(O)—NH—, —NH—C(O)—;
  (b) ($C_1$-$C_{20}$)alkylene, ($C_2$-$C_{20}$)alkenylene, ($C_2$-$C_{20}$)alkynylene, —Z—($C_1$-$C_{20}$)alkylene-, —Z—($C_2$-$C_{20}$)alkenylene, —Z—($C_2$-$C_{20}$)alkynylene, ($C_1$-$C_{20}$)alkylene-Z—($C_1$-$C_{20}$)alkylene, ($C_2$-$C_{20}$)alkenylene-Z—($C_2$-$C_{20}$)alkenylene, ($C_2$-$C_{20}$)alkynylene-Z—($C_2$-$C_{20}$)alkynylene, where Z is —NH—, —N(($C_1$-$C_6$)alkyl)H—, —NH—C(O)—NH—, —C(O)—NH—, —NH—C(O)—, ($C_3$-$C_7$)cycloalkylene, phenylene, heteroarylene, or heterocyclene and where said ($C_1$-$C_{20}$)alkylene, said ($C_2$-$C_{20}$)alkenylene, and said ($C_2$-$C_{20}$)alkynylene moieties each independently optionally contain 1-10 oxygen atoms interdispersed within said moieties;
  (c) ($C_3$-$C_7$)cycloalkylene, ($C_3$-$C_7$)cycloalkylene-Y—($C_3$-$C_7$)cycloalkylene, —Y—($C_3$-$C_7$)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is ($C_1$-$C_{20}$)alkylene, ($C_2$-$C_{20}$)alkenylene, ($C_2$-$C_{20}$)alkynylene, —O—, —C(O)—, —S—, —NH—, —N(($C_1$-$C_6$)alkyl)H—, —NH—C(O)—NH—, —C(O)—NH—, or —NH—C(O)— and where said ($C_3$-$C_7$)cycloalkylene, said phenylene, said heteroarylene, and said heterocyclene moieties are each individually optionally substituted with 1 to 3 substituents selected from halo, ($C_1$-$C_4$)alkyl or halo-substituted ($C_1$-$C_4$)alkyl;
  (d) —[$OCH_2CH_2$]$_v$— or -J-{$CH_2$[$OCH_2CH_2$]$_v$}$_w$— where v is 1-2,000, w is 1-4, and J is $CH_2$ or NH;
  (e) a peptide comprising 1 to 100 amino acids; and
  (f) Dendritic macromolecules, including dendrimers, dendrons, and hyperbranched polymers.

The methods of the invention, as summarized in FIG. 1, involve reducing a disulfide of a protein to be modified, forming a reduced protein that contains two free thiol groups. The reduced protein is contacted with a functionalized tethering compound that is capable of reacting with both of the free thiols on the reduced protein to tether the free thiols together, while also retaining at least one functional group on the tether that is suitable for attaching a payload. In some embodiments, the functional group on the tether is a carbonyl group, e.g., the ketone obtained when the free thiols are allowed to react with a 1,3-dihaloketone. Because the free thiols are strongly nucleophilic, they react readily with electrophiles such as alkyl halides or alkyl tosylates, via irreversible reactions that involve displacing a leaving group and forming a covalent sulfur-carbon bond. Some suitable examples of functionalized carbonyl-containing tethering compounds include 1,3-dichloroacetone and 1,3-dibromoacetone. These reagents have been used to provide stabilization of disulfide moieties in small cyclic peptides by tethering sulfhydryls together. See e.g. WO2008/157380 (reaction of dichloroacetone with a reduced cyclic pentapeptide, followed by reduction of the carbonyl). Sulfonates of 1,3-dihydroxyacetone (e.g., mesylate, triflate, phenylsulfonate, tosylate, and the like) can also be used. These reagents are sufficiently reactive toward the free thiols of a reduced protein to provide reasonably rapid reaction to form an activated protein with two cysteine residues tethered together, wherein each of the free thiols is covalently attached to the functionalized tethering group.

The reduced protein and functionalized tethering compound are contacted under conditions suitable to promote reaction between the tethering compound and the two free thiols of the reduced protein, and particularly under conditions of concentration and temperature that favor causing both of the free thiols that were previously joined in a disulfide bond to react with a single molecule of the tethering compound so they are once again tied together, but now with a short tether connecting them instead of a direct disulfide bond. This reaction forms an activated protein as illustrated in FIG. 1, having a functionalized tether [—$CH_2$C(O)—$CH_2$—] between the two sulfur atoms. The tether in FIG. 1 includes a carbonyl that can be used to efficiently attach a payload via clean and efficient Schiff base formation chemistry.

It is understood throughout this discussion that the protein, even though it is depicted as a circle or sphere, can be a small polypeptide of fewer than 10 amino acids or a large enzyme or complex of two or more subunits or distinct proteins. The two sulfur atoms of the disulfide can be on one subunit of a multimeric complex, or they can be on different subunits. In addition to the disulfide participating in the transformations described herein, the protein may also contain other disulfide linkages that may be reduced and functionalized, or may not be reduced due to their location within the protein. While only a single disulfide, tethering group, or conjugation is shown, it is understood that a polypeptide or protein comprising one such disulfide, tethering group or conjugation may also contain more than one. The methods of the invention can utilize known methods to selectively reduce solvent-accessible disulfide linkages near the surface of the folded protein, often without reducing 'buried' disulfides that may be essential for maintaining the overall shape and functionality of the protein, or for keeping two subunits linked together in a multi-subunit complex. As the examples illustrate, a protein or polypeptide can contain more than one functionalized tethering group, and thus can contain more than one conjugation site, even though only one is typically depicted for simplicity.

Once the activated protein has been formed, a payload can be attached to the functionalized tether. For example, an amine-containing (or aminated) payload can be attached to the tether formed from dihaloacetone by forming a Schiff base between the payload's amine and the tether's ketone. Suitable payload compounds contain an —$NH_2$ amine group that is accessible and reactive; in preferred embodiments, the amine is one that is activated toward forming a Schiff base. Examples of suitable amines include oxyamines (X=O), thioamines (X=S), and hydrazines (X=NH), for example: these heteroatom-substituted amines are known to condense readily with ketones such as the one on the tether of an activated protein formed from a dihaloacetone as shown in FIG. 1.

The activated protein is typically contacted with an amino-containing payload without purification or isolation of the activated protein. A free —NH$_2$ group on the payload (PL) can be used if available, but if none is available, one can be added via a linking group as illustrated in FIG. 1 and in the examples. In some embodiments, once the activated protein is generated, the amino-payload is added to the reaction mixture where the activated protein was formed under conditions that promote formation of the desired Schiff base. The amino-payload then reacts via its amine group with the carbonyl of the activated protein as illustrated in FIG. 1, thereby forming the desired Protein-Payload conjugate, wherein X is O, NH or substituted N; L is a linking group; and PL represents a payload.

EXAMPLES

The following HPLC methods are used in the examples below.

Method A: Eluent A: water+0.1% Formic acid, Eluent B: Acetonitrile+0.08% Formic acid Gradient: from 3 to 80% B in 2 min—Flow 1.0 ml/min. Column: Proswift Monolith 4.6*50 mm 40° C.

Method B: Eluent A: water+0.1% Formic acid, Eluent B: Acetonitrile+0.04% Formic acid Gradient: from 3 to 80% B in 2 min—Flow 1.0 ml/min. Column: Proswift Monolith 4.6*50 mm 40° C.

Method C: Eluent A: water+3.75 mM ammonium acetate+2% acetonitrile, Eluent B: Acetonitrile Gradient: from 2 to 98% B in 1.7 min—Flow 1.0 ml/min. Column: Acquity CSH 2.1*50 mm 50° C.

Method D (HRMS): Eluent A: water+0.05% Formic acid+3.75 mM ammonium acetate, Eluent B: Acetonitrile+0.04% Formic acid.

Gradient: from 2 to 98% B in 4.4 min—Flow 1.0 ml/min. Column: Acquity CSH 2.1*50 mm 50° C.

Synthesis of a Linker

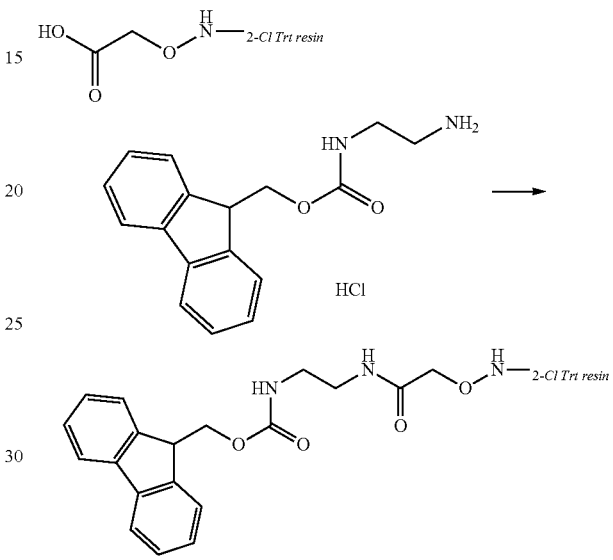

2-Chlorotrityl chloride resin (1.55 mmol/g) (0.500 g, 0.775 mmol) in 100 mL glassware was swollen in DCM (20 ml) for 30 min and it was drained. A suspension of 2-(aminooxy)acetic acid hemihydrochloride (0.338 g, 3.10 mmol) and DIPEA (1.354 ml, 7.75 mmol) in NMP (7 ml)/DCM (4 ml) was added to the resin, which was shaken for 5 h. Solvent was drained. Resin was rinsed with DCM/MeOH/DIPEA (17/2/1, 40 mL), DCM (50 mL), NMP (50 mL) and DCM (50 mL) respectively. Resulting resin was dried with KOH/NaOH overnight.

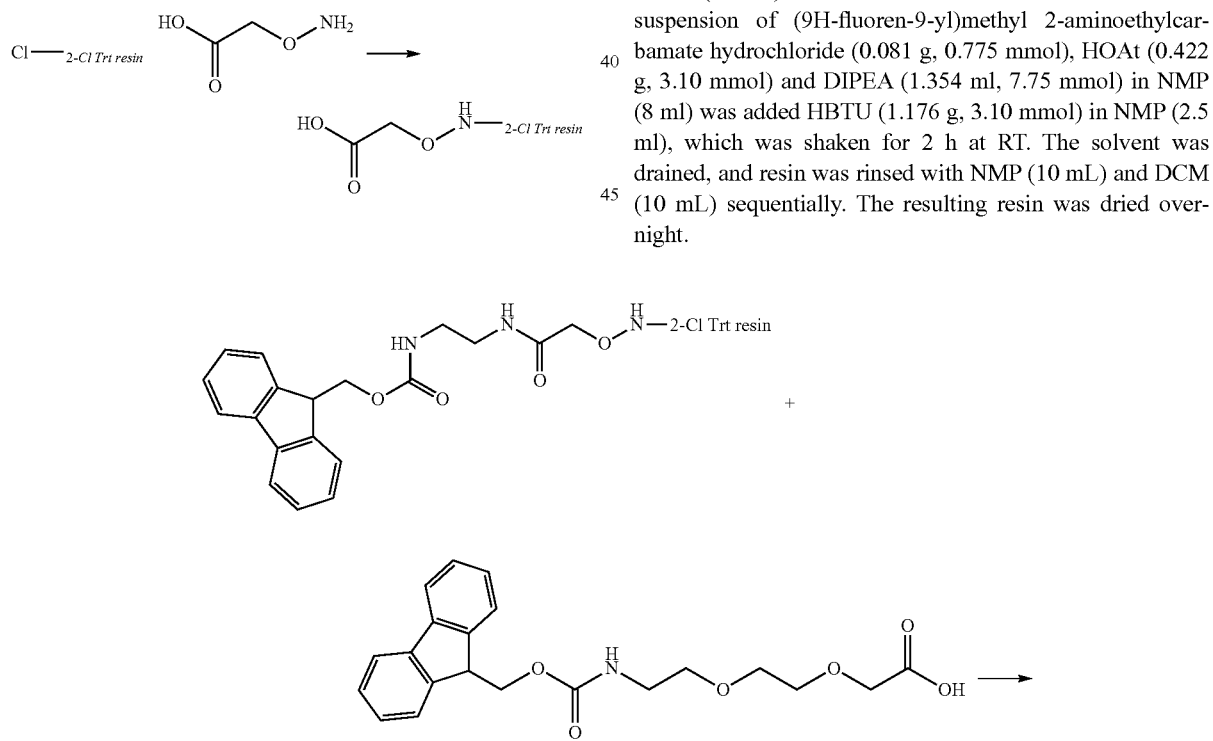

Resin (0.775 mmol) in 100 mL glassware was swollen in DCM (20 ml) for 30 min and it was drained. Into a suspension of (9H-fluoren-9-yl)methyl 2-aminoethylcarbamate hydrochloride (0.081 g, 0.775 mmol), HOAt (0.422 g, 3.10 mmol) and DIPEA (1.354 ml, 7.75 mmol) in NMP (8 ml) was added HBTU (1.176 g, 3.10 mmol) in NMP (2.5 ml), which was shaken for 2 h at RT. The solvent was drained, and resin was rinsed with NMP (10 mL) and DCM (10 mL) sequentially. The resulting resin was dried overnight.

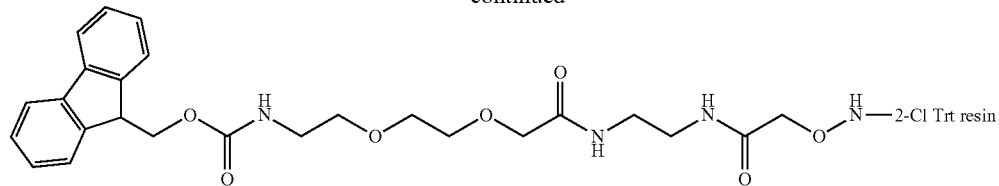

Resin (0.775 mmol) was charged into a reaction vessel. 10 mL of 20% PIPERIDINE/NMP (v/v) was added, and the suspension was agitated at room temperature for 5 min. After solvent was drained, additional 10 mL of 20% PIPERIDINE/NMP (v/v) was added and agitated for 20 min at room temperature. A solution of HOAt (0.316 g, 2.325 mmol) and 1-(9H-fluoren-9-yl)-3-oxo-2,7,10-trioxa-4-azadodecan-12-oic acid (0.896 g, 2.325 mmol) in NMP (8 mL) was added into resin and DIC (0.362 ml, 2.325 mmol) in NMP (1 ml) was added. The reaction mixture was agitated for 2 h at room temperature, and the resin was filtered off and rinsed with NMP (10 ml) four times. The resulting resin was dried overnight.

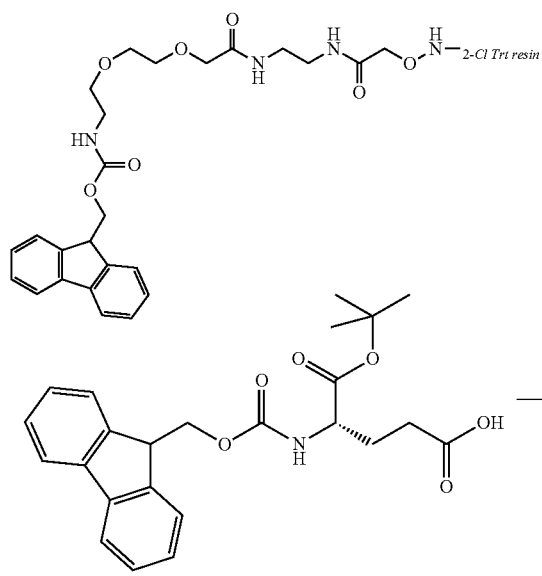

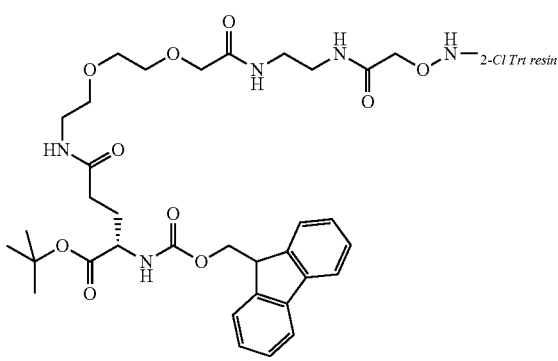

Resin (0.775 mmol) was charged into a reaction vessel. 10 mL of 20% PIPERIDINE/NMP (v/v) was added into resin, and the suspension was agitated at room temperature for 5 min. After solvent was drained, additional 10 mL of 20% PIPERIDINE/NMP (v/v) was added and agitated for 20 min at room temperature. A solution of HOAt (0.316 g, 2.325 mmol) and Fmoc-Glu-OtBu (0.989 g, 2.325 mmol) in NMP (8 ml) was added into resin and DIC (0.362 ml, 2.325 mmol) in NMP (2.00 ml) was added. The reaction mixture was agitated for 2 h at room temperature. Resin was filtered off and rinsed with NMP (10 ml) four times. The resulting resin was dried overnight.

Attaching a Payload to Linker

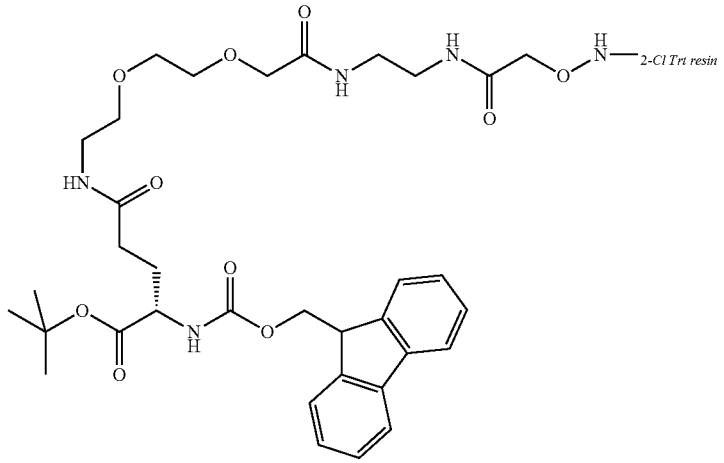

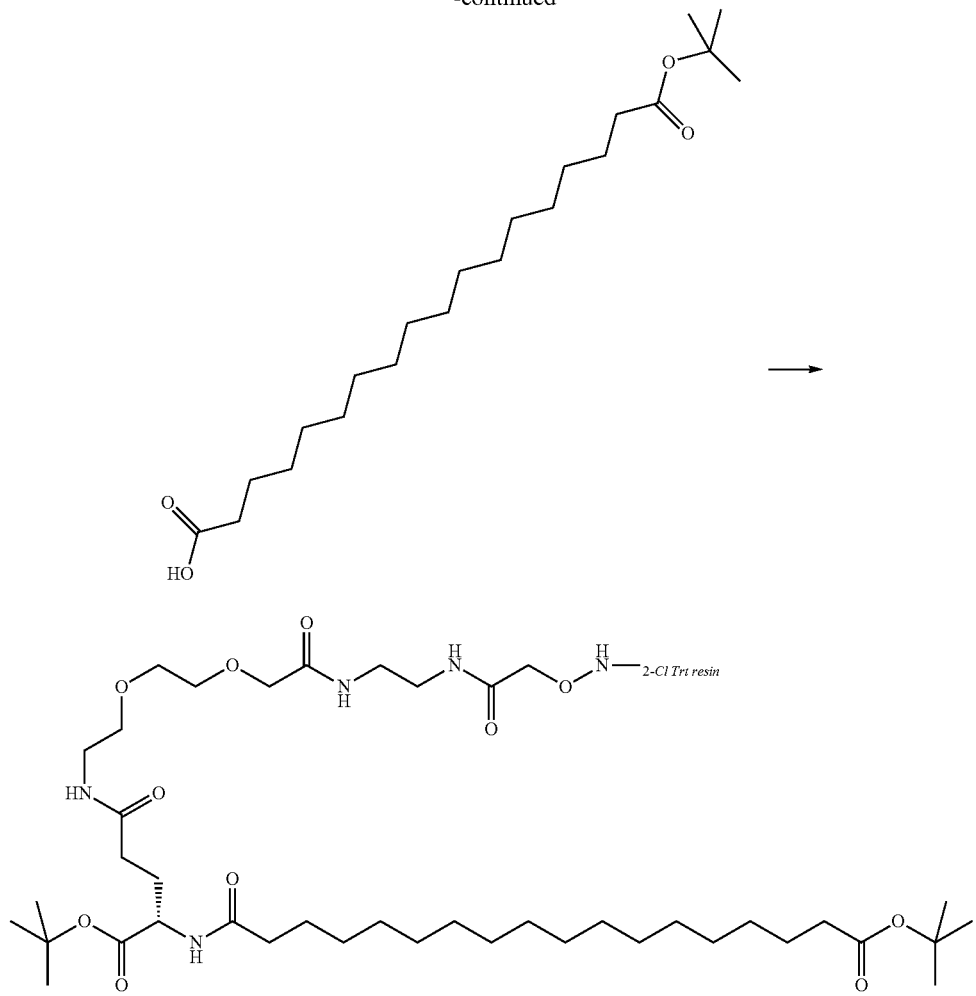

Resin (2-chlorotrityl chloride resin, 0.775 mmol) was charged into a reaction vessel. 10 mL of 20% PIPERIDINE/NMP (0.775 mmol, v/v) was added into resin, and the suspension was agitated at room temperature for 5 min. After solvent was drained, additional 10 mL of 20% PIPERIDINE/NMP (0.775 mmol) was added and agitated for 20 min at room temperature. A solution of 18-tert-butoxy-18-oxooctadecanoic acid (0.862 g, 2.325 mmol) and HOAt (0.316 g, 2.325 mmol) in NMP (8 mL) was added into resin and DIC (0.362 mL, 2.325 mmol) in NMP (2.00 ml) was added. The reaction mixture was agitated for 4 h at room temperature. Resin was filtered off and rinsed with NMP (10 ml) four times. The resulting resin was dried overnight.

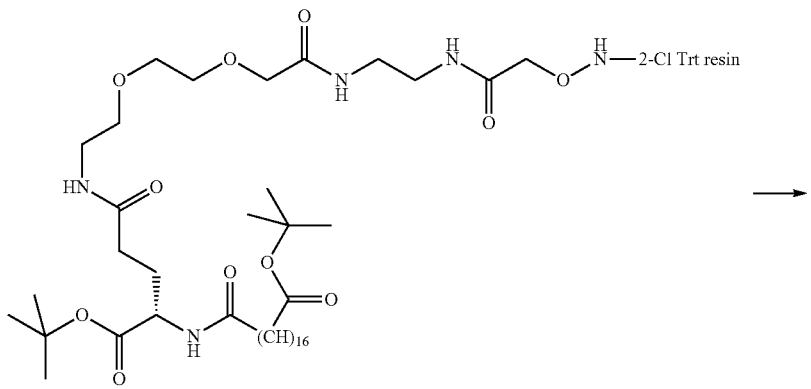

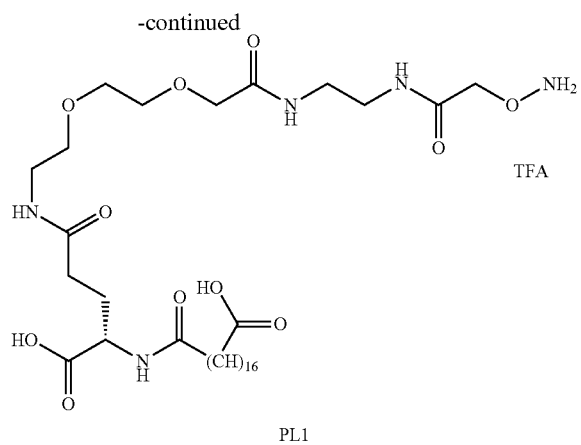

PL1

Resin from the preceding step (0.775 mmol) was treated with 20 mL of cleavage cocktail (TFA/TIPS/water=95/2.5/2.5, v/v) for 1.5 h at room temperature. Resin was removed by filtration and rinsed with TFA. The filtrate was concentrated in vacuo. RP-HPLC with C18 column eluting with 15-50% MeCN/water plus 0.1% TFA gave (S)-1-(aminooxy)-19-carboxy-2,7,16,21-tetraoxo-9,12-dioxa-3,6,15,20-tetraazaoctatriacontan-38-oic acid with 2,2,2-trifluoroacetic acid (1:1) (207 mg, 0.294 mmol, 37.9% yield) (PL1). HRMS[M+1] (method D); 704.4459 (observed), 704.4486 (expected).

Example 1

Figure 3A:
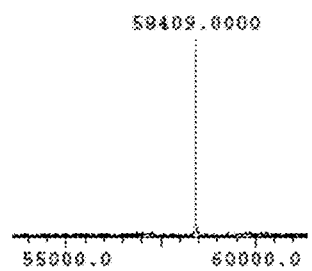
FIGS. 3A-C show mass spectra for the A) starting protein, B) activated protein and C) protein conjugate of Example 1.
Figure 3B:
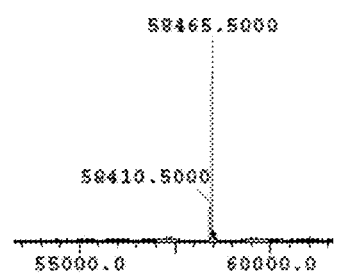
Figure 3C:
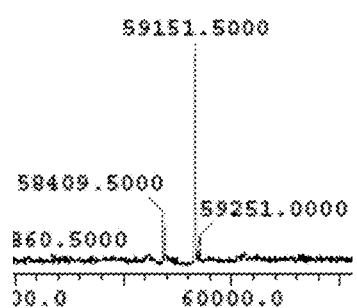

CRM197 (ref: G. Giannini and R. Rappuoli, *Nucleic Acids Res.*, 1984, 25, 4063.) was treated with TCEP (xx), resulting in reduction of the C201-C185 disulfide, with little or no reduction of the C451-C471 disulfide (see Example 3). The reduced CRM197 was treated with 1,3-dichloroacetone to provide the activated protein, having the C451-C471 disulfide intact and with C201 tethered to C185 via a —CH₂—C(=O)—CH₂— linkage. This activated protein was contacted with PL1, the aminated fatty acid derivative containing an aminooxy group whose preparation is described above, to form an oxime linking the fatty acid derivative to the protein. The conjugate with the attached fatty acid group is expected to reduce renal clearance, thus extending the circulating half-life of the CRM197 protein and increasing its usefulness as a carrier in conjugate vaccines. Mass spectral data for the native protein (FIG. 3A, using Method A), the activated protein (FIG. 3B) and the protein conjugate (FIG. 3C) are provided in FIG. 3.

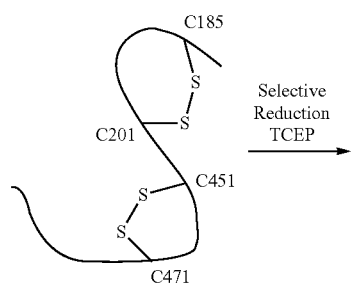

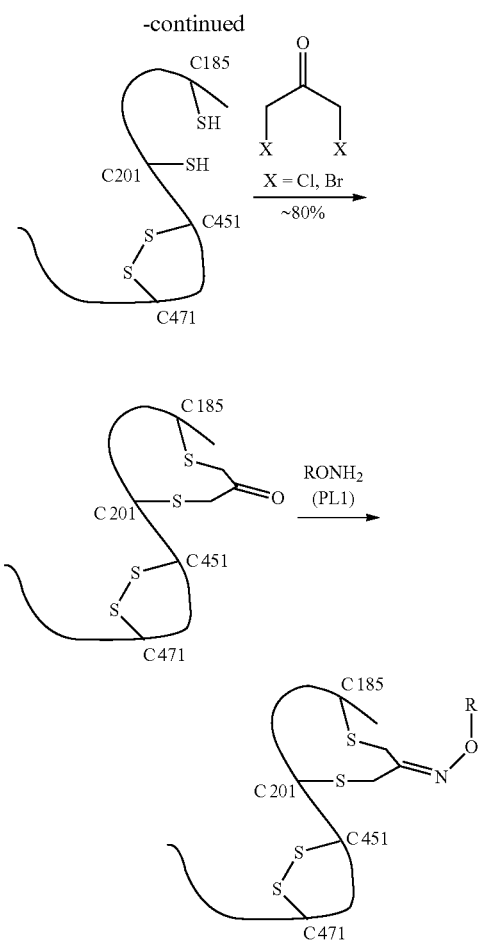

Synthesis of a site-defined azido compound bearing CRM197

Method A—

Eluent A: water+0.1% Formic Acid, Eluent B: Acetonitrile++0.1% Formic Acid

Gradient: from 3 to 80% B in 2 min—Flow 1.8 ml/min.

Column: AcQuity BEH300 SEC 4.6×30 mm 50° C.

SDS Page Gel Analysis—NuPage 4-12% Bis-Tris Gel; 1.5 mm*10 well

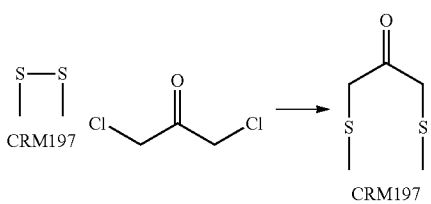

To CRM197 (32.5 mg/ml) (185 μL, 0.103 μmol) in sodium phosphate buffer pH 7.4 (230 μL) was added TCEP HCl (3 mg/mL, water, 58.9 μL, 0.616 μmol). The reaction was stirred at room temperature for 16 h followed by addition of 1,3-dichloropropan-2-one (20 mg/mL, in DMSO, 13.04 μL, 2.054 μmol). The reaction was stirred for 3.5 h, then passed through 0.5 mL Zeba™ spin size exclusion column (7K MWCO, from Thermo Scientific) and buffer exchanged to 0.1 M sodium phosphate buffer pH 6 to afford the ketone-bearing CRM197 (6.78 mg/ml, 1.3 mL, nanodrop method)

LCMS [M+1]=58465

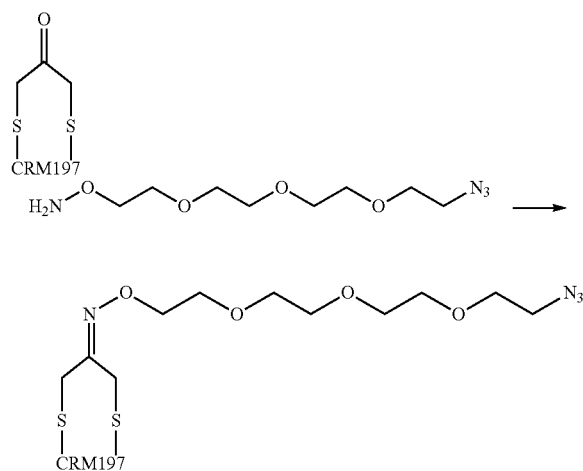

Into a solution of ketonemodified CRM197 (6.78 mg/ml—sodium phosphate buffer pH6, 1.3 mL, 0.151 μmol) was added O-(2-(2-(2-(2-azidoethoxy)ethoxy)ethoxy)ethyl) hydroxylamine (300 mg/ml—DMSO) (0.044 mL, 0.045 mmol). The reaction mixture was agitated for 36 h at 23° C. then passed through 5 mL Zeba™ spin column eluting with PBS 7.4 to provide the title compound (4.41 mg/ml, 1.6 mL, 80% yield, Nano drop method)

LCMS [M+1]=58682.5

Figure 4:
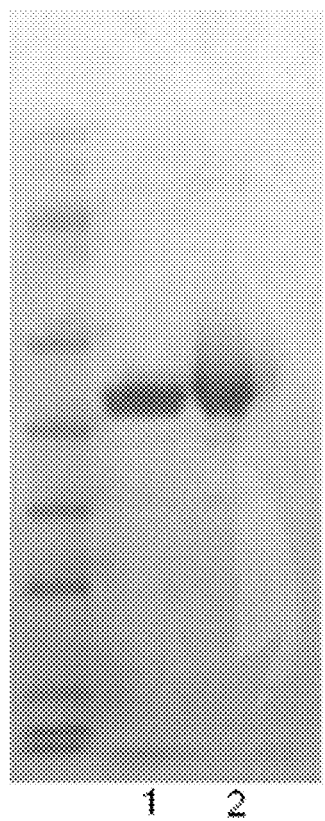
FIG. 4 shows the SDS Page gel analysis of the azido substituted CRM197 construct from Example 1.

FIG. 4 shows the SDS Page for the title compound, the modified CRM197.

Example 2

Starting material preparation: Synthesis of pE-R—P—R-L-C—H—K-G-P-Nle-C—F—OH (SEQ ID NO: 2) (disulfide $C^6$-$C^{12}$) (8)

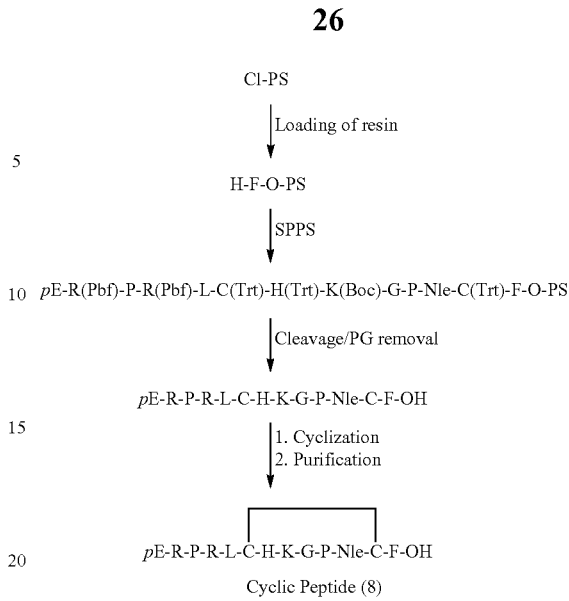

Image aiscloses SEQ ID NOS 3, 2 and 4 respectively, in order of appearance.

Preparation of Intermediate 8a (Loading of 2-Chlorotrityl Chloride Resin with Fmoc-F—OH, Fmoc Removal and Determination of the Loading of the Resin)

2-Chlorotrityl chloride resin (40.0 g, 64.0 mmol) was washed with DCM (3×). A solution of Fmoc-F—OH (24.8 g, 64.0 mmol) in DCM (400 mL) and DIPEA (44.7 mL, 256 mmol) was added and the suspension was shaken for 22 h at room temperature. The resin was washed thoroughly with DCM/MeOH/DIPEA (17:2:1) (3×), DCM (3×), DMA (3×), DCM (3×). The resin was then treated four times for 10 min with a mixture of piperidine/DMA (1:4) (400 mL) followed by washing with DMA (2×180 ml). The piperidine/DMA solutions and DMA washing solutions were collected for determination of the loading of the resin. 1 mL of the combined solutions was diluted to 500 mL with MeOH and the UV absorption at 299.8 nm was measured to be A=0.368. This corresponds to an Fmoc amount of 46.2 mmol. The resin was washed thoroughly with DCM (3×), DMA (3×), DCM (3×) and dried in vacuo to give Intermediate 8a (50.7 g; loading=0.91 mmol/g).

Preparation of Intermediate 8b (Assembly of Linear Peptide)

Intermediate 8a (2.64 g, 2.40 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | C(Trt) | 2 × 30 min | D |
| 2 | Nle | 2 × 15 min | A |
| 3 | P | 2 × 15 min | A |
| 4 | G | 2 × 30 min | A |
| 5 | K(Boc) | 2 × 15 min | A |
| 6 | H(Trt) | 2 × 15 min | A |
| 7 | C(Trt) | 2 × 60 min | D |
| 8 | L | 2 × 15 min | A |
| 9 | R(Pbf) | 4 × 1 h | A |
| 10 | P | 2 × 15 min | A |
| 11 | R(Pbf) | 4 × 1 h | A |
| 12 | pE | 2 × 15 min | A |

Preparation of Intermediate 8c (Cleavage from the Resin with Protecting Group Removal)

Intermediate 8b (2.40 mmol) was carefully washed with DCM (4×). A mixture of 95% aq. TFA/EDT/TIPS (95:2.5:2.5) (50 mL) was added and the suspension was shaken at room temperature for 1 h. The cleavage solution was filtered off, and fresh cleavage solution (35 mL) was added. The suspension was shaken at room temperature for 1 h then the cleavage solution was filtered off. Fresh solution (35 mL) was added and the suspension was shaken at room temperature for 1 h. The cleavage solution was filtered off. The combined cleavage solutions were poured slowly onto a stirred mixture of cold heptane/diethyl ether (1:1) (500 mL), giving a precipitate. The suspension was stirred at room temperature for 2 h and then the precipitate was allowed to settle down. The supernatant was sucked off with a frit. The residue was washed with cold heptane/diethyl ether (1:1) (2×100 mL), the supernatant was sucked off with a frit. The solid was dried in high vacuum to afford Intermediate 8c as an off-white solid (3.75 g, 1.88 mmol).

Preparation of Cyclic Peptide 8 (Cyclization and Purification)

Intermediate 8c (3.75 g, 1.88 mmol) was dissolved in $H_2O$ (375 mL). A solution of 50 mM $I_2$ in AcOH (45.1 mL, 2.26 mmol) was added in one portion to the stirred solution and the solution was stirred for 10 min at room temperature. 0.5 M Ascorbic acid in $H_2O$ (5.64 mL, 2.82 mmol) was added to quench the excess of $I_2$. The solution was concentrated to near dryness. The reaction was performed in two poroom temperatureions: 0.188 mmol scale and 1.69 mmol scale. The crudes were combined for purification. The crude was purified by preparative HPLC and lyophilized from ACN/$H_2O$ to afford Compound 8 as a white solid (1.53 g, 0.767 mmol).

The pure product was analyzed by analytical HPLC (Analytical method C: $t_R$=3.43 min) and UPLC-MS (Analytical method B; measured: [M+3]/3=512.4; calculated: [M+3]/3=512.6).

This example illustrates formation of an activated protein starting with the cyclic peptide 8.

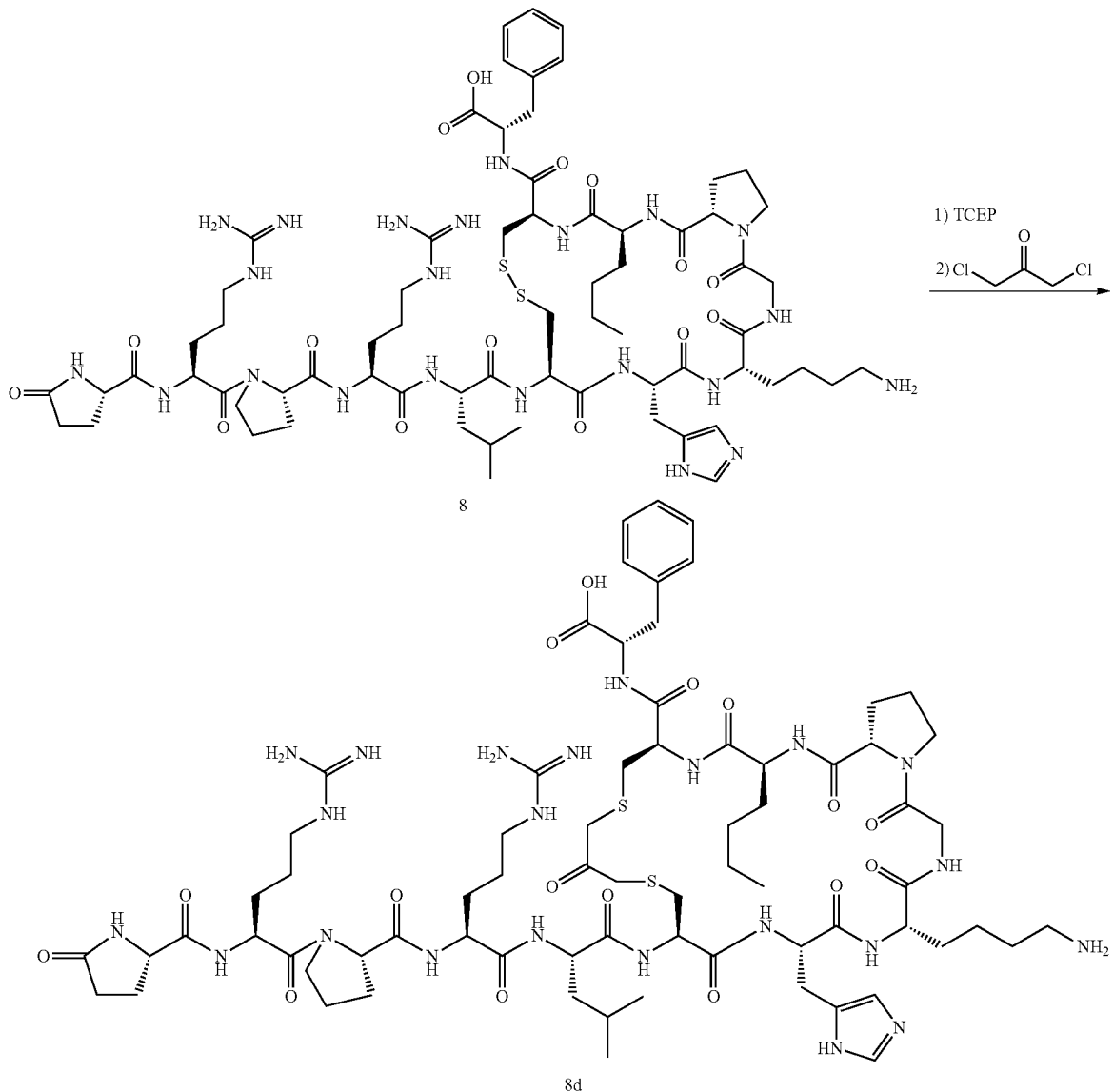

Cyclic peptide 8 (12 mg, 6.76 μmol) was dissolved in 50 mM Na phosphate buffer pH6.5 (1.5 ml), into which was added TCEP HCl (2.91 mg, 10.13 μmol) at room temperature. This reaction mixture was stirred for 1 h at room temperature. Into above solution was added 1,3-dichloropropan-2-one (4.29 mg, 0.034 mmol) at room temperature, which was stirred for 30 min at room temperature. RP-HPLC eluting 15-60% MeCN/water with 0.1% TFA gave activated protein 8d (6 mg, 2.93 μmol, 43.4% yield). HRMS [M+1] (method D); 1590.7911 (observed), 1590.7912 (expected).

pE-R—P—R-L-C—H—K-G-P-Nle-C—F—OH (SEQ ID NO: 5) with a —S—CH$_2$—C(=Z)—CH$_2$—S— linkage between the 2 cysteines at position 6 and 12 [C$^6$-C$^{12}$], and Z is:

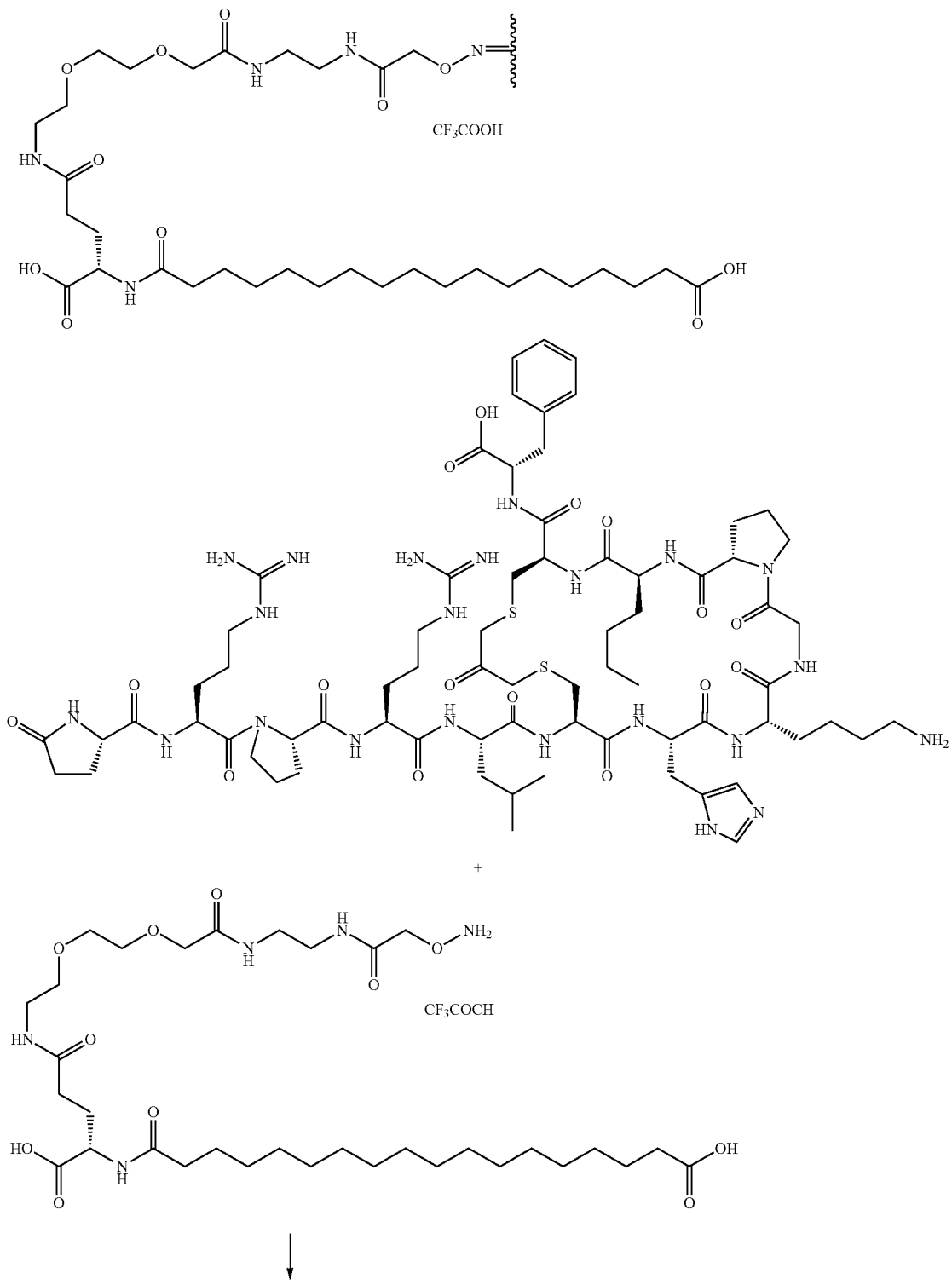

-continued

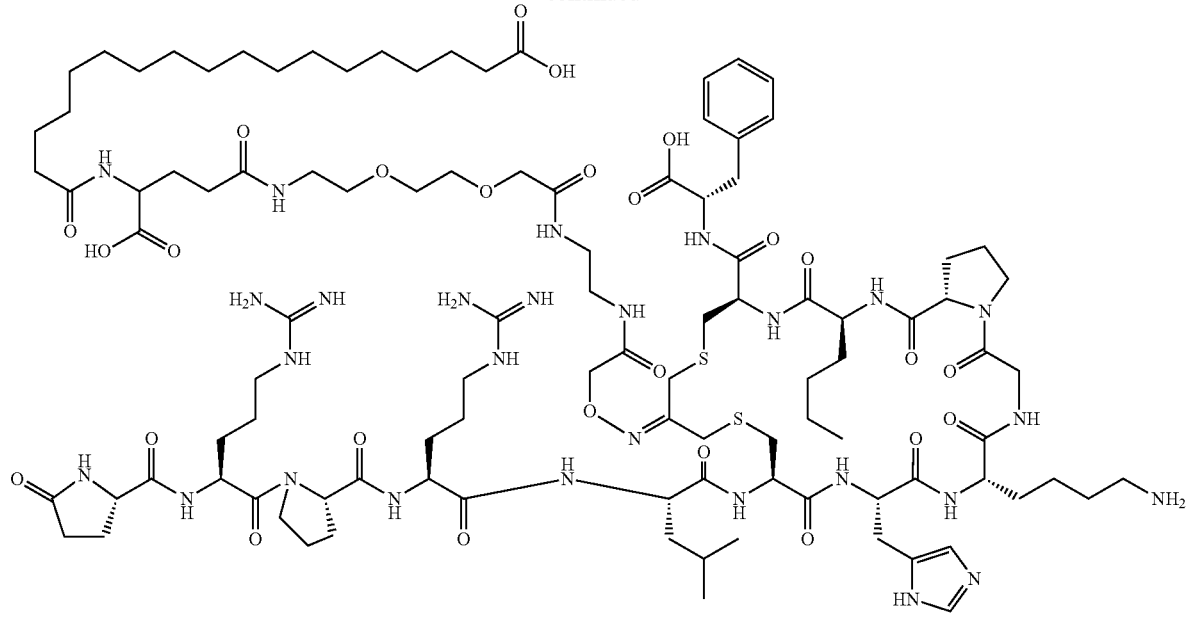 [SMILES: CCCC[C@@H]1NC(=O)[C@@H]2CCCN2C(=O)CNC(=O)[C@H](CCCCN)NC(=O)[C@H](Cc2cnc[nH]2)NC(=O)[C@@H](NC(=O)[C@H](CC(C)C)NC(=O)[C@H](CCCNC(=N)N)NC(=O)[C@@H]2CCCN2C(=O)[C@H](CCCNC(=N)N)NC(=O)[C@@H]2CCC(=O)N2)CSC/C(=N/OCC(=O)NCCNC(=O)COCCOCCNC(=O)CCC(NC(=O)CCCCCCCCCCCCCCCCC(=O)O)C(=O)O)CSC[C@@H](C(=O)N[C@@H](Cc2ccccc2)C(=O)O)NC1=O]

Into a solution of Compound 8 ((S)-2-((3S,6R,14R,17S,20S,28aS)-17-((1H-imidazol-5-yl)methyl)-20-(4-aminobutyl)-3-butyl-14-((S)-2-((S)-5-guaidino-2-((S)—((S)-5-guaidi-2-((S)-5-oxopyrrolidine-2-carboxamido)pentanoyl)pyrrolidine-2-carboxamido)pentanamido)-4-methylpentanamido)-1,4,10,15,18,21,24-heptaoxohexacosahydropyrrolo[2,1-i][1,23,4,7,10,13,16,19]dithiahexaazacyclohexacosine-6-carboxamido)-3-phenylpropanoic acid) (11.5 mg, 5.62 µmol) and (S)-1-(aminooxy)-19-carboxy-2,7,16,21-tetraoxo-9,12-dioxa-3,6,15,20-tetraazaoctatriacontan-38-oic acid compound with 2,2,2-trifluoroacetic acid (1:1) (9.19 mg, 0.011 mmol) in 100 nM Na phosphate buffer pH6.0 (1 ml) was added aniline (2.051 µl, 0.022 mmol) at room temperature. Addition of DMSO (50 µl) gave homogeneous solution. This reaction mixture was stirred at room temperature for 2 h. RP-HPLC eluting 15-60% MeCN/water with 0.1% TFA gave the expected conjugate, (1-((Z)-((3 S,6R,14R,17S,20S,28aS)-17-((1H-imidazol-5-yl)methyl)-20-(4-aminobutyl)-3-butyl-6-((S)-5-carboxy-2-phenylethylcarbamoyl)-14-((S)-2-((S)-5-guanidino-2-((S)-1-((S)-5-guanidino-2-((S)-5-oxopyrrolidine-2-carboxamido)pentanoyl)pyrrolidine-2-carboxamido)pentanamido)-4-methylpentanamido)-1,4,15,18,21,24-hexaoxodocosahydropyrrolo[2,1-i][1,23,4,7,10,13,16,19]dithiahexaazacyclohexacosin-10(1H,9H,11H)-ylidene)aminooxy)-19-carboxy-2,7,16,21-tetraoxo-9,12-dioxa-3,6,15,20-tetraazaoctatriacontan-38-oic acid) (4.5 mg, 1.646 µmol, 29.3% yield). HRMS (method D) [(M+3)/3]; 759.7487 (observed), 759.7462 (expected). Retention time 4.12 min.

Example 3

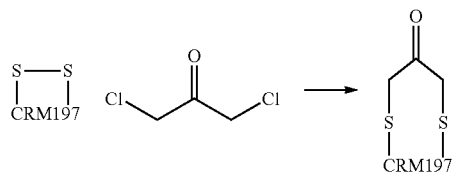

Into a solution of CRM197 (200 µg, 6.2 ul, 0.0034 µmol) in 50 mM Na phosphate buffer pH7.4 (10 µl) was added aqueous solution of TCEP HCl (5.89 µg, 0.021 µmol). This reaction mixture was left for 15 h at room temperature. 1,3-dichloropropan-2-one (4.58 µg, 0.034 µmol 10 eq) was added into the mixture. This reaction was left at room temperature for 2 h. The crude was passed through a Zeba™ size exclusion column. LCMS; [M+1]=58465. This activated protein can be reacted with an aminated payload such as a TLR agonist, to form a carrier protein conjugated with a compound that may enhance immune responses to any antigen added to the carrier protein.

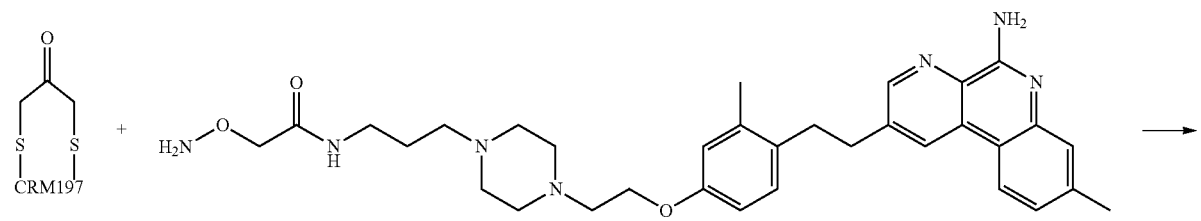

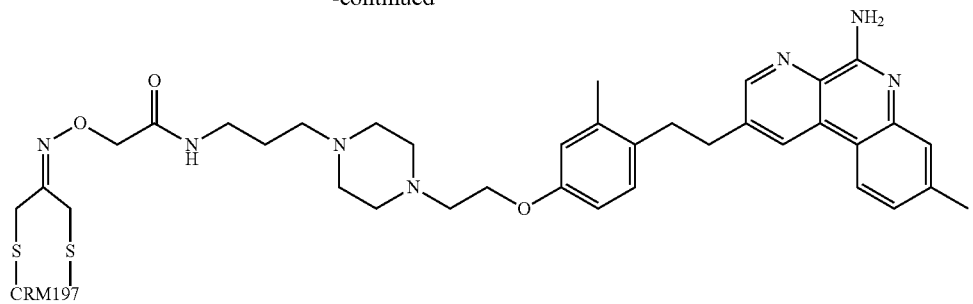

Into a solution of ketone-modified CRM197 (5 mg/ml, Na phosphate buffer, pH6.0) (50 μg, 0.00086 μmol) were added N-(3-(4-(2-(4-(2-(5-amino-8-methylbenzo[f][1,7]naphthyridin-2-yl)pethyl)-3-methylphenoxy)ethyl)piperazin-1-yl)propyl)-2-(aminooxy)acetamide (66.8 μg, 0.064 μmol) and aniline (0.0020 μl, 0.021 μmol). This reaction was left for 14 h at 23° C. to give the desired conjugate A based on LCMS analysis. Reaction mixture was passed through 0.5 mL Zeba™ size exclusion column eluting PBS pH7.2 buffer. LCMS; [M+1]=59032.

Synthesis of PL:

(0.5 mL, 6.49 mmol). This was stirred for 30 min at RT. After removal of solvent, RP-HPLC purification eluting 15-60% MeCN/water with 0.1% TFA gave N-(3-(4-(2-(4-(2-(5-amino-8-methyl benzo[f][1,7]naphthyridin-2-yl)ethyl)-3-methylphenoxy)ethyl)piperazin-1-yl)propyl)-2-(aminooxy)acetamide (25 mg, 0.024 mmol, 21.02% yield). LCMS; [M+1]=586.

Example 4

The following example uses an anti-VEGF antibody fragment (VEGF-Fab), and a fatty acid derivative that is

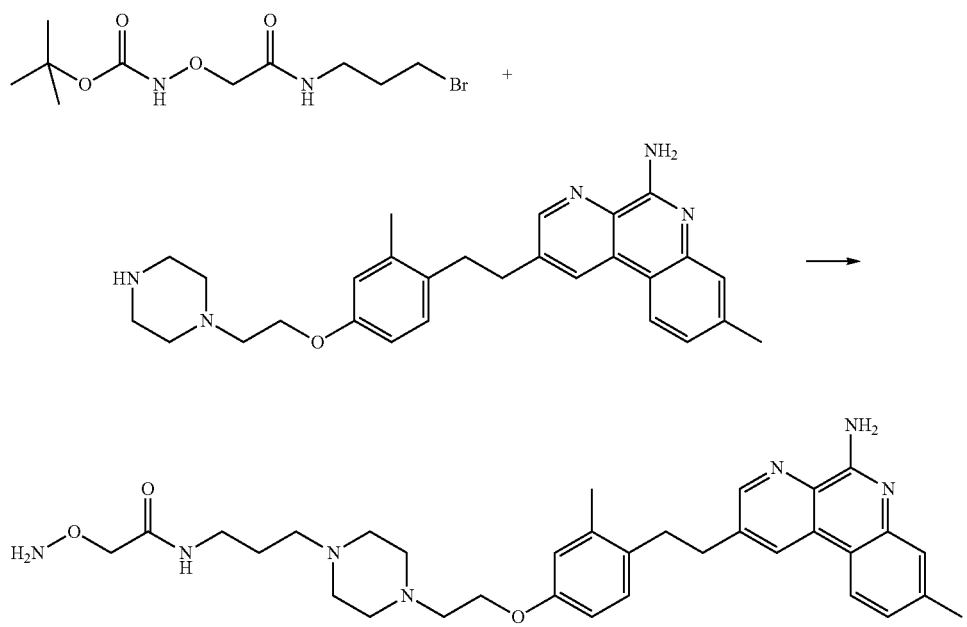 [SMILES: CC(C)(C)OC(=O)NOCC(=O)NCCCBr ; Cc1ccc2c(c1)nc(N)c1ncc(CCc3ccc(OCCN4CCNCC4)cc3C)cc12 ; Cc1ccc2c(c1)nc(N)c1ncc(CCc3ccc(OCCN4CCN(CCCNC(=O)CON)CC4)cc3C)cc12]

Into a solution of tert-butyl 2-(3-bromopropylamino)-2-oxoethoxycarbamate (53.3 mg, 0.171 mmol) and 8-methyl-2-(2-methyl-4-(2-(piperazin-1-yl)ethoxy)phenethyl)benzo[f][1,7]naphthyridin-5-amine (52 mg, 0.114 mmol) in DMF (0.5 ml) was added potassium carbonate (39.4 mg, 0.285 mmol) at RT, which was stirred for 24 h at RT. water and EtOAc was added. The organic layer was separated. The aqueous layer was extracted with EtOAc. The combined organic layer was dired over $Na_2SO_4$, filtered and concentrated in vacuo to give crude Boc-protected material. This was dissolved in DMF (0.5 ml), into which was added TFA added to increase serum half-life of the antibody fragment. Selective reduction of the inter-chain disulfide in the presence of several less accessible intra-chain disulfide linkages is achieved using TCEP in PBS at pH 7. The reduced protein is reacted with a dihaloacetone (dibromoacetone or dichloroacetone) to provide an activated protein having the three-carbon tether —$CH_2$—C(=O)—$CH_2$— linking the sulfur atoms together. The activated protein is contacted with a linker-payload moiety having an aminooxy as the reactive portion to form an oxime with the ketone derived from the dihaloacetone. The linking group L in this example is

Figure 5:
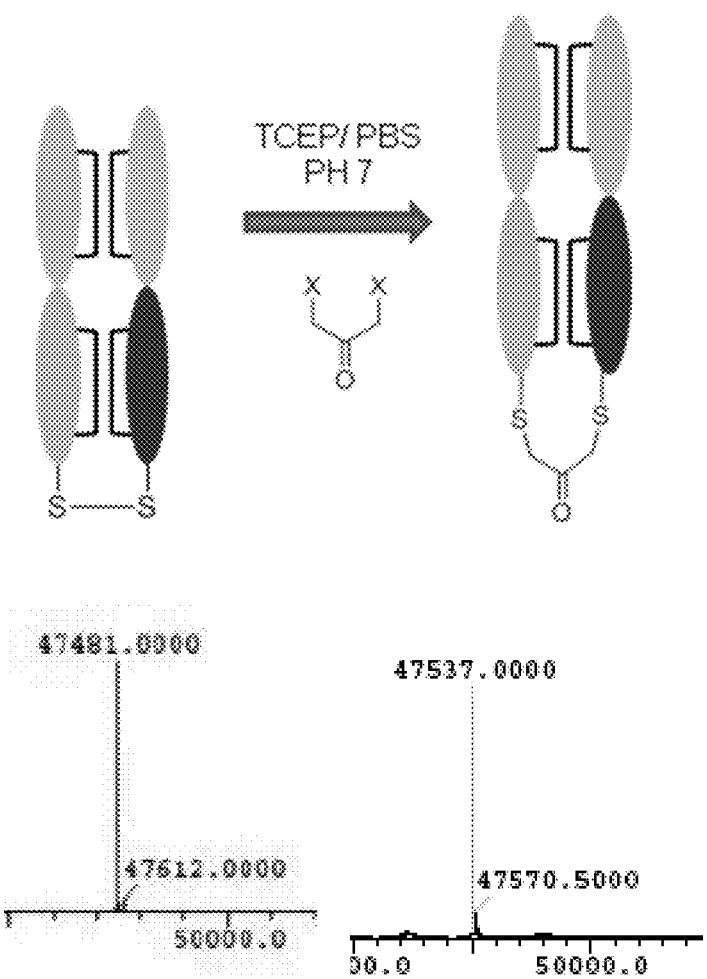
FIG. 5 shows a schematic depiction of the activated protein for Example 4 and LC-MS data for the activated (ketone-modified) protein.

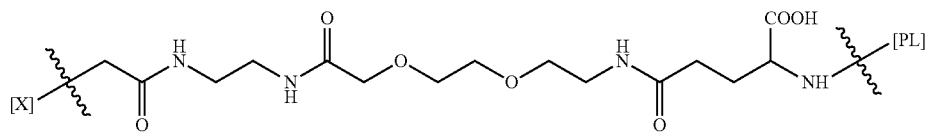

where [X] and [PL] indicate the points of attachment for —X—NH$_2$ and payload PL, respectively, and the payload is a C18 fatty acid group. In the example, X is —ONH$_2$, which forms an oxime with the carbonyl of the acetonyl ketone of the activated protein. FIG. 5 depicts the formation of the activated protein for this example and shows the mass spectral evidence for its formation.

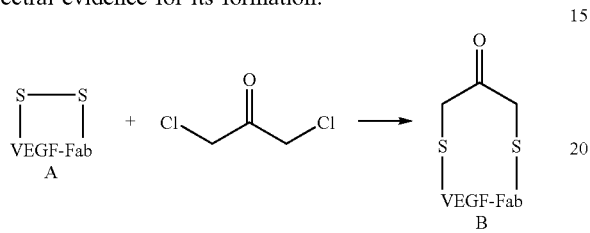

Into a solution of A (72.72 μg, 6.0 uL, 0.0015 μmol) in PBS pH7.4 (8 μl) was added TCEP HCl (2.63 μg, 0.0092 μmol). This reaction mixture was left for 3 h at room temperature. 1,3-dichloropropan-2-one (1.945 μg, 0.015 μmol) was added and the reaction was allowed to stand at room temperature for 1 h. A was consumed and converted into desired product B. The crude was passed through a size exclusion column. LCMS; [M+1]=47538

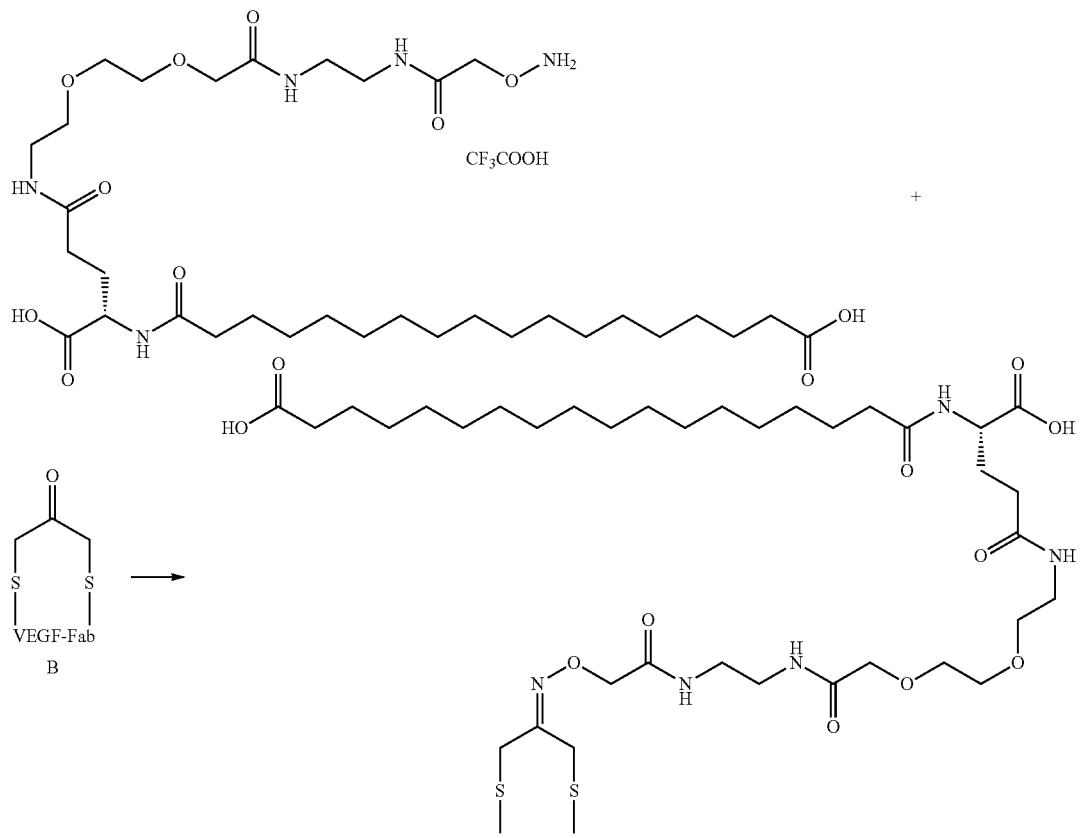

Into a solution of B (36.36 µg, 0.00076 µmol) in PBS pH7.4 (22.5 µl) were added (S)-1-(aminooxy)-19-carboxy-2,7,16,21-tetraoxo-9,12-dioxa-3,6,15,20-tetraazaoctatriacontan-38-oic acid compound with 2,2,2-trifluoroacetic acid (1:1) (64.33 µg, 0.079 µmol) and aniline (0.00105 µl, 0.011 µmol) at room temperature, which was stirred for 14 h at 23° C. B was consumed and converted into desired product C. The crude was passed through a Zeba™ Spin Desalting Column, 7K MWCO (from Thermo Scientific)) LCMS; [M+1] (method A)=48222. FIG. 6 depicts formation of the protein conjugate and shows mass spectral evidence for conjugate formation.

Example 5

Example 6: Preparation of AntiHer2 Antibody-Drug Conjugates

Method A:
Step 1.

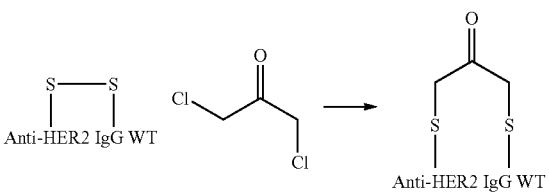

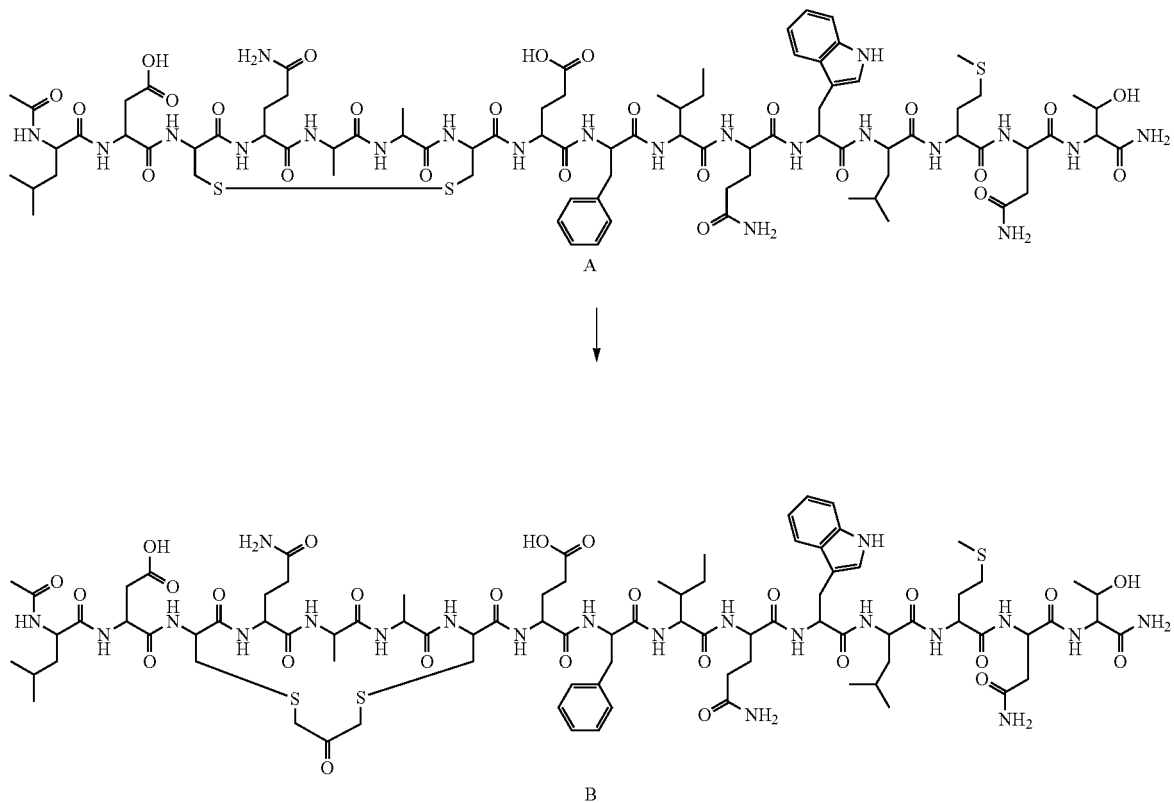

Peptide A (1 mg, 0.519 µmol) was dissolved in buffer (2.5 ml) (50 mM sodium phosphate buffer pH6.5 (1.5 mL), 40% MeCN (0.9 mL), 2.5% DMF (0.1 mL)), into which was added TCEP HCl (0.164 mg, 0.571 µmol) at room temperature. this reaction mixture was stirred for 60 min. 1,3-dibromoacetone (0.164 mg, 0.571 µmol) in DMF (0.1 ml) was added into the reaction mixture at room temperature. After being stirred for 3 min, acetone adduct B was observed to form in quantitative conversion based on LCMS analysis. LCMS (Method C) [M+2]/2=991.

Step 1: Into a solution of Anti-HER2 IgG (20.36 mg/ml in 0.1M Tris/HCl, 30 µl, 610.8 µg, 0.0041 µmol) and 1,3-dichloropropan-2-one (66.1 µg, 0.495 µmol) was added TCEP HCl (14.17 µg, 0.049 µmol), which was agitated for 16 h at 4° C. The reaction mixture was passed through 0.5 mL Zeba™ spin column eluting PBS buffer (pH7.2). Modification of 4 inter chain disulfides was confirmed by analysis with PNGase F (New England Biolab), Endoproteinase Lys-C (Roche) and non reducing/reducing SDS PAGE (4-12% Bis-Tris Gel with colloidal blue staining) performed with samples taken from the reaction solution. LCMS (method B); 145394 (after deglycosylation with PNGase F).

Step 2:

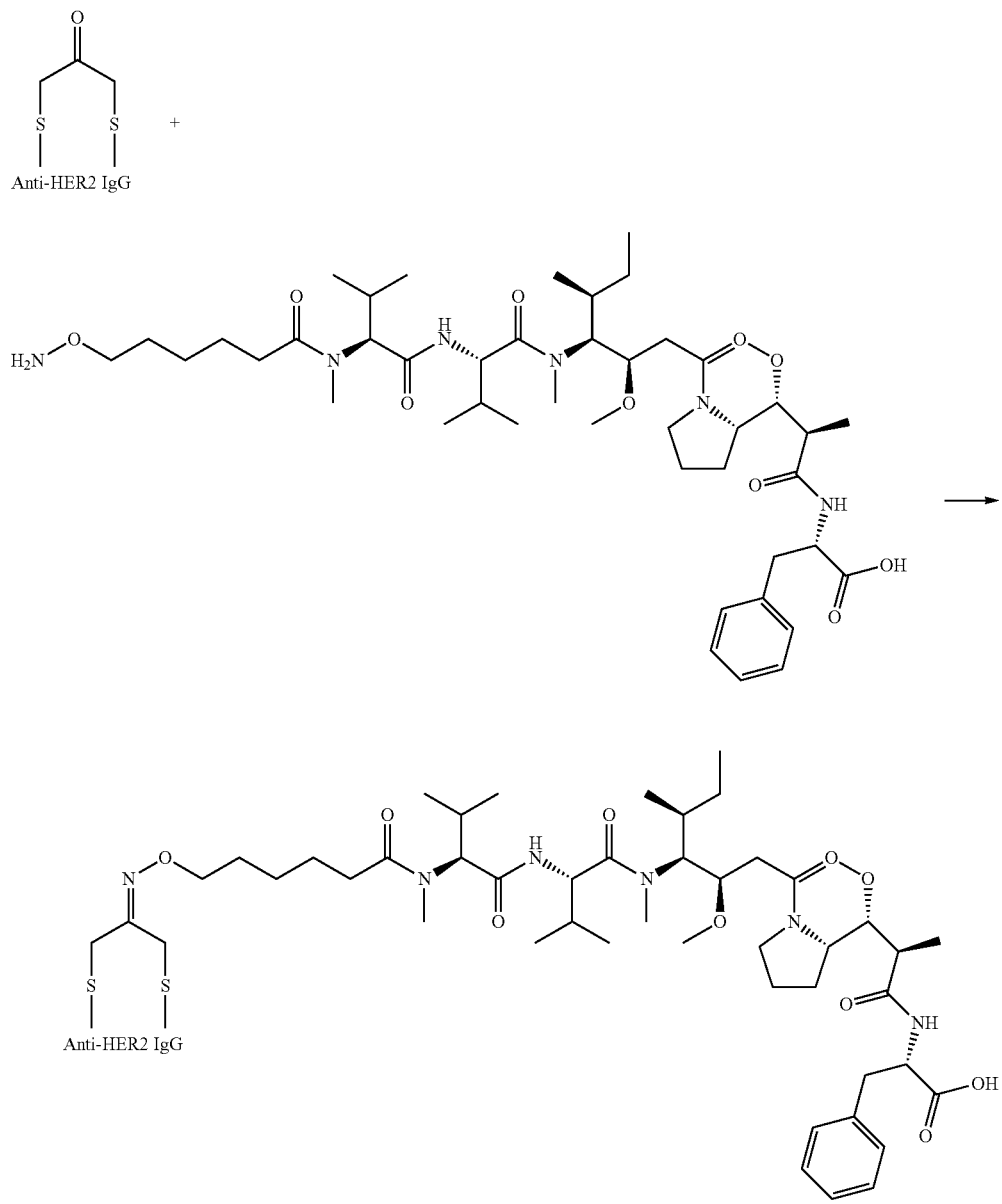

Into a solution of modified Anti-HER2 IgG prepared in Step 1, (7.14 mg/mL, 100 mM anilinium acetate buffer pH4.8, 600 μg, 0.0040 μmol) was added (S)-2-((2R,3R)-3-((S)-1-((3R,4S,5S)-4-((S)-2-((S)-2-(6-(aminooxy)-N-methylhexanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid (30 mg/ml, 104 μg, 0.121 μmol) at room temperature. The resulting mixture was agitated at room temperature for 19 h. The mixture was passed through 0.5 ml Zeba™ spin column one time eluting with PBS buffer (pH7.2). Modification of ketones was confirmed by analysis with PNGase F (New England Biolab), Endoproteinase Lys-C (Roche) and non reducing/reducing SDS PAGE (4-12% Bis-Tris Gel with colloidal blue staining, shown below) performed with samples taken from the reaction solution. DAR (drug-antibody ratio) was 3.2. LCMS (method B); 148770 (after deglycosylation). FIG. 7 shows the conjugate and the conjugate following reduction (see below). SeeBlue Plus2® Pre-Stained Standard (Invitrogen) was used as apparent molecular weights ladder. This demonstrates that little or no unconjugated antibody is present in the conjugation product: unconjugated antibody would produce a lower-molecular weight band upon reduction due to dissociation of the antibody held together only by disulfide bonds. The conjugate, having the fragments covalently linked through the —S—$CH_2$—C(=X)—$CH_2$—S— linkage, cannot dissociate upon reduction.

Method B:
Step 1:

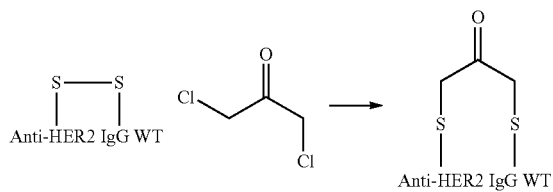

Into a solution of Anti-HER2 IgG (20.36 mg/ml in 0.1M Tris/HCl) (610.8 µg, 0.0041 µmol) (30 ul) and 1,3-dichloropropan-2-one (66.1 µg, 0.495 µmol) was added TCEP HCl (14.17 µg, 0.049 µmol), which was agitated for 16 h at 4° C. The reaction mixture was passed through 0.5 mL Zeba™ spin column eluting PBS pH7.2. Successful modification at inter chain disulfide by 4 acetone formation was confirmed by analysis with PNGase F (New England Biolab), Endoproteinase Lys-C (Roche) and non reducing/reducing SDS PAGE (4-12% Bis-Tris Gel with colloidal blue staining) performed with samples taken from the reaction solution. LCMS (method B); 145394 (after deglycosylation). Reduced sample for SDS PAGE was prepared following the procedure described before.

Step 2:

Into a solution of modified Anti-HER2 IgG (7.14 mg/mL, 100 mM anilinium acetate buffer pH4.8) (600 µg, 0.0040 µmol) was added (S)-2-((2R,3R)-3-((S)-1-((3R,4S,5S)-4-((S)-2-((S)-2-(6-(aminooxy)-N-methylhexanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid (30 mg/ml, 104 µg, 0.121 µmol) at rt, which was agitated for 19 h at RT. The resulting mixture was passed through 0.5 ml Zeba™ spin column one time eluting PBS pH7.2. Successful modification of ketones was confirmed by analysis with PNGase F (New England Biolab), Endoproteinase Lys-C (Roche) and non reducing/reducing SDS PAGE (4-12% Bis-Tris Gel with colloidal blue staining, shown in FIG. 8) performed with samples taken from the reaction solution. DAR was 3.8. LCMS (method B); 148770 (after deglycosylation). SeeBlue Plus2™ Pre-Stained Standard (Invitrogen) was used as apparent molecular weights ladder. Reduced sample for SDS PAGE was prepared following the procedure described before. The SDS PAGE is presented in FIG. 8.

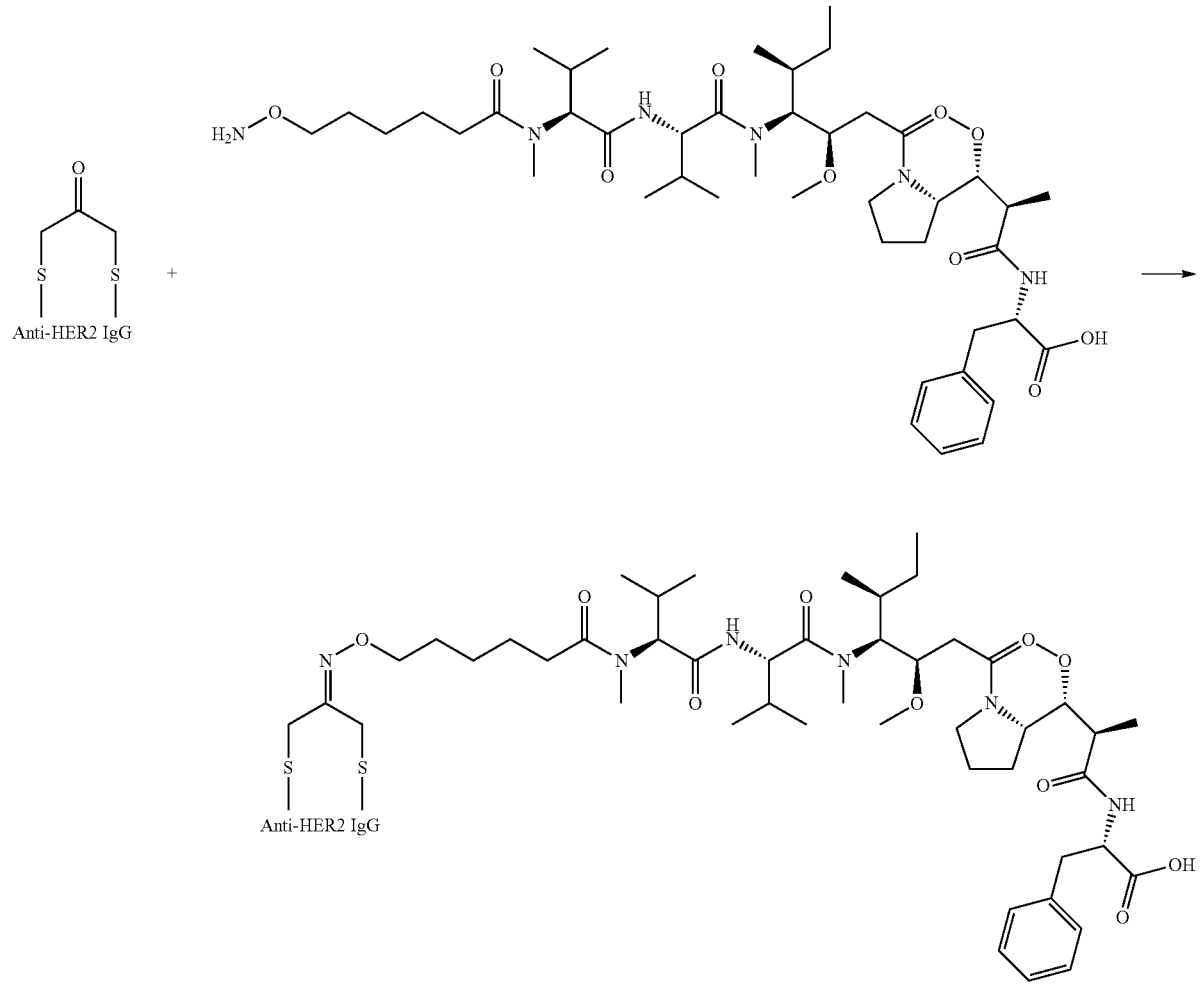

Example 7: Preparation of Antibody B-DM1 Conjugate

Step 1:

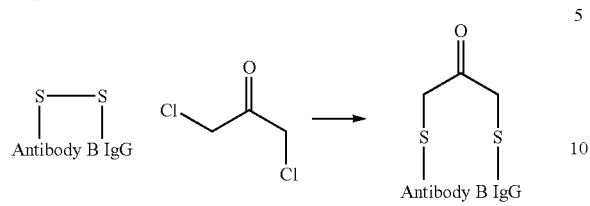

Into a solution of dichloroacetone (7.35 mg, 0.055 mmol, 368 ul) in Tris buffer (4800 ul) was added antibody B IgG (Antibody B IgG recognizes a different antigen from Her2: 68.2 mg, 0.458 μmol, 400 ul), which was cooled to 4° C. for 60 min. TCEP HCl (1.576 mg, 5.50 μmol, 524 ul) at 4° C., which was left for 16 h at 4° C. room. The mixture was concentrated via 10K Amicon® membrane filtration and diluted with PBS. This cycle was repeated by 2 times. After filtration, sample was passed through 5 ml Zeba™ desalting column. Successful modification at inter chain disulfide by 4 acetone formation was confirmed by analysis with PNGase F (New England Biolab) and non reducing/reducing SDS PAGE (4-12% Bis-Tris Gel with colloidal blue staining) performed with samples taken from the reaction solution. LCMS (method B); 146020 (after deglycosylation). Reduced sample for SDS PAGE was prepared following the procedure described before.

Step 2:
PL1 (method A):

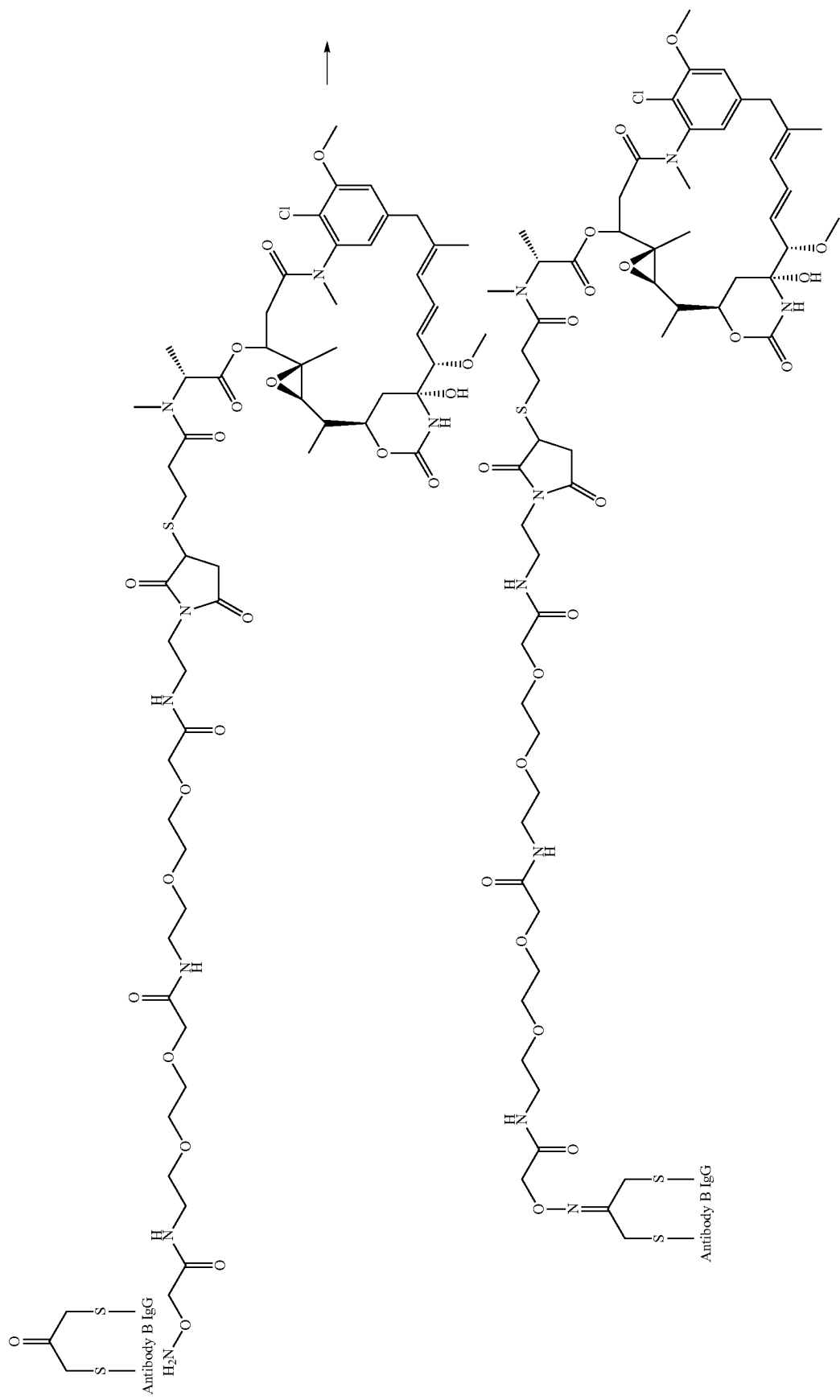

Into a solution of modified Antibody B IgG (48 mg, 0.322 μmol, 1.2 ml) were added DMSO solution of DM-1 derivatives (10.00 mg, 8.05 μmol, 67 ul) and 3,5-diaminobenzoic acid (14.70 mg, 0.097 mmol, 30 ul), which was stirred at 23° C. for 15 h. The mixture was concentrated via 10K Amicon® membrane filtration and diluted with PBS. This cycle was repeated by 3 times. After filtration, sample was passed through 5 ml Zeba™ desalting column. Successful modification of ketones was confirmed by analysis with PNGase F (New England Biolab). DAR was 4 based on LCMS. LCMS (method B); 150915 (after deglycosylation).

PL1 (method B):

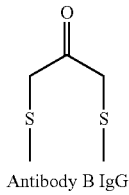

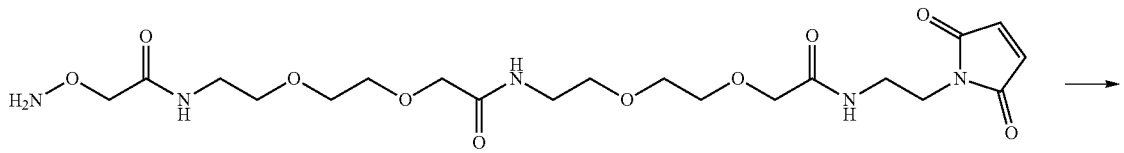

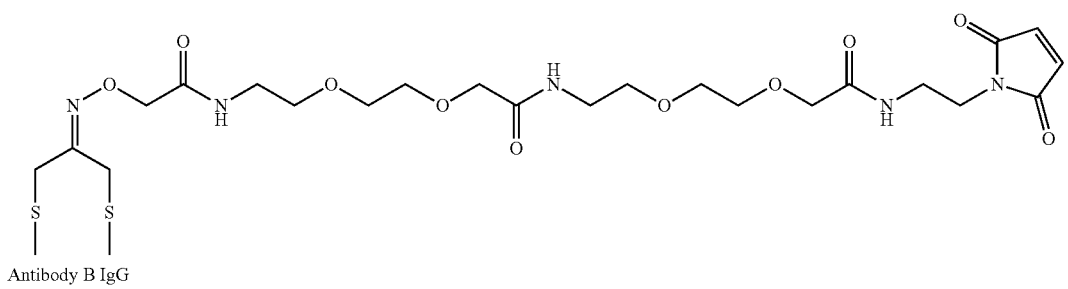

Into a solution of modified Antibody B IgG (679 μg, 0.0046 μmol) in 0.1M Na phosphate pH6.0 were added 2-(aminooxy)-N-(1-(2,5-dioxo-2,5-dihydro-1H-pyrrol-1-yl)-4,13-dioxo-6,9,15,18-tetraoxa-3,12-diazaicosan-20-yl)acetamide in DMSO (563 μg, 0.911 μmol, 2.25 ul) at RT, which was stirred for 20 h at 23° C. The reaction mixture was passed through 0.5 ml desalting column eluting with 100 mM HEPES with EDTA 3 times. Introduction of 3.8 maleimide linker/antibody (DAR=3.8) was confirmed by LCMS. LCMS (method B); 147968 (after deglycosylated with PNGase F (New England Biolab)).

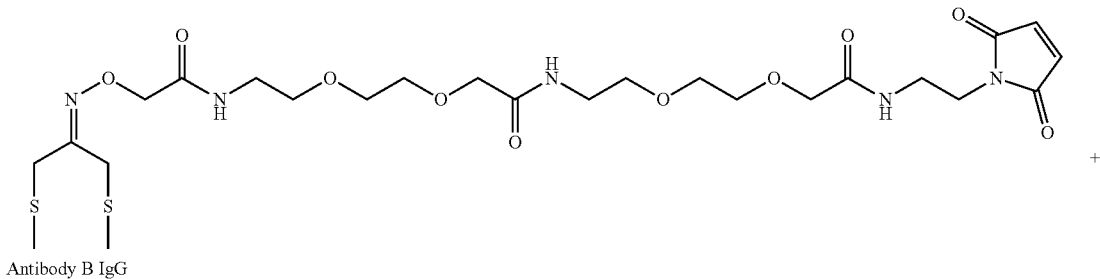

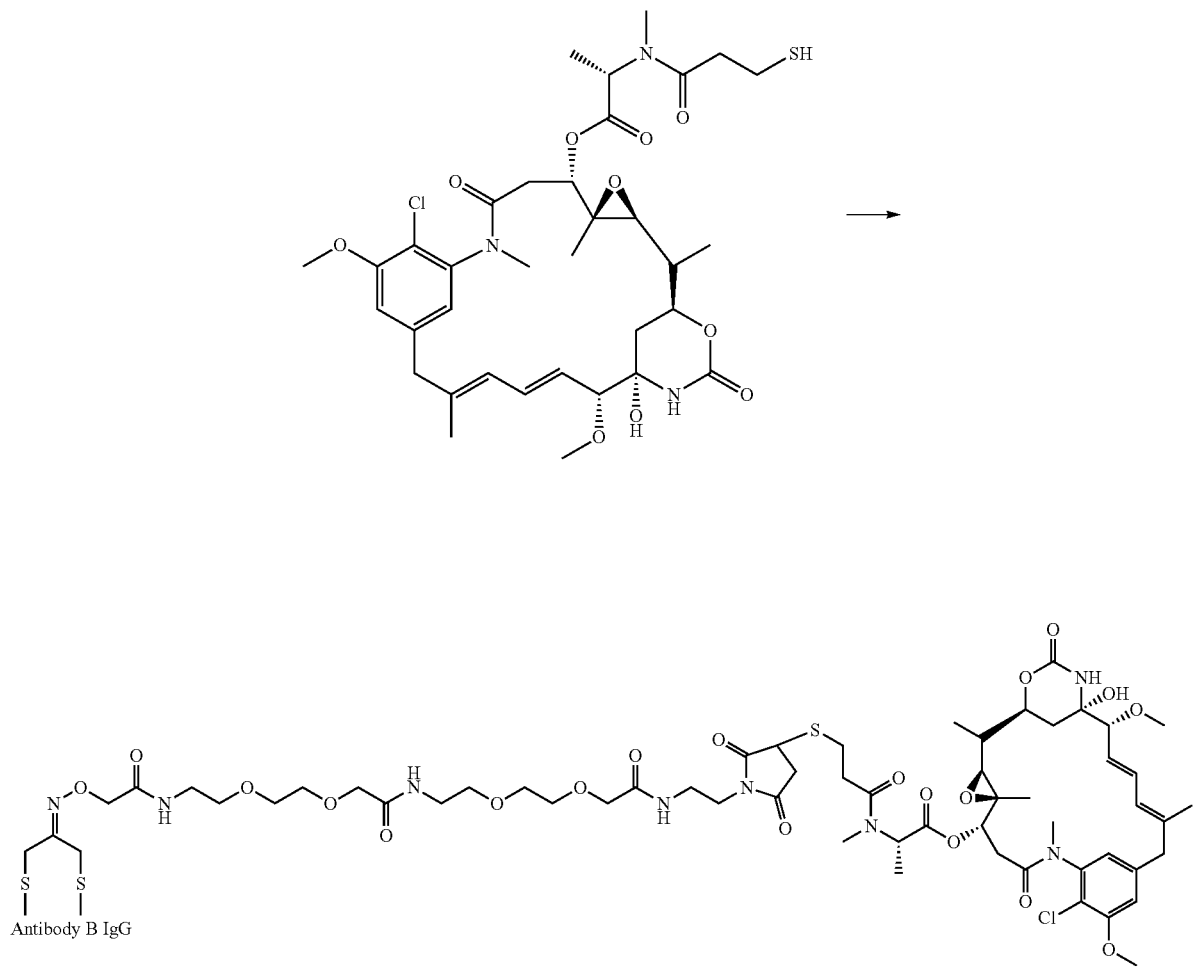

Into a solution of modified Antibody B IgG (177 μg, 0.0012 μmol) in 100 mM HEPES buffer with 10 mM EDTA was added DM-1 in DMSO (8.65 μg, 0.012 μmol, 0.288 ul) at RT, which was agitated for 6 h at 23° C. N-methylmaleimide (1.3 mg/ml in DMSO) (2.083 μg, 0.019 μmol) was added into the reaction solution, which was agitated for 10 min. The reaction mixture was passed through 0.5 mL desalting column eluting 100 mM HEPES buffer. DAR was 3.7 based on LCMS. LCMS (method B); 153967 (DAR4) (glycosylated).

PL2:

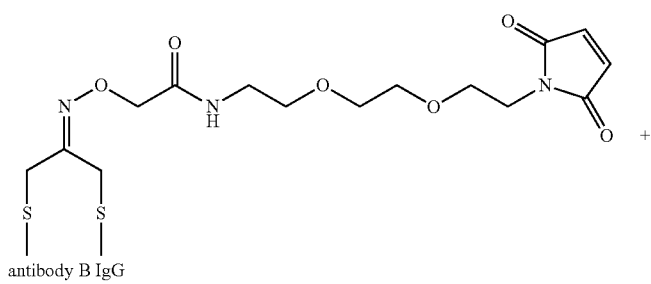

-continued

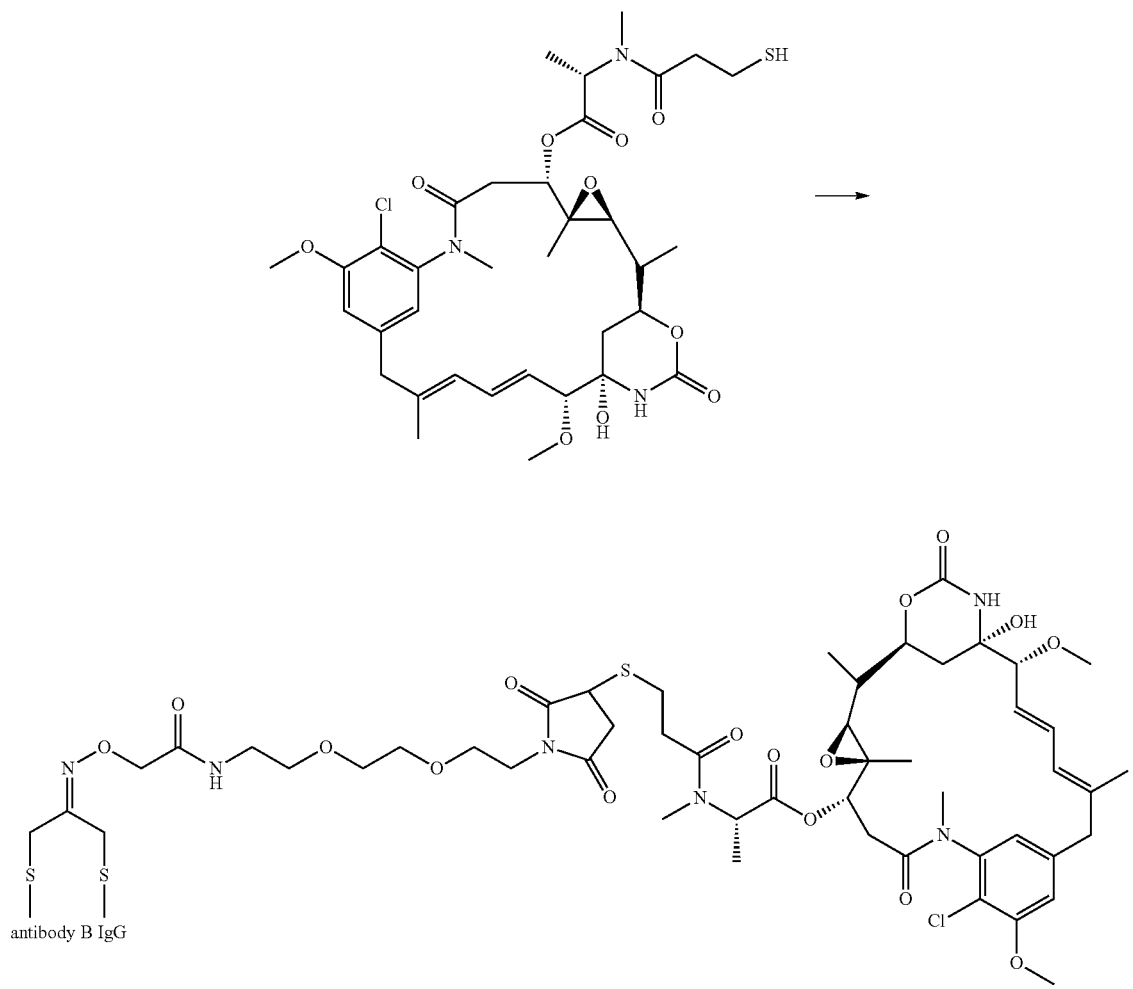

Into a solution of modified Antibody B IgG (420 µg, 0.0028 µmol) in HEPES buffer with 10 mM EDTA was added DM-1 in DMSO (10.61 µg, 0.014 µmol, 0.55 ul) at RT, which was agitated for 8 h at RT. The reaction mixture was passed through 0.5 ml desalting column eluting with 100 mM HEPES with EDTA 3 times. The reaction mixture was passed through 0.5 mL desalting column eluting 100 mM HEPES buffer. DAR was 3.6 based on LCMS. LCMS (method B); 150101 (DAR4) (after deglycosylated with PNGase F (New England Biolab)).

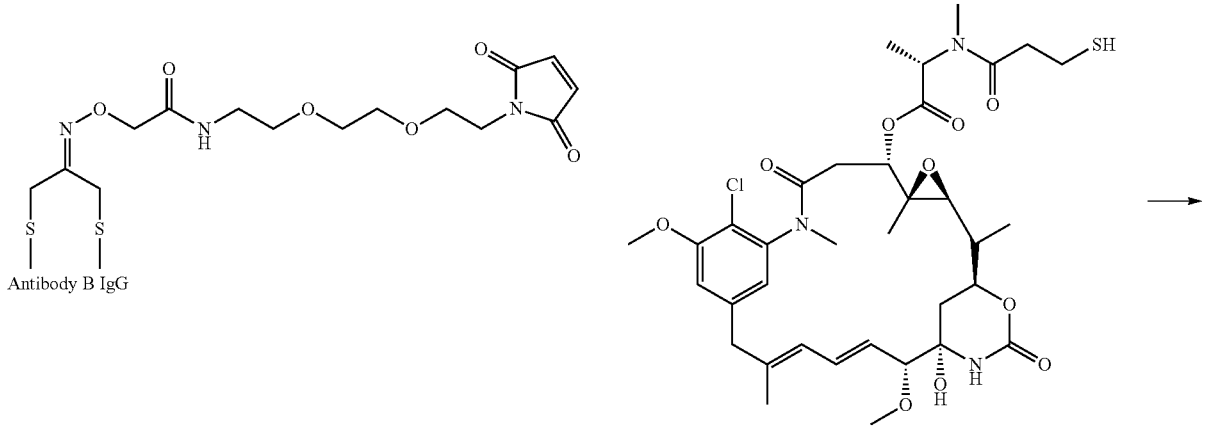

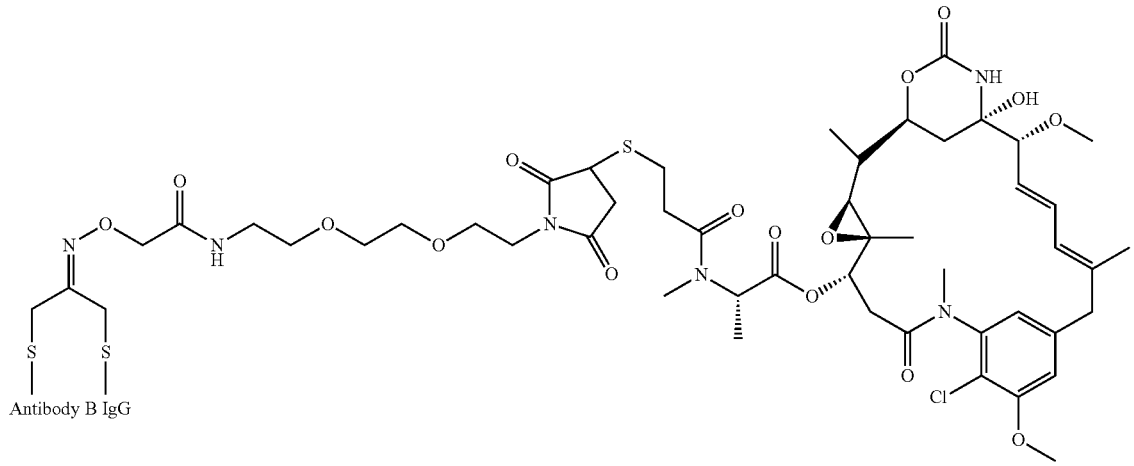

Into a solution of modified Antibody B IgG (420 μg, 0.0028 μmol) in HEPES buffer with 10 mM EDTA was added DM-1 in DMSO (10.61 μg, 0.014 μmol, 0.55 ul) at RT, which was agitated for 8 h at RT. The reaction mixture was passed through 0.5 ml desalting column eluting with 100 mM HEPES with EDTA 3 times. The reaction mixture was passed through 0.5 mL desalting column eluting 100 mM HEPES buffer. DAR was 3.6 based on LCMS. LCMS (method B); 150101 (DAR4) (after deglycosylated with PNGase F (New England Biolab)).

P L3:

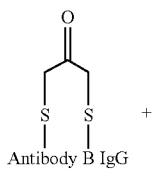

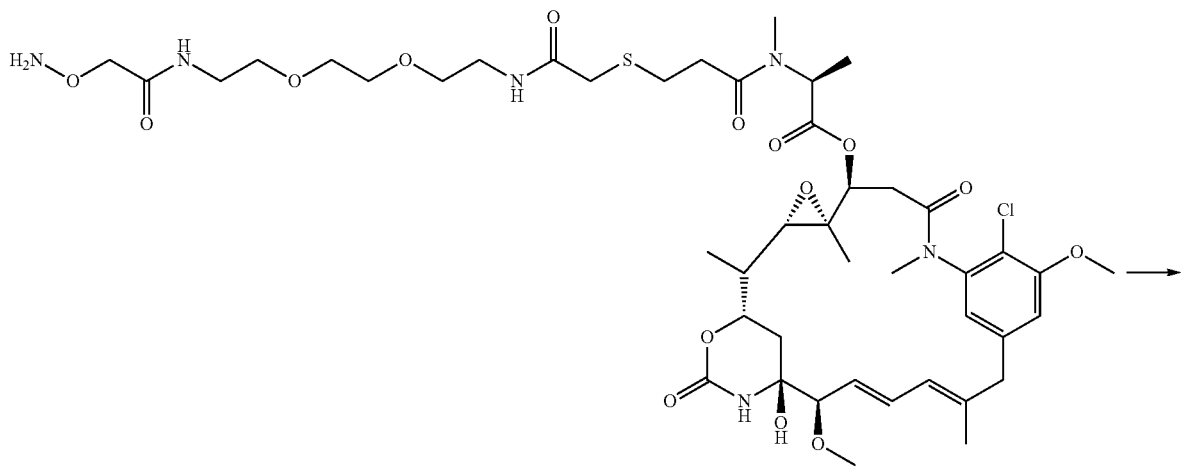

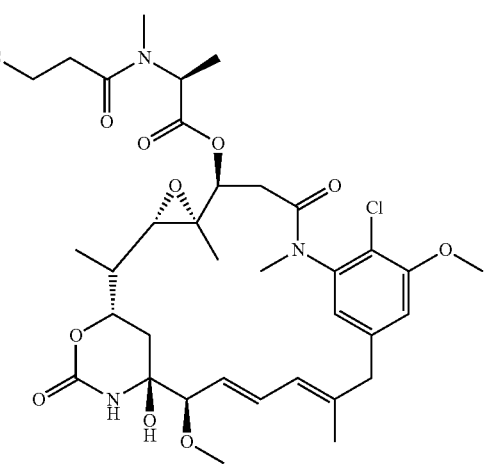

-continued

Into a solution of modified Antibody B IgG (47.3 mg, 0.317 µmol, 1.1 ml) were added DMSO solution of DM-1 derivatives (6.34 mg, 6.35 µmol, 42.3 ul) and 3,5-diaminobenzoic acid (13.52 mg, 0.089 mmol, 27 ul), which was stirred at 23° C. for 15 h. The mixture was concentrated via 10K Amicon® membrane filtration and diluted with PBS. This cycle was repeated by 2 times. After filtration, sample was passed through 5 ml Zeba™ desalting column. Successful modification of ketones was confirmed by analysis with PNGase F (New England Biolab). DAR was 4 based on LCMS. LCMS (method B); 150910 (after deglycosylation).

P L4:

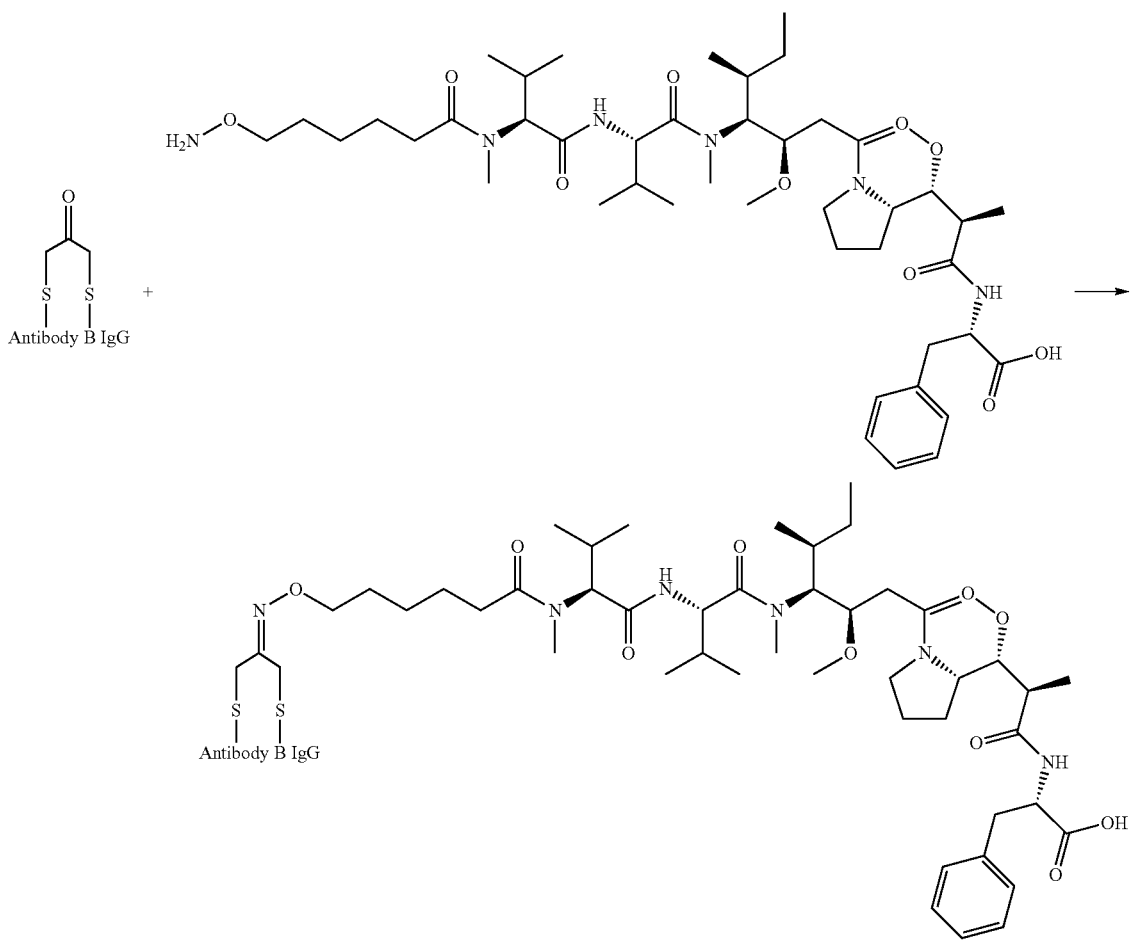

PL4

Into a solution of modified Antibody B IgG (250 μg, 0.0017 μmol, 10 ul) in PBS were added the required alkoxyamine shown above (21.66 μg, 0.025 μmol, 0.245 ul) and 3,5-diaminobenzoic acid (383 μg, 2.52 μmol, 0.43 ul) at RT, which was agitated for 24 h at 23° C. The reaction mixture was passed through 0.5 mL desalting column twice eluting with PBS. DAR was 4 based on LCMS. LCMS (method B); 152446 (glycosylated).

PL1 synthesis:

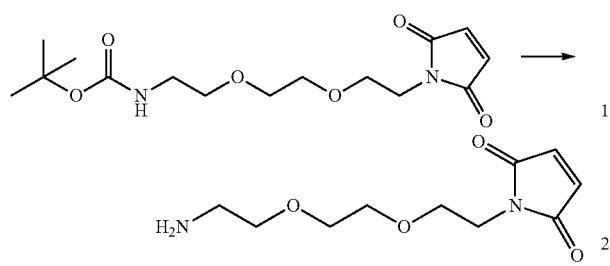

tert-butyl (2-(2-(2-(2,5-dioxo-2,5-dihydro-1H-pyrrol-1-yl)ethoxy)ethoxy)ethyl)carbamate (245 mg, 0.746 mmol) was dissolved in 4N HCl in dioxane (2 mL, 8.00 mmol) at RT, which was stirred for 1 h at RT. After removal of solvent, the crude was used for next reaction without further purification.

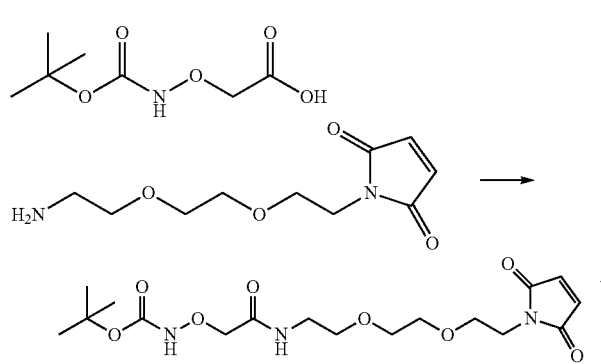

into a solution of 2-(((tert-butoxycarbonyl)amino)oxy) acetic acid (185 mg, 0.970 mmol) and TEA (0.520 mL, 3.73 mmol) in DCM (8 mL) were added EDC (172 mg, 0.895 mmol) and HOBT (114 mg, 0.746 mmol) at RT, which was stirred for 5 min at RT. 1-(2-(2-(2-aminoethoxy)ethoxy)ethyl)-1H-pyrrole-2,5-dione (197 mg, 0.746 mmol) in DCM (4 mL) was added into the above reaction mixture. After stirring for 1 h, DCM and water were added. The organic layer was separeted. The aqueous layer was extracted with DCM. The combined organic layer was dried over $Na_2SO_4$, filtered and concentrated in vacuo. RP-HPLC purification eluting 15-65% MeCN/water with 0.1% TFA gave tert-butyl 2-((2-(2-(2-(2,5-dioxo-2,5-dihydro-1H-pyrrol-1-yl)ethoxy)ethoxy)ethyl)amino)-2-oxoethoxycarbamate (62 mg, 0.154 mmol, 20.70% yield for 2 steps) as a colorless oil. ESI-MS (method A) m/z: 402[M+1]+, Retention time: 1.60 min. $^1$H-NMR ($CDCl_3$-d, 400 MHz); 1.48 (s, 9H), 3.49-3.75 (m, 14H), 6.71 (s, 2H).

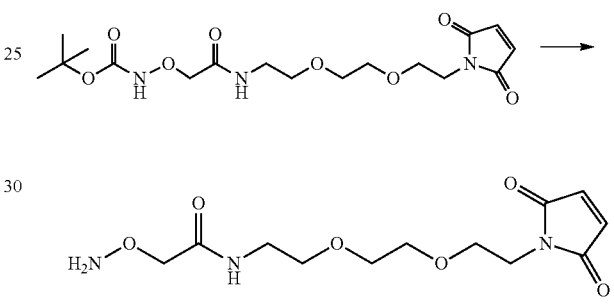

Into a solution of tert-butyl 2-((2-(2-(2-(2,5-dioxo-2,5-dihydro-1H-pyrrol-1-yl)ethoxy)ethoxy)ethyl)amino)-2-oxoethoxycarbamate (62 mg, 0.154 mmol) in DCM (400 μl) was added TFA (400 μl) at RT, which was stirred for 1 h at RT. After removal of solvent, the crude was put in vacuum for O.N. used without further purification. ESI-MS (method A) m/z: 302[M+1]$^+$ PL2 synthesis:

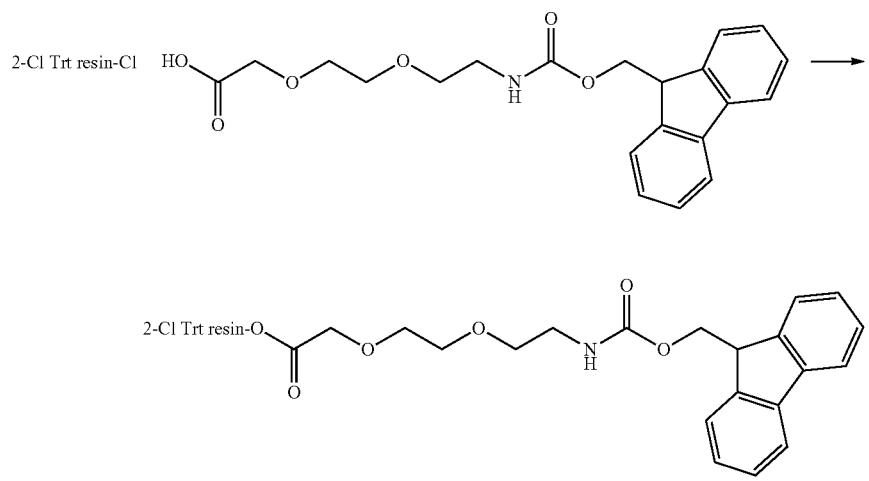

Into a suspension of 2-Cl Trt resin (1.70 mmol/g) (0.086 g, 1.7 mmol) and 1-(9H-fluoren-9-yl)-3-oxo-2,7,10-trioxa-4-azadodecan-12-oic acid (2 g, 5.19 mmol) in DCM (8 mL)/DMF (4 mL) was added DIPEA (2.67 mL, 15.30 mmol) dropwise, which was stirred for 15 h at RT. Solvent was drained. The resin was rinsed with DCM/MeOH/DIPEA (17/2/1, 40 ml), DCM (8 mL*2), DMF (8 mL*2), DCM (8 mL*2) and dried in vacuo.

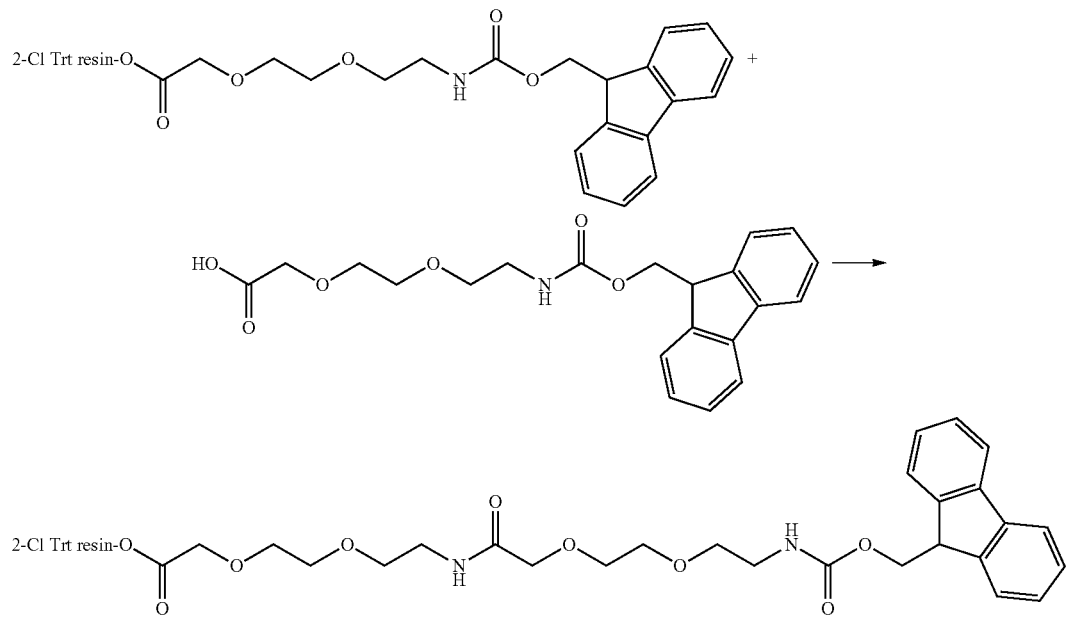

Resin (0.679 g, 1.7 mmol) was charged into reaction vessel. 5 mL of 20% Piperidine in DMF was added, which was stirred gently for 1 min and removed. Another 10 mL of 20% Piperidine in DMF was added, waited for 20 min with intermittent stirring and removed. DMF (10 ml) was added, stirred for 15 s and removed via vacuum filtration. Repeated this step four times (check with Kaiser test; positive, violet-deep blue). Solution of HOAt (0.463 g, 3.40 mmol) and 2-(((tert-butoxycarbonyl)amino)oxy)acetic acid (0.650 g, 3.40 mmol) in DMF (8 mL) was added into resin and DIC (0.530 mL, 3.40 mmol) in DMF (4 mL) was added, reaction mixture was agitated for 1.5 h at RT. Resin was filtered off, rinsed with DMF (10 ml) four times and dried in vacuo.

Resin (0.926 g, 1.7 mmol) was charged into reaction vessel. 5 mL of 20% Piperidine in DMF was added, which was stirred gently for 1 min and removed. Another 10 mL of 20% Piperidine in DMF was added, waited for 20 min with intermittent stirring and removed. DMF (10 ml) was added, stirred for 15 s and removed via vacuum filtration. Repeated this step four times (check with Kaiser test; positive, violet-deep blue). Solution of HOAt (0.463 g, 3.40 mmol) and 2-(((tert-butoxycarbonyl)amino)oxy)acetic acid (0.650 g, 3.40 mmol) in DMF (8 mL) was added into resin and DIC (0.530 mL, 3.40 mmol) in DMF (4 mL) were added. The reaction mixture was agitated for 1.5 h at RT. Resin was filtered off, rinsed with DMF (10 ml) four times and dried in vacuo.

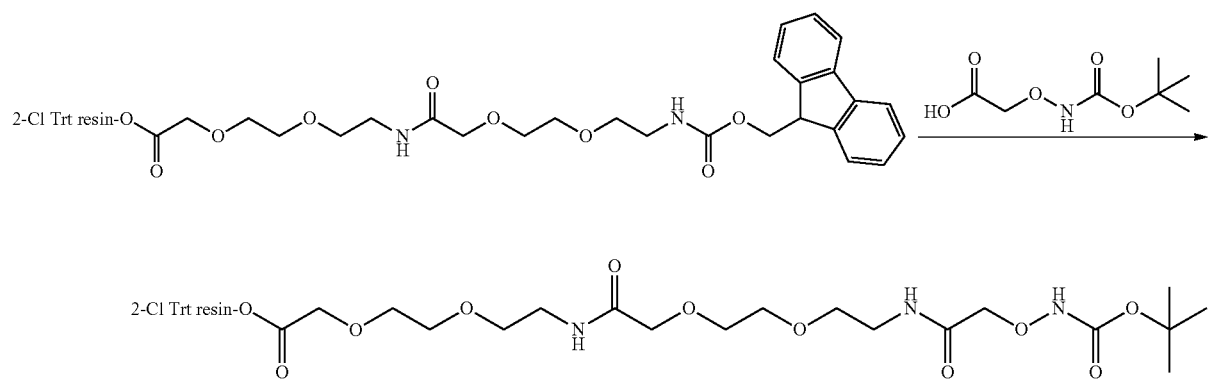

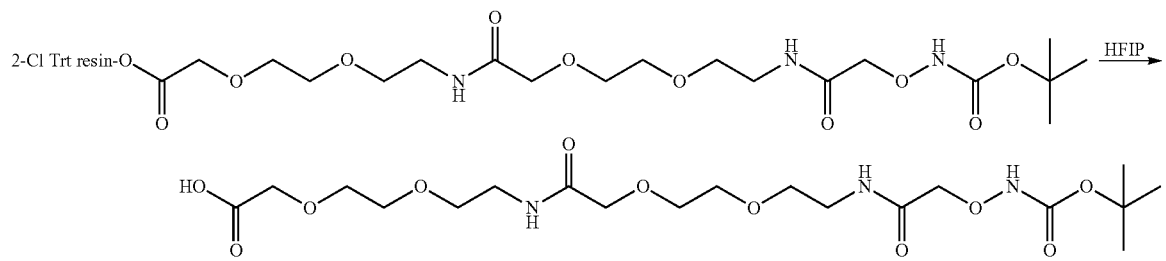

Resin was suspended with 30% HFIP (hexafluoroisopropanol) in CHCl₃ (20 mL, 1.700 mmol), which was agitated for 2 h at RT. Solvent drained was concentrated to give crude 2,2-dimethyl-4,8,17-trioxo-3,6,12,15,21,24-hexaoxa-5,9,18-triazahexacosan-26-oic acid (1.13 g, 2.347 mmol, 138% yield). This was used for the next reaction without further purification. ESI-MS m/z: 482[M+1]+, Retention time: 1.10 min (method B).

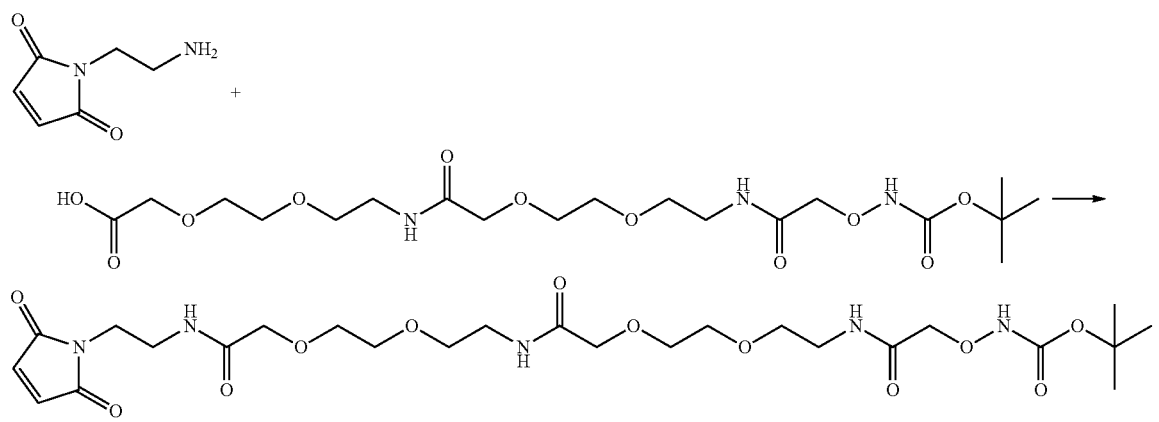

Into a solution of 2,2-dimethyl-4,8,17-trioxo-3,6,12,15,21,24-hexaoxa-5,9,18-triazahexacosan-26-oic acid (819 mg, 1.7 mmol) in DMF (6 mL) were added HOAt (463 mg, 3.40 mmol) and DIC (0.530 mL, 3.40 mmol) at RT respectively, which was stirred for 5 min at RT. Into above mixture were added 1-(2-aminoethyl)-1H-pyrrole-2,5-dione (518 mg, 2.040 mmol) and DIPEA (diisopropyl ethylamine, 0.594 mL, 3.40 mmol) at RT, which was stirred for 1 h at RT. The reaction mixture was diluted with water and EtOAc (ethyl acetate). The organic layer was separeted. The aqueous layer was extracted with EtOAc. The combined organic layer was dried over Na₂SO₄, filtered and concentrated in vacuo. The desired compound was mostly in aqueous layer based on LCMS. After lyophilization of aqueous layer. The crude was purified via RP-HPLC eluting 15-70% MeCN/water with 0.1% TFA gave tert-butyl (23-(2,5-dioxo-2,5-dihydro-1H-pyrrol-1-yl)-2,11,20-trioxo-6,9,15,18-tetraoxa-3,12,21-triazatricosyl)oxycarbamate (600 mg, 0.994 mmol, 58.5% yield). ESI-MS m/z: 604[M+1]+, Retention time: 1.14 min (method B). ¹H-NMR (CDCl3-d, 400 MHz); 1.48 (s, 7.5H), 1.55 (s, 1.5H), 3.47-3.71 (m, 20H), 3.97 (s, 2H), 4.04 (s, 2H), 4.37 (s, 1.65H), 4.47 (s, 0.35H), 6.72 (s, 2H).

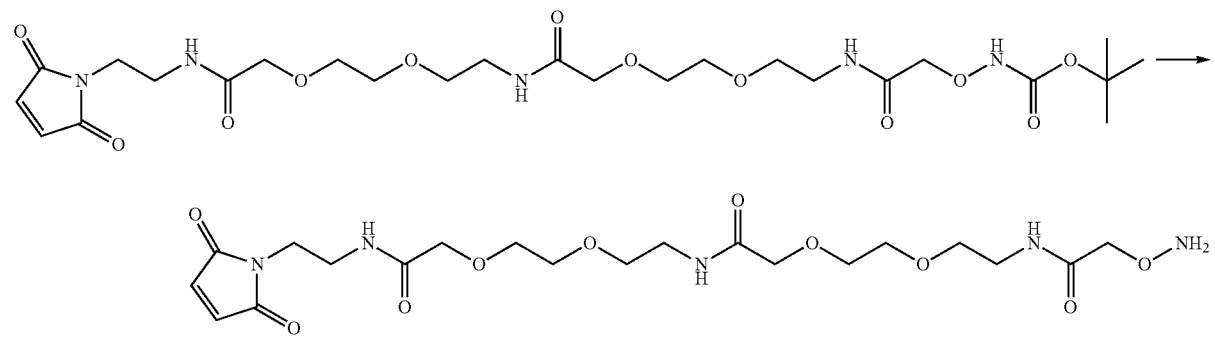

Into a solution of tert-butyl (23-(2,5-dioxo-2,5-dihydro-1H-pyrrol-1-yl)-2,11,20-trioxo-6,9,15,18-tetraoxa-3,12,21-triazatricosyl)oxycarbamate (8.4 mg, 0.014 mmol) in DCM (100 µl) was added TFA (100 µl) at RT, which was agitated for 1 h at RT. Removal of solvent resulted in 2-(aminooxy)-N-(1-(2,5-dioxo-2,5-dihydro-1H-pyrrol-1-yl)-4,13-dioxo-6,9,15,18-tetraoxa-3,12-diazaicosan-20-yl)acetamide. This was used for next reaction without further purification. ESI-MS m/z: 504[M+1]+, Retention time: 0.69 min (method A).

400 MHz); 0.80 (s, 3H), 1.21-1.33 (m, 9H), 1.41-1.51 (m, 1H), 1.56-1.59 (m, 1H), 2.31-2.39 (m, 1H), 2.57-2.65 (m, 2H), 2.79-2.88 (m, 1H), 2.86 (s, 3H), 2.91-3.13 (m, 5H), 3.16-3.24 (m, 1H), 3.20 (s, 3H), 3.36 (s, 3H), 3.43-3.76 (m, 25H), 3.90 (d, J=3.6 Hz, 2H), 3.98 (s, 3H), 4.02 (s, 2H), 4.17 (s, 2H), 4.25-4.32 (m, 1H), 4.77-4.80 (m, 1H), 5.30-5.37 (m, 1H), 5.62-5.69 (m, 1H), 6.26 (s, 1H), 6.38-6.45 (m, 1H), 6.63-6.68 (m, 2H), 6.82-6.84 (m, 1H), 6.92 (brs, 1H), 7.14-7.24 (2H).

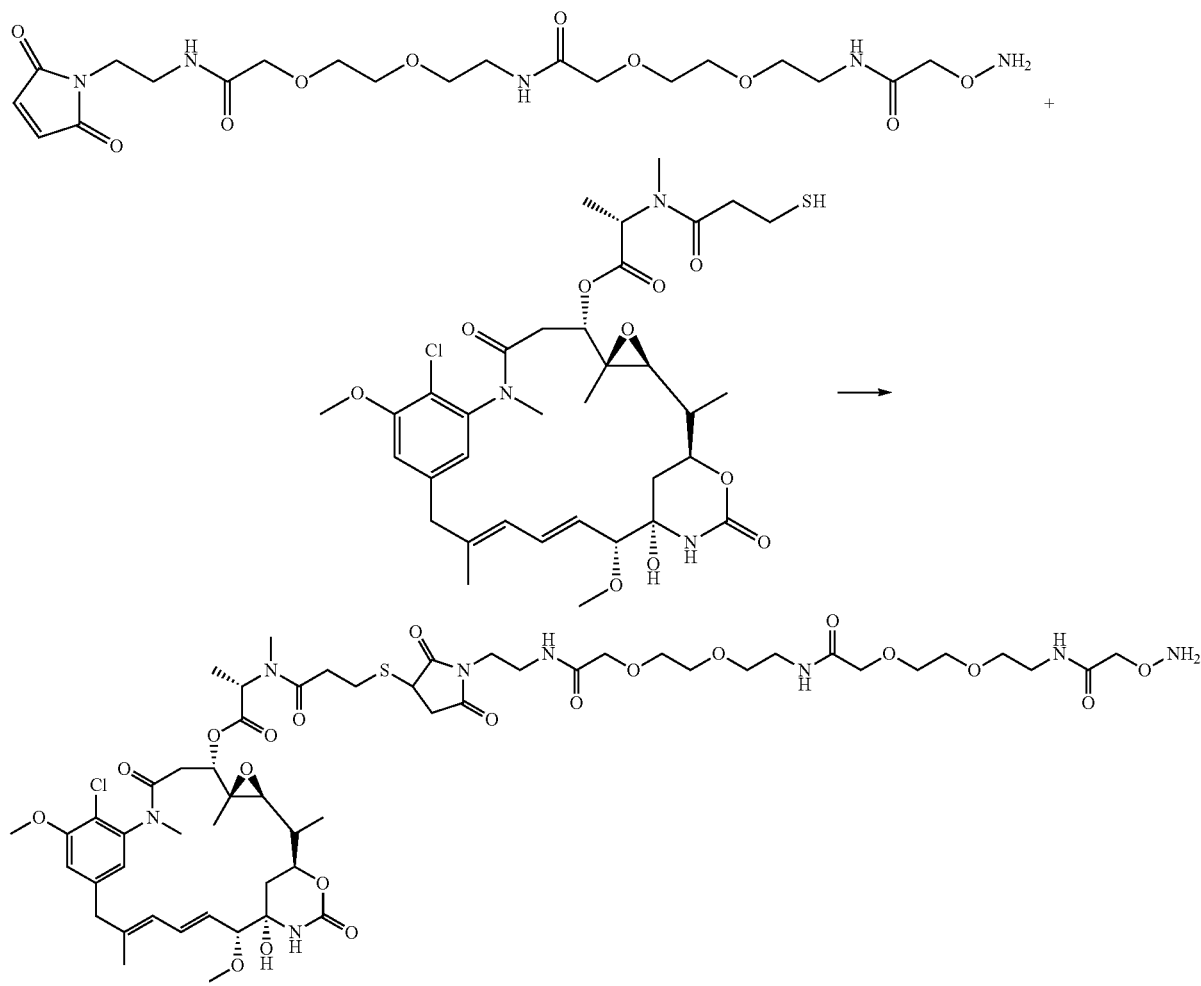

PL2

PL3 synthesis: Into a solution of 2-(aminooxy)-N-(1-(2,5-dioxo-2,5-dihydro-1H-pyrrol-1-yl)-4,13-dioxo-6,9,15,18-tetraoxa-3,12-diazaicosan-20-yl)acetamide (22.79 mg, 0.031 mmol) in DMA (0.6 mL) was added DM-1 (23 mg, 0.031 mmol) and 100 mM Na phosphate pH7.4 (0.600 mL) at 5° C. DIPEA (10.88 µl, 0.062 mmol) was added at the same temperature. This reaction mixture was letting warm to RT and stirred for 1.5 h. The reaction mixture was diluted with DCM and sat. sodium bicarbonate aq. The organic layer was washed with sat.NH$_4$Cl (aq) and brine. The combined organic layer was dried over Na$_2$SO$_4$, filtered and concentrated in vacuo. Silica gel chromatography eluting with 0-15% MeOH/DCM gave the desired compound (21 mg, 0.017 mmol, 54.3% yield). ESI-MS m/z: 1242[M+1]+, Retention time: 1.00 min (method A). $^1$H-NMR (CDCl3-d,

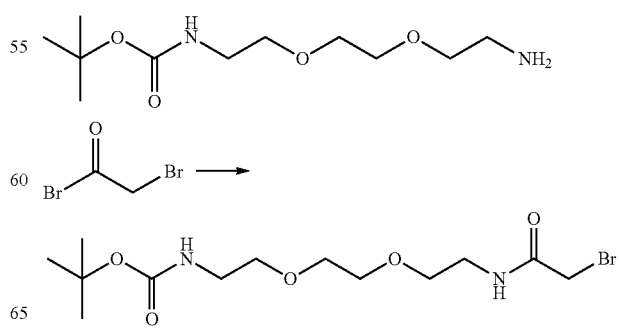

Into a solution of tert-butyl (2-(2-(2-aminoethoxy)ethoxy)ethyl)carbamate (320 mg, 1.289 mmol) in DCM (3 mL) were added 2-bromoacetyl bromide (0.225 mL, 2.58 mmol) and DIPEA (0.563 mL, 3.22 mmol) at 5° C., which was stirred for 15 min letting warm to RT. After removal of solvent, silica gel column chromatography purification eluting 0-40-100% EtOAc/heptane gave tert-butyl (2-(2-(2-(2-bromoacetamido)ethoxy)ethoxy)ethyl)carbamate (317 mg, 0.858 mmol, 66.6% yield). ESI-MS m/z:269[M+1-Boc]+, Retention time: 1.41 min (method A). H-NMR (CDCl3, 400 MHz); 1.45 (s, 9H), 3.34 (brs, 2H, 3.48-3.52 (m, 2H), 3.53-3.60 (m, 4H), 3.63 (s, 4H), 3.88 (s, 2H).

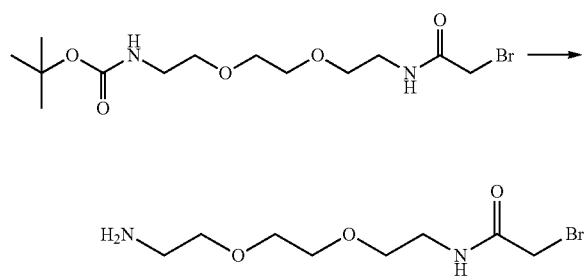

Into a solution of tert-butyl (2-(2-(2-(2-bromoacetamido)ethoxy)ethoxy)ethyl)carbamate (317 mg, 0.858 mmol) in DCM (1 mL) was added TFA (1 mL), which was stirred for 30 min at RT. After removal of solvents, the resulting crude was used for next reaction without further purification.

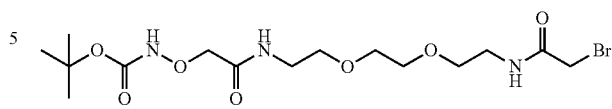

Into a solution of N-(2-(2-(2-aminoethoxy)ethoxy)ethyl)-2-bromoacetamide (329 mg, 0.858 mmol) in DCM (1.5 mL) were added pre-activated ester (prepared from 2-(((tert-butoxycarbonyl)amino)oxy)acetic acid (328 mg, 1.716 mmol), HOAt (175 mg, 1.287 mmol) and DIC (0.267 mL, 1.716 mmol) in DMF (1.5 mL) being stirred for 5 min at RT) and DIPEA (0.749 mL, 4.29 mmol) at 5° C., which was stirred for 20 min letting warm to RT. EtOAc and water was added. The organic layer was separeted, the aqueous layer was extracted with EtOAc. The combined organic layer was dired over Na2SO4, filtered and concentrated in vacuo. Silicagel chromatography purification eluting 0-5% MeOH/DCM tert-butyl (14-bromo-2,13-dioxo-6,9-dioxa-3,12-diazatetradecyl)oxycarbamate (150 mg, 0.339 mmol, 39.5% yield). ESI-MS m/z:343[M+1-Boc]+, Retention time: 1.30 min ((method A). H-NMR (CDCl₃, 400 MHz); 1.49 (s, 9H), 3.47-3.55 (m, 4H), 3.59-3.63 (m, 4H), 3.65 (s, 4H), 3.88 (s, 2H), 4.34 (s, 2H).

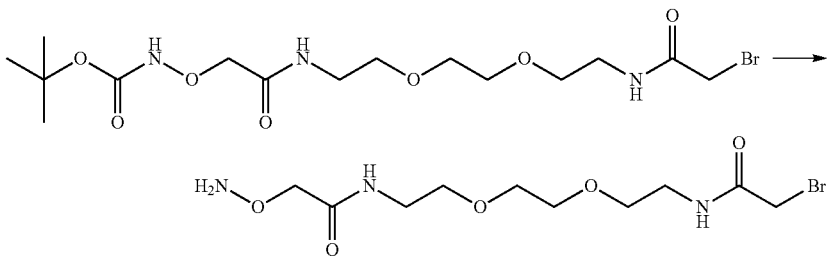

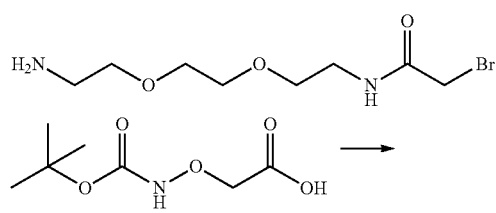

tert-butyl (14-bromo-2,13-dioxo-6,9-dioxa-3,12-diazatetradecyl)oxycarbamate (150 mg, 0.339 mmol) was dissolved in DCM (Volume: 1 mL, Ratio: 1.000), into which was added TFA (Volume: 1, Ratio: 1.000) at RT. This reaction mixture was stirred for 30 min at RT. After removal of solvent, RP-HPLC eluting with 10-25% MeCN/water containing 0.1% TFA gave 2-(aminooxy)-N-(2-(2-(2-(2-bromoacetamido)ethoxy)ethoxy)ethyl)acetamide (110 mg, 0.241 mmol, 71.1% yield). ESI-MS m/z: 344[M+2]+, Retention time: 0.44 min (method A).

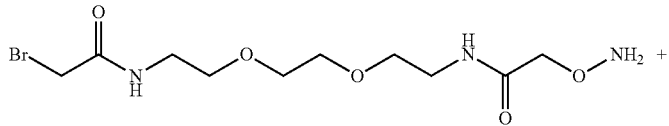

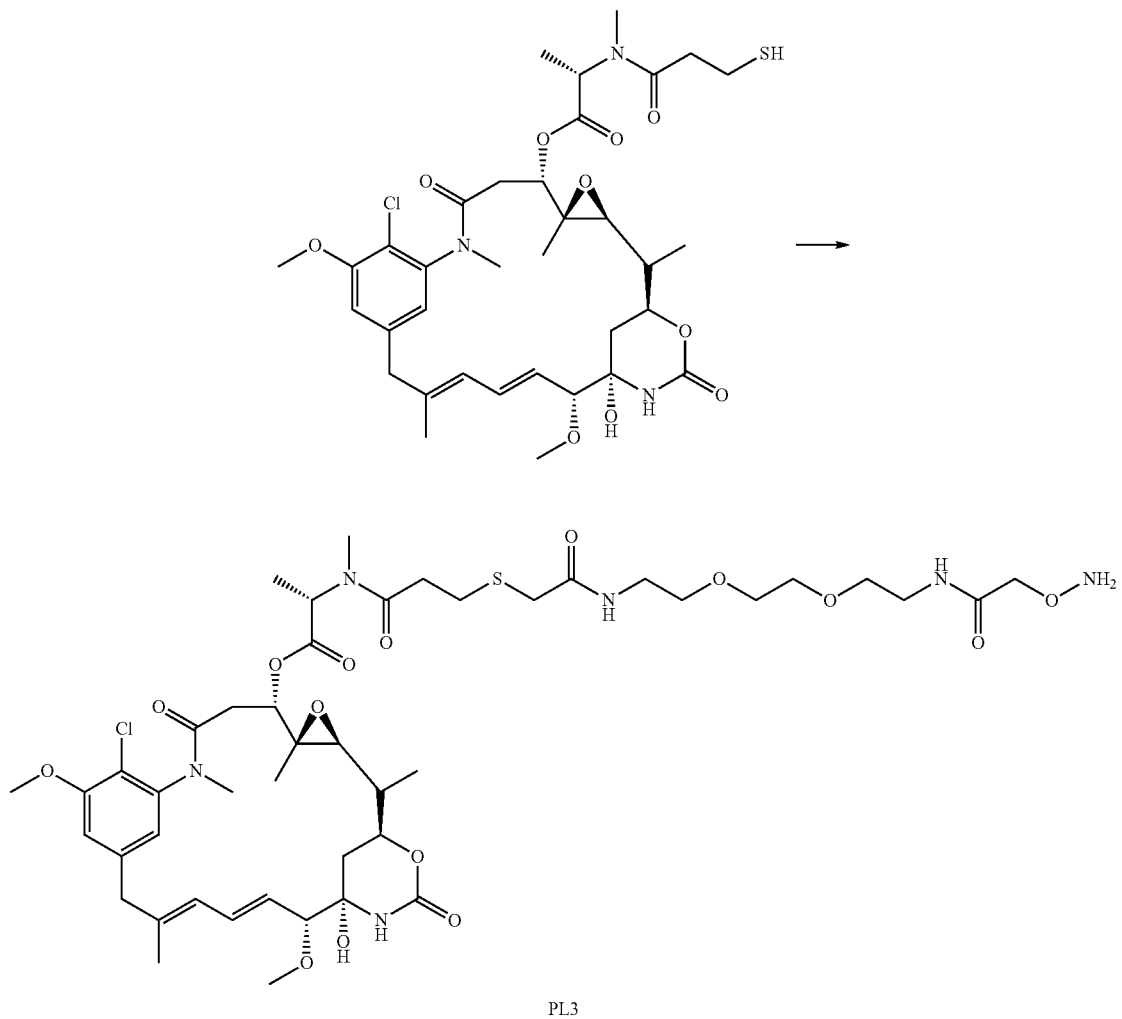

PL3

Into a solution of 2-(aminooxy)-N-(2-(2-(2-(2-bromoacetamido)ethoxy)ethoxy)ethyl)acetamide (42.9 mg, 0.075 mmol) in DMA (1 mL) was added DM-1 (37 mg, 0.050 mmol) and 75 mM Na phosphate pH8.5 (1 mL) at 5° C. DIPEA (0.026 mL, 0.150 mmol) was added at the same temperature. This reaction mixture was letting warm to RT and stirred for 1 h. reaction mixture was diluted with DCM and sat. sodium bicarbonate aq., and the organic layer was washed with sat.NH$_4$Claq and brine combined organic layer was dried over Na$_2$SO$_4$, filtered and concentrated in vacuo. Silica gel chromatography eluting with 0-15% MeOH/DCM gave the desired compound (31 mg, 0.031 mmol, 61.9% yield). ESI-MS m/z: 1000[M+1]+, Retention time: 1.61 min (method A). $^1$H-NMR (CDCl3-d, 400 MHz); 0.79 (s, 3H), 1.20-1.33 (m, 9H), 1.41-1.50 (m, 2H), 2.17-2.22 (m, 1H), 2.50-2.63 (m, 2H), 2.70-2.81 (m, 2H), 2.86-2.94 (m, 3H), 2.99-3.01 (m, 1H), 3.10-3.13 (m, 1H), 3.18-3.20 (m, 4H), 3.36 (s, 3H), 3.45-3.62 (m, 14H), 3.98 (s, 3H), 4.17 (s, 2H), 4.25-4.31 (m, 1H), 4.78-4.82 (m, 1H), 5.30-5.35 (m, 1H), 5.63-5.69 (m, 1H), 6.27 (s, 1H), 6.39-6.45 (m, 1H), 6.61-6.64 (m, 2H), 6.83 (s, 1H), 6.87 (brs, 1H).

Example 8: Antibody C Fab Conjugate

Step 1:

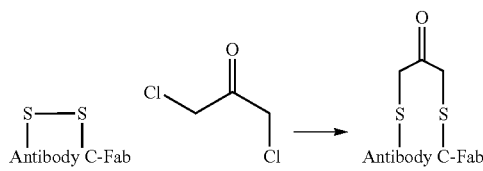

Into a solution of Antibody C Fab (Antibody C binds a different target antigen from Her2 and Antibody B: 1668 µg, 0.035 µmol, 120 ul) in 100 mM Na phosphate with EDTA, pH7.4 was added TCEP HCl (35.2 µg, 0.123 µmol, 11.73 ul) at RT, which was agitated for 1.5 h at 23° C. 1,3-dichloropropan-2-one (117 µg, 0.878 µmol, 5.85 ul) was added into the reaction mixture, which was agitated for 40 min at 23° C. 1 acetone bridge modification was observed by LCMS. The reaction mixture was passed through 0.5 desalting column eluting with 100 mM NaOAc buffer pH5.2. LCMS (method B); 47554.

Step 2:

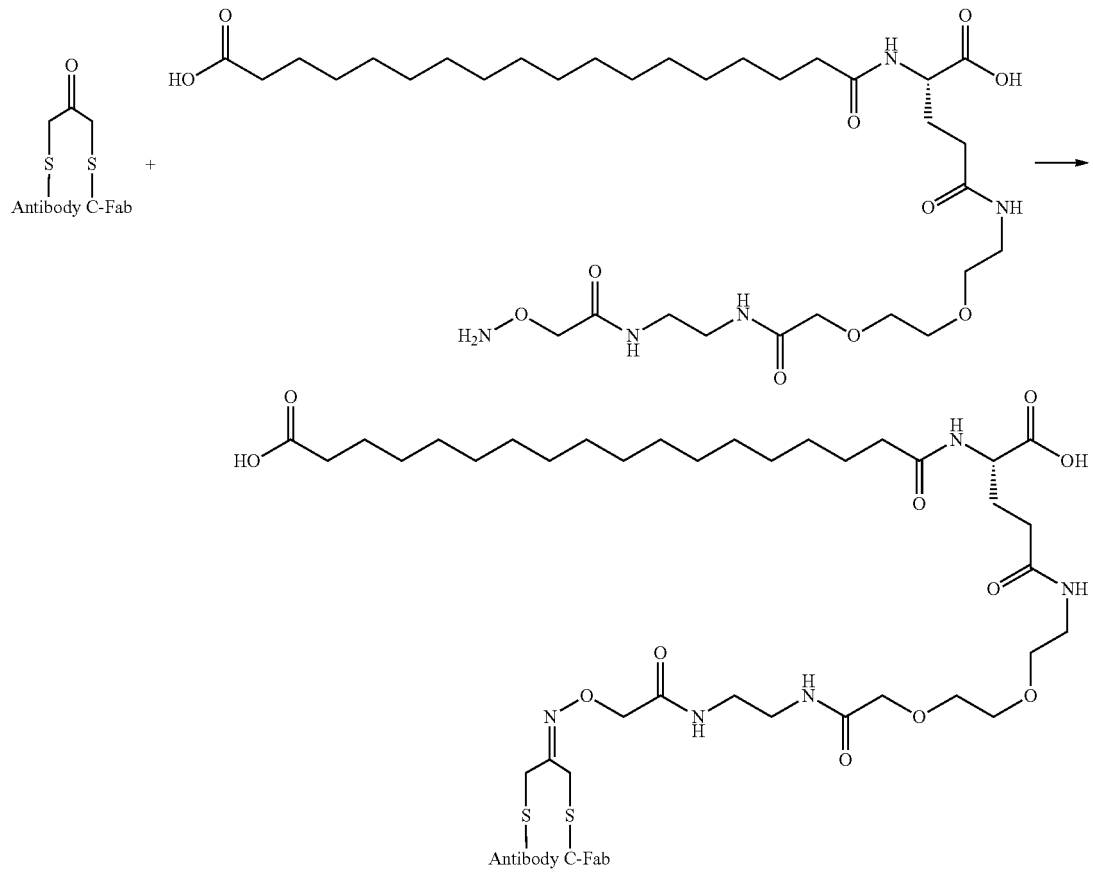

Into a solution of modified Antibody C Fab (1668 μg, 0.035 μmol, 148 ul) in 100 mM NaOAc buffer pH5.2 and the aminooxy-substituted fatty acid shown (1852 μg, 2.63 μmol) was added 3,5-diaminobenzoic acid (694 μg, 4.56 μmol, 5.34 ul) at RT, which was agitated for 20 h at 23° C. Additional aminooxy-fatty acid (1852 μg, 2.63 μmol) was added into the mixture, which was agitated for 24 h at RT. The reaction mixture was passed through 5 ml desalting column eluting with PBS pH7.4 to give the expected Antibody C Fab-fatty acid conjugate (30% yield). LCMS (method B); 48238.

Figure 9:
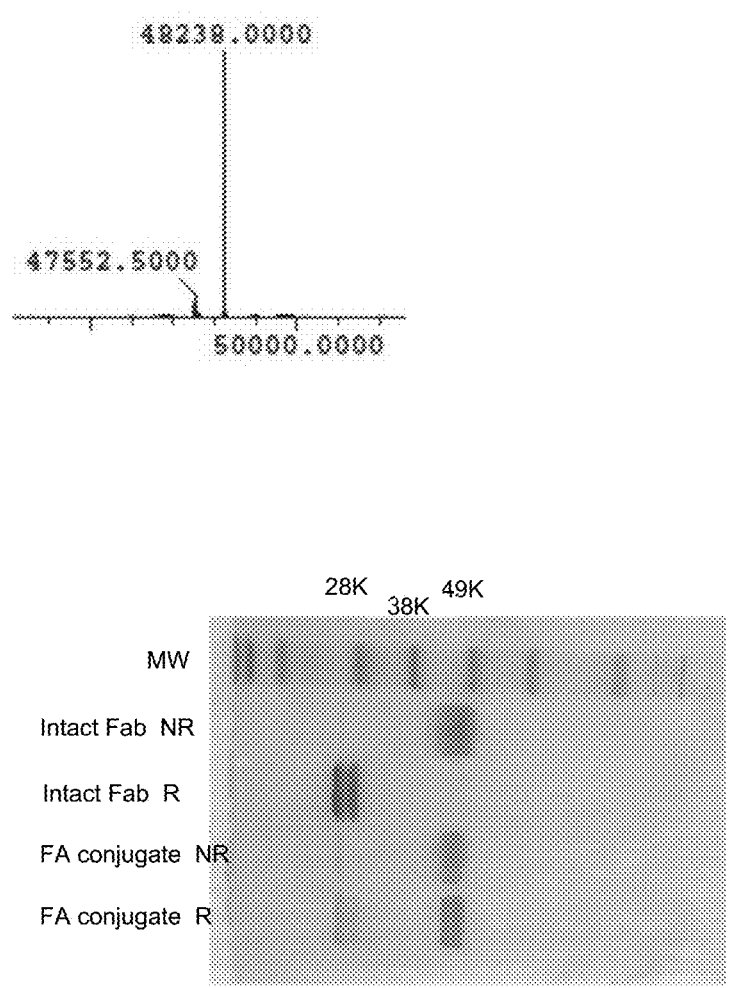
FIG. 9 shows SDS PAGE gel and LC-MS data for the product of Example 8.

SDS PAGE image and mass spectrum for the conjugate are provided in FIG. 9.

Example 9: Effect of Order of Addition of Dichloroacetone and TCEP

All reactions were run at 25° C., using 50 mM buffer (TRIS unless otherwise specified) at pH 8.0. The reactions were run with (58.8 microliters) and buffer (20 microliters of 1M buffer) in a well, then adding IgG1 (6.6 microliters of a solution containing 170.5 mg/mL) and TCEP (8.6 microliters of an aqueous solution with 3 mg/mL TCEP). After waiting for the time period indicated, 1,3-dichloroacetone (6 microliters of a solution with 20 mg/mL in DMSO) was added.

In a first series of experiments, reactions were run by adding the reducing agent (TCEP-HCl) first, and adding 1,3-dichloroacetone one hour later. Product distribution was analyzed by Microchip electrophoresis-SDS method after reduction of the product mixture by DTT or TCEP (Electrophoresis 2012, vol. 33, 765-72). The results are shown in the following table: LC=light chain, HC=heavy chain, HL=heavy+light chain, HH=heavy chain+heavy chain; HHL=HC+HC+LC; and LHHL=LC+HC+HC+LC. The data shows that the major product is an HC-LC (heavy chain-light chain) adduct, after reduction to cleave any remaining disulfides. This demonstrates that only partial reaction occurred under these conditions. The data also demonstrates that the reaction was essentially done within the first half hour.

| Sample Name | Rel. Area % LC | Rel. Area % HC | Rel. Area % HL | Rel. Area % HH | Rel. Area % HHL | Rel. Area % LHHL |
|---|---|---|---|---|---|---|
| TCEP first t = 0.5 h | 3.3 | 5.4 | 50.9 | 0.6 | 6.5 | 33.3 |
| TCEP first t = 1 h | 3.2 | 4.7 | 51.9 | 0.8 | 5.9 | 33.6 |
| TCEP first t = 1.5 h | 2.9 | 4.6 | 50.1 | 0.6 | 6.4 | 35.5 |
| TCEP first t = 2 h | 3.0 | 4.5 | 51.8 | 0.7 | 6.0 | 33.9 |

-continued

| Sample Name | Rel. Area % LC | Rel. Area % HC | Rel. Area % HL | Rel. Area % HH | Rel. Area % HHL | Rel. Area % LHHL |
|---|---|---|---|---|---|---|
| TCEP first t = 3 h | 2.9 | 4.0 | 52.2 | 0.6 | 6.1 | 34.2 |
| TCEP first t = 17 h | 2.7 | 4.5 | 50.6 | 0.8 | 6.4 | 35.0 |

A second set of experiments were run under the same conditions, except that 1,3-dichloroacetone was added to the polypeptide/buffer reaction mixture before the addition of the reducing agent. The results from these experiments are shown in the following table, which shows a significant increase in LHHL, corresponding to conversion of at least three of the four disulfides of the antibody into covalent linkages formed by reaction of 1,3-dichloroacetone with both sulfur atoms from the disulfide. Again, the reaction appears to be essentially complete within 30 minutes.

| Sample Name | Rel. Area % LC | Rel. Area % HC | Rel. Area % HL | Rel. Area % HH | Rel. Area % HHL | Rel. Area % LHHL |
|---|---|---|---|---|---|---|
| Dichloroacetone first t = 0.5 h | 2.83 | 0.82 | 7.13 | 0.98 | 13.01 | 75.23 |
| Dichloroacetone first t = 1 h | 2.95 | 0.72 | 6.94 | 1.17 | 13.42 | 74.81 |
| Dichloroacetone first t = 1.5 h | 2.64 | 0.61 | 6.42 | 1.09 | 13.61 | 75.63 |
| Dichloroacetone first t = 2 h | 2.63 | 0.61 | 6.43 | 1.08 | 13.49 | 75.77 |
| Dichloroacetone first t = 3 h | 2.38 | 0.51 | 6.4 | 1.07 | 13.41 | 76.23 |
| Dichloroacetone first t = 17 h | 2.47 | 0.56 | 5.94 | 1.04 | 13.39 | 76.59 |

These experiments demonstrate that adding dichloroacetone before initiating the reduction of the disulfides provides a surprisingly large increase in efficiency of the sulfhydryl-to-sulfhydryl crosslinking reaction. Product yields were lower with PBS as buffer.

In separate experiments, it was demonstrated that increasing the amount of dichloroacetone used by ten-fold hindered the reaction, and that reducing the pH to 7.40, 7.10, 6.80 and 6.60 resulted in similar or slightly improved yields of the LHHL product.

Example 10: Screen of Buffers

Reactions were run by addition of the reducing agent (TCEP-HCl) to a premixed solution of 1,3-dichloroacetone and IgG in buffer (100 mM) at room temperature. Product distribution was analyzed by Microchip electrophoresis-SDS method after reduction of the product mixture by DTT or TCEP after 7 h. The results are shown in the following table: LC=light chain, HC=heavy chain, HL=heavy+light chain, HH=heavy chain+heavy chain; HHL=HC+HC+LC; and 'Intact'=(HC)$_2$(LC)$_2$; LHHL=LC+HC+HC+LC. The yield was derived from the percentage of LHHL.

| measured pH | buffer | Reaction yield [%] |
|---|---|---|
| 7 | Bis-TRIS | 87.7 |
| 6.9 | Bis-TRIS-Propane | 87.4 |
| 6.5 | Succinate | 75.8 |
| 6.8 | ADA | 86.2 |
| 6.8 | Imidazole | 85.5 |
| 7.4 | TRIS | 86.5 |
| 6.6 | MES | 85.0 |
| 6.6 | Citrate | 79.6 |
| 6.6 | PIPES | 83.3 |
| 6.6 | MOPS | 86.9 |
| 7.2 | Tricine | 86.8 |
| 6.3 | TES | 85.9 |
| 6.3 | HEPES | 82.7 |
| 7.1 | EPPS | 84.3 |
| 7.1 | Bicine | 86.5 |
| 7 | PBS50/TRIS50 | 86.5 |
| 7.1 | TAPS | 85.1 |
| 6.8 | Glyclglycine | 86.6 |
| 6.5 | PBS75/TRIS25 | 86.1 |
| 6.1 | PBS90/TRIS10 | 84.7 |
| 8.7 | Carbonate | 67.8 |

The invention claimed is:

1. A method for converting a ketone-modified polypeptide into an oxime-modified polypeptide, the method comprising:
   converting a polypeptide comprising a reducible disulfide bond into a ketone-modified polypeptide, which comprises adding a reducing agent capable of reducing a disulfide bond to a mixture comprising a polypeptide containing a reducible disulfide bond, an aqueous buffer, and 1,3-dihaloacetone; wherein the ketone-modified polypeptide comprises a linking group of the formula [PP]—S—CH$_2$—C(=O)—CH$_2$—S—[PP], where each S is a sulfur from the disulfide bond, and [PP] indicates where the ends of the linking group are attached to the polypeptide; and
   contacting the ketone-modified polypeptide with a group of the formula R—O—NH$_2$ in the presence of an amine promoter and at a polypeptide concentration of at least about 1 mg/mL, wherein the group of Formula R—O—NH$_2$ is a compound of the formula H$_2$N—O-L-PL where L represents a linker, and PL represents a payload group.

2. The method of claim 1, wherein the 1,3-dihaloacetone is 1,3-dichloroacetone.

3. The method of claim 1, wherein the reducing agent is a water-soluble phosphine or phosphine salt.

4. The method of claim 1, wherein the polypeptide is an antibody or antibody fragment.

5. The method of claim 1, wherein the amine promoter is a carboxy-substituted aniline or an acyl hydrazine.

6. The method of claim 1, wherein the ketone-modified polypeptide is of the formula

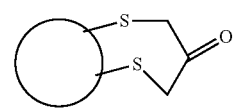

where the circle represents the polypeptide, and each sulfur atom is the sulfhydryl of a cysteine residue of the polypeptide.

7. The method of claim 1, wherein the polypeptide is an antibody.

8. The method of claim 1, wherein the polypeptide is a vaccine carrier.

9. The method of claim 1, wherein the payload comprises a therapeutic agent.

10. The method of claim 1, wherein the payload comprises a detectable label or a binding group.

11. The method of claim 1, wherein the oxime-modified polypeptide is of the formula:

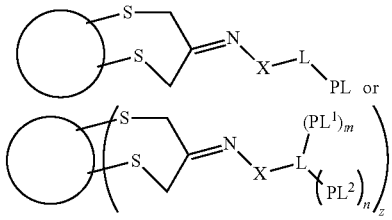

wherein X is O, L represents a linker, z is an integer from 1 to 10, m and n are each independently 1 to 10, and PL, $PL^1$, and $PL^2$ independently at each occurrence represent a payload group.

12. The method of claim 11, wherein L comprises a cleavable linking moiety.

13. The method of claim 12, herein L comprises at least one spacer selected from the group consisting of:

(a) a bond, —O—, —S—, —NH—, —N(($C_1$-$C_6$)alkyl)H—, —NH—C(O)—NH—, —C(O)—NH—, —NH—C(O)—;

(b) ($C_1$-$C_{20}$)alkylene, ($C_2$-$C_{20}$)alkenylene, ($C_2$-$C_{20}$)alkynylene, —Z—($C_1$-$C_2$)alkylene, —Z—($C_2$-$C_{20}$)alkenylene, —Z—($C_2$-$C_{20}$)alkynylene, ($C_1$-$C_{20}$)alkylene-Z—($C_1$-$C_{20}$)alkylene, ($C_2$-$C_{20}$)alkenylene-Z—($C_2$-$C_{20}$)alkenylene, ($C_2$-$C_{20}$)alkynylene-Z—($C_2$-$C_{20}$)alkynylene, where Z is —NH—, —N($C_1$-$C_6$alkyl)-, —NH—C(O)—NH—, —C(O)—NH—, —NH—C(O)—, ($C_3$-$C_7$)cycloalkylene, phenylene, heteroarylene, or heterocyclene and where said ($C_1$-$C_{20}$)alkylene, said ($C_2$-$C_{20}$)alkenylene, and said ($C_2$-$C_{20}$)alkynylene moieties each independently optionally contain 1-10 oxygen atoms interspersed within said moieties;

(c) ($C_3$-$C_7$)cycloalkylene, ($C_3$-$C_7$)cycloalkylene-Y—($C_3$-$C_7$)cycloalkylene, —Y—($C_3$-$C_7$)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is ($C_1$-$C_{20}$)alkylene, ($C_2$-$C_{20}$)alkenylene, ($C_2$-$C_{20}$)alkynylene, —O—, —C(O)—, —S—, —NH—, —N(($C_1$-$C_6$)alkyl)-, —NH—C(O)—NH—, —C(O)—NH—, or —NH—C(O)— and where said ($C_3$-$C_7$)cycloalkylene, said phenylene, said heteroarylene, and said heterocyclene moieties are each individually optionally substituted with 1 to 3 substituents selected from halo, ($C_1$-$C_4$)alkyl or halo-substituted ($C_1$-$C_4$)alkyl;

(d) —[$OCH_2CH_2$]$_v$- or -J-{$CH_2$[$OCH_2CH_2$]$_v$}$_w$—where v is 1-2,000, w is 1-4, and J is $CH_2$ or NH;

(e) a peptide comprising 1 to 100 amino acids; and (f) Dendritic macromolecules.

* * * * *